(12) United States Patent
Sprecher et al.

(10) Patent No.: US 8,912,142 B2
(45) Date of Patent: Dec. 16, 2014

(54) METHOD OF REGULATING PROLIFERATION AND DIFFERENTIATION OF KERATINOCYES

(75) Inventors: Eli Sprecher, Tel-Aviv (IL); Janna Nousbeck, Givataim (IL)

(73) Assignees: The Medical Research, Infrastructure and Health Services Fund of the Tel Aviv Medical Center, Tel-Aviv (IL); Rappaport Family Institute for Research in the Medical Sciences, Haifa (IL)

( * ) Notice: Subject to any disclaimer, the term of this patent is extended or adjusted under 35 U.S.C. 154(b) by 338 days.

(21) Appl. No.: 13/127,058

(22) PCT Filed: Feb. 28, 2010

(86) PCT No.: PCT/IL2010/000167
§ 371 (c)(1),
(2), (4) Date: May 2, 2011

(87) PCT Pub. No.: WO2010/113146
PCT Pub. Date: Oct. 7, 2010

(65) Prior Publication Data
US 2011/0207665 A1 Aug. 25, 2011

Related U.S. Application Data

(60) Provisional application No. 61/202,760, filed on Apr. 1, 2009.

(51) Int. Cl.
*A61K 38/17* (2006.01)

(52) U.S. Cl.
USPC .......... 514/8.7; 530/350; 514/21.2; 514/44 R; 514/23.5

(58) Field of Classification Search
USPC ................ 530/350; 514/8.7, 863, 21.2, 44 R; 536/23.5
IPC ........ A61K 38/1754; C12N 15/11; C07K 14/35
See application file for complete search history.

(56) References Cited

U.S. PATENT DOCUMENTS 6,139,862 A * 10/2000 Khavinson et al. .......... 424/436

FOREIGN PATENT DOCUMENTS

| WO | WO 99/61640 | 12/1999 |
| WO | WO 02/24219 | 3/2002 |
| WO | WO 2007/039255 | 4/2007 |
| WO | WO 2009/036188 | 3/2009 |
| WO | WO 2010/113146 | 10/2010 |

OTHER PUBLICATIONS

Office Action Dated Oct. 10, 2013 From the Israel Patent Office Re. Application No. 215494 and Its Translation Into English.
Communication Pursuant to Article 94(3) EPC Dated Mar. 12, 2012 From the European Patent Office Re. Application No. 10710105.7.
Translation of Reason for Rejection Dated Mar. 31, 2014 From the Japanese Patent Office Re. Application No. 2012-502872.
Kim et al. "Terrein Inhibits Kkeratinocyte Proliferation Via ERK Inactivation and G2/M Cell Cycle Arrest", Experimental Dermatology, 17(4): 312-317, Nov. 2, 2007. Abstract.
International Preliminary Report on Patentability Dated Oct. 13, 2011 From the International Bureau of WIPO Re. Application No. PCT/IL2010/000167.
Communication Pursuant to Article 94(3) EPC Dated Aug. 3, 2012 From the European Patent Office Re. Application No. 10710105.7.
Translation of Notification of Office Action Dated Mar. 6, 2013 From the State Intellectual Property Office of the People's Republic of China Re. Application No. 201080024052.2.
Translation of Search Report Dated Mar. 6, 2013 From the State Intellectual Property Office of the People's Republic of China Re. Application No. 201080024052.2.
International Search Report and the Written Opinion Dated Jul. 13, 2010 From the International Searching Authority Re. Application No. PCT/IL2010/000167.
Hochberg et al. "Genomic-Scale Analysis of Psoriatic Skin Reveals Differentially Expressed Insulin-Like Growth Factor-Binding Protein-7 After Phototherapy", British Journal of Dermatology, XP002588596, 156(2): 289-300, Feb. 2007.
Nousbeck et al. "Insulin-Like Growth Factor-Binding Protein 7 Regulates Keratinocyte Proliferation, Differentiation and Apoptosis", Journal of Investigative Dermatology, XP002588598, 130: 378-387, 2010.
Oh et al. "Synthesis and Characterization of Insulin-Like Growth Factor-Binding Protein (IGFBP)-7", The Journal of Biological Chemistry, XP002588595, 271(48): 30322-30325, Nov. 29, 1996.
Schmitt et al. "Efficacy and Tolerability of Biological and Nonbiological Systemic Treatments for Moderate-to-Severe Psoriasis: Meta-Analysis of Randomized Controlled Trials", British Journal of Dermatology, XP002588597, 159: 513-526, 2008.
Communication Pursuant to Article 94(3) EPC Dated Feb. 17, 2014 From the European Patent Office Re. Application No. 10710105.7.

* cited by examiner

*Primary Examiner* — David Lukton

(57) ABSTRACT

Provided are methods of regulating keratinocytes proliferation and differentiation by subjecting keratinocytes to an agent capable of modulating activity or expression of IGFBP7, thereby regulating keratinocytes proliferation and differentiation. Also provided are methods of treating pathologies characterized by hyperproliferative keratinocytes by administering IGFBP7 polypeptide or a polynucleotide encoding IGFBP7 polypeptide to a subject.

13 Claims, 26 Drawing Sheets
(16 of 26 Drawing Sheet(s) Filed in Color)

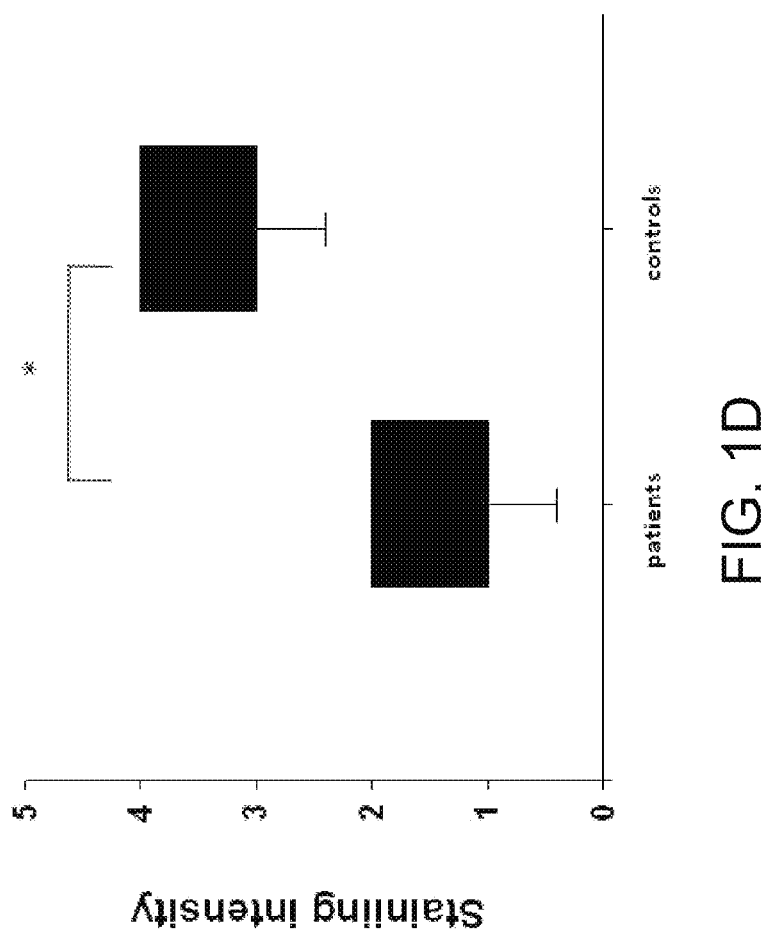
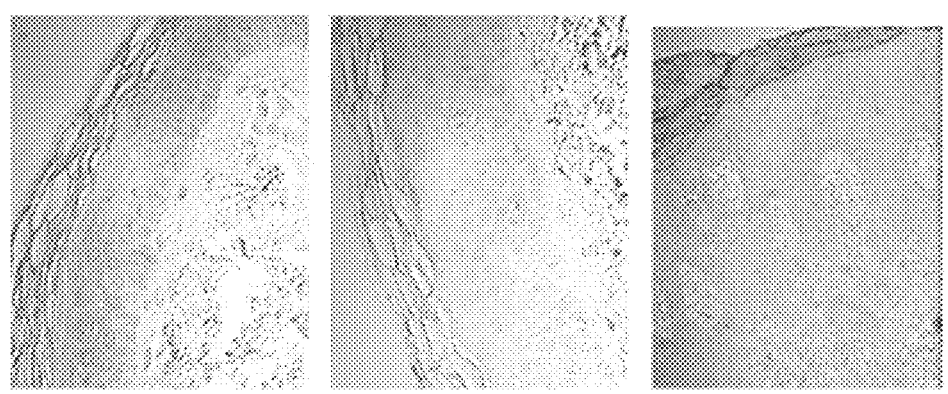
FIG. 1A
FIG. 1B
FIG. 1C
FIG. 1D

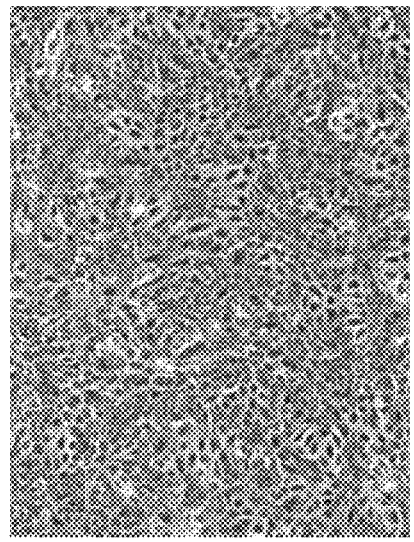
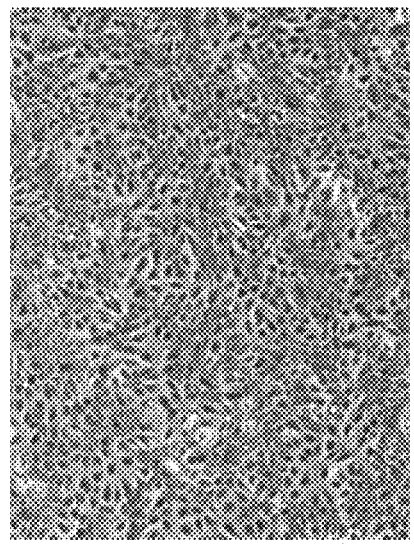
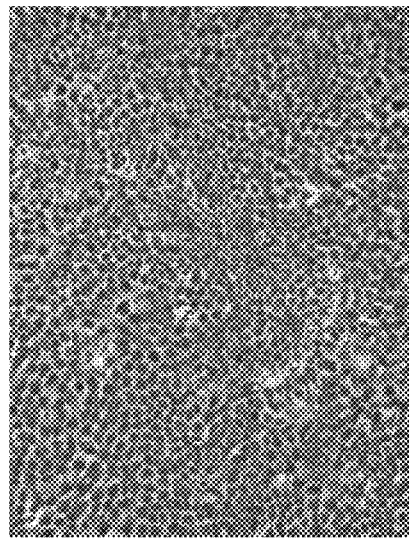
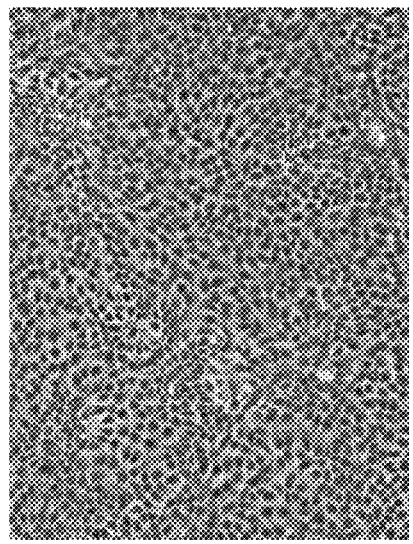
FIG. 9A IGFBP7 shRNA — Low calcium
FIG. 9B IGFBP7 shRNA — High calcium
FIG. 9C Control shRNA — Low calcium
FIG. 9D Control shRNA — High calcium

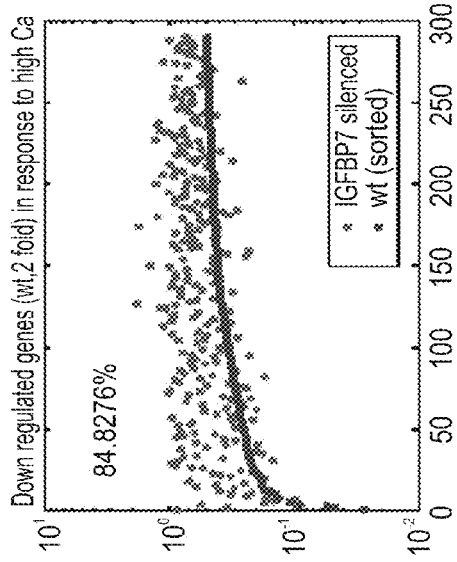
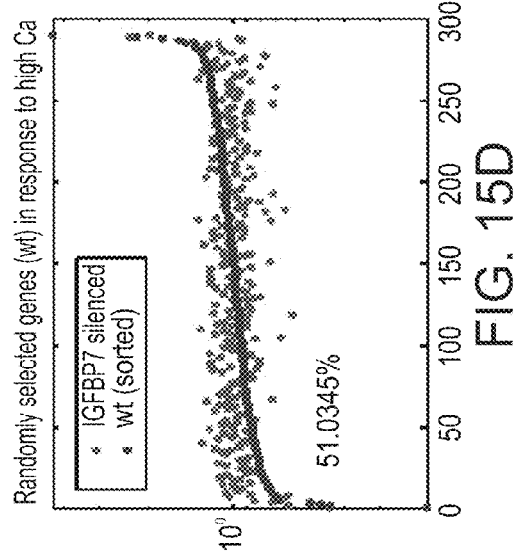
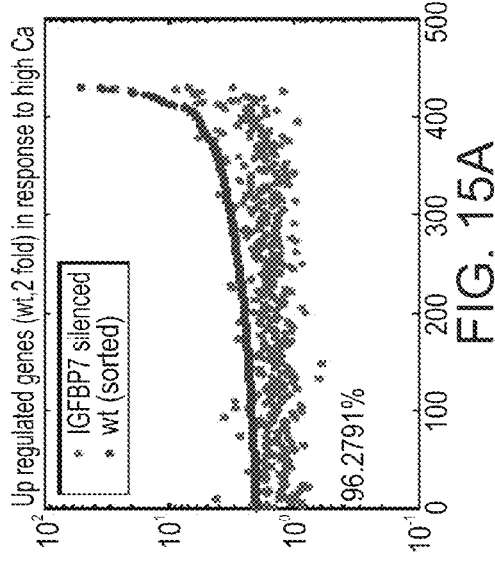
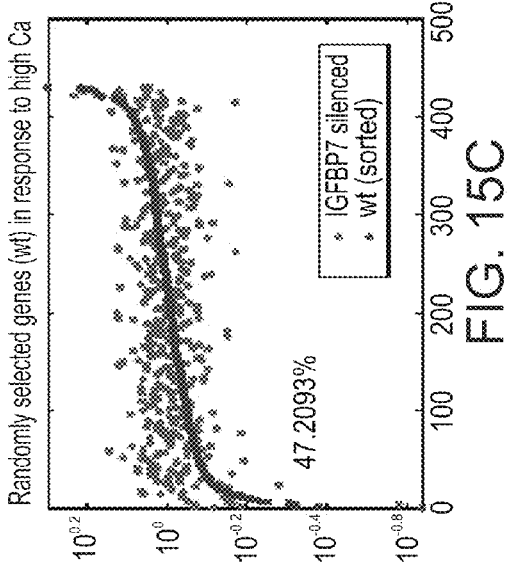
FIG. 15A
FIG. 15B
FIG. 15C
FIG. 15D

IGFBP7-specific siRNA

Control siRNA

METHOD OF REGULATING PROLIFERATION AND DIFFERENTIATION OF KERATINOCYES

RELATED APPLICATIONS

This application is a National Phase of PCT Patent Application No. PCT/IL2010/000167 having International filing date of Feb. 28, 2010, which claims the benefit of priority of U.S. Provisional Patent Application No. 61/202,760 filed on Apr. 1, 2009. The contents of the above applications are all incorporated herein by reference.

FIELD AND BACKGROUND OF THE INVENTION

The present invention, in some embodiments thereof, relates to methods and pharmaceutical compositions for treating pathologies characterized by hyperproliferative keratinocytes.

Psoriasis is a chronic inflammatory skin disease affecting approximately 2-5% of the general population worldwide. The etiology of psoriasis is multifactorial and it is thought to result from the interactions between environmental and genetic factors. Typical histopathological features in psoriasis include both epidermal (hyperparakeratosis) and immunological (neutrophil microabscesses and dermal mononuclear infiltrate and blood vessel proliferation) abnormalities. Psoriasis is characterized by increased proliferation, decreased apoptosis and abnormal differentiation of keratinocytes and can be often associated with other diseases or conditions such as arthritis, cardiovascular disease, chronic obstructive pulmonary disease (COPD), diabetes and the like.

Current treatments of psoriasis include the topical administration of coal tar, vitamin D derivatives, retinoids, and calcineurin inhibitors; phototherapy using UVB, NB-UVB, and/or laser; combined systemic and phototherapy (e.g., oral administration of psoralen followed by exposure to UVA); systemic administration of Cyclosporine, methotrexate, retinoids and the like; and administration of biological agents such as Alafacept, infliximab, etanercept and ustekinumab.

The etiology of psoriasis is not clear. Various candidate genes were found to be associated with genetic predisposition to develop the disease (Griffiths and Barker, 2007; Lowes et al., 2007; Nair et al., 2009; Nair et al., 2006; Yang et al., 2008; Zenz et al., 2008; Zenz and Wagner, 2006; Zhang et al., 2009), demonstrating the involvement of both immunological dysfunction and epidermal defects in the pathogenesis of the disease.

Various animal models have been used to mimic the phenotype of psoriasis. For example, inducible epidermal deletion of Jun proteins was found to cause psoriasis-like skin disease and arthritis (Zenz et al., 2005). In addition, loss of serum response factor (SRF) in keratinocytes was found to result in hyperproliferative skin disease in mice (Koegel et al., 2009). Furthermore, Shon et al. [Exp Dermatol. 2008 August; 17(8):703-12] reviewed animal models of the disease and found that these models reflect the dual etiology of psoriasis.

Genomic-scale analysis of psoriatic skin in patients before and after phototherapy revealed a marked up-regulation of IGFBP7, encoding the insulin-like growth factor binding protein 7 (IGFBP7) (Hochberg M., Zeligson S., et al., 2007).

IGFBP7 belongs to the IGFBP superfamily, a large group of secreted proteins, which share a common N-terminal cysteine rich domain. A total of 16 family members have been identified, 6 of which bind IGFs with a high affinity (IGFBP1-6), the other 10 members binding insulin growth factors (IGFs) with a low affinity. IGFBP7 (also called IGFBP-rP1 or MAC25) binds IGFs with a low affinity, but recognizes insulin with a high affinity, and thereby modifies its metabolism, distribution, and ability to bind to the insulin receptor. IGFBP7 has IGF/insulin-independent actions. For example, IGFBP7 contains a "follistatin module", which enables its binding to activin, a member of the TGF-β superfamily of growth factors, that regulates normal mammary cell function, gonadal functions and follicle stimulatory hormone (FSH) release. IGFBP7 has been shown to regulate cell proliferation, cell adhesion, cellular senescence and angiogenesis in different cancer cell lines (Akaogi et al., 1996; Burger et al., 2005; Ruan et al., 2007; Sato et al., 2007; Wilson et al., 2002). More recently, IGFBP7 has been shown to mediate senescence and apoptosis in melanocytes and to suppress melanoma growth in vivo (Wajapeyee et al., 2008).

IGFBP7 is expressed in a ubiquitous fashion and can be found in its secreted form in all human biological fluids such as serum, urine and amniotic fluid (Degeorges et al., 2000; Lopez-Bermejo et al., 2003). IGFBP7 is inactivated by proteolytic processing; in addition, hypermethylation has been reported to also affect its expression in neoplastic tissues. IGFBP7 is induced by TGF-β, glucocorticoids and retinoic acid. IGFBP7 has been found to be one of several keratinocyte-specific genes differentially expressed in keratinocytes compared with nonkeratinocyte cell types (Gazel et al., 2003).

U.S. Patent Application 20090035312 teaches methods of identifying specific target molecules for design of anti-angiogenic and vascular targeting approaches and inhibition of angiogenesis in vitro and in vivo using antibodies targeting of vimentin, CD59, HMGB1 and IGFBP7.

Additional background art include Candille et al., Science 2007; Lande et al., Nature 2008; Chamorro et al., J. Invest. Dermatolo. 2009; Duncan et al., J. Invest. Dermatol. 1994; Kruger-Krasagakis et al., Br. J. Dermatol. 2006; Wrone-Smith et al., Am. J. Pathol. 1997; Komine et al., J. Invest Dermatol. 2007; Rahmoun et al, J Invest Dermatol, 2009; Krueger and Bowcock, 2005; McKay and Leigh, 1995; Bernerd et al., 1992; Bovenschen et al., 2005; Vissers et al., 2008; Haider et al., 2006; Bowen et al., 2004; Gunduz et al., 2006; Yang et al., 2009; Laporte et al., 2000; Raj et al., 2006; Yamanaka et al., 1997; Genua et al., 2009; Neely et al., 1991; Sadagurski et al., 2007; Wertheimer et al., 2001; Wertheimer et al., 2000; Nickoloff et al., 2006.

SUMMARY OF THE INVENTION

According to an aspect of some embodiments of the present invention there is provided a method of treating a pathology characterized by hyperproliferative keratinocytes comprising administering to a subject in need thereof a therapeutically effective amount of an insulin-like growth factor binding protein 7 (IGFBP7) polypeptide or a nucleic acid sequence encoding the IGFBP7 polypeptide, thereby treating the pathology characterized by the hyperproliferative keratinocytes.

According to an aspect of some embodiments of the present invention there is provided a pharmaceutical composition comprising an insulin-like growth factor binding protein 7 (IGFBP7) polypeptide or a nucleic acid sequence encoding the IGFBP7 polypeptide and a pharmaceutically acceptable carrier formulated for topical administration.

According to an aspect of some embodiments of the present invention there is provided use of an insulin-like growth factor binding protein 7 (IGFBP7) polypeptide or a nucleic acid sequence encoding the IGFBP7 polypeptide for the manufacture of a medicament for the treatment of a pathology characterized by hyperproliferative keratinocytes.

According to an aspect of some embodiments of the present invention there is provided a method of regulating keratinocytes proliferation and differentiation the method comprising subjecting keratinocytes to an agent capable of modulating activity or expression of IGFBP7, thereby regulating keratinocytes proliferation and differentiation.

According to some embodiments of the invention, the pharmaceutical composition is identified for treatment of a pathology characterized by hyperproliferative keratinocytes.

According to some embodiments of the invention, the IGFBP7 polypeptide comprises at least a functional portion of IGFBP7.

According to some embodiments of the invention, the pathology characterized by the hyperproliferative keratinocytes is psoriasis.

According to some embodiments of the invention, the pathology characterized by the hyperproliferative keratinocytes is selected from the group consisting of psoriasis, lichen planus, pityriasis rubra pilaris (PRP), papulosquamous disease, dermatitis and lichen simplex chronicus.

According to some embodiments of the invention, the dermatitis is selected from the group consisting of atopic dermatitis and contact dermatisis.

According to some embodiments of the invention, the method further comprising administering to the subject an agent capable of at least partially reducing symptoms of the pathology, wherein the agent is suitable for topical or systemic administration and/or for treating the subject with light therapy.

According to some embodiments of the invention, the agent suitable for the topical administration is selected from the group consisting of a corticosteroid, a vitamin D analogue or derivative, anthralin, topical retinoid, calcineurin inhibitor, salicylic acid, coal tar and a moisturizer.

According to some embodiments of the invention, the light therapy is selected from the group consisting of sun light phototherapy, UVB phototherapy, narrowband UVB phototherapy, photochemotherapy, PUVA and excimer laser.

According to some embodiments of the invention, the agent suitable for the systemic administration is selected from the group consisting of a retinoid, an immunosuppressive drug, an immune-targeting biologic agent, an immunotoxin, and a tumor necrosis factor (TNF) blocking agent.

According to some embodiments of the invention, the pharmaceutical composition further comprising an agent selected from the group consisting of a corticosteroid, a vitamin D analogue, anthralin, a topical retinoid, a calcineurin inhibitor, salicylic acid, coal tar, a retinoid, an immunosuppressive drug, an immune-targeting biologic agent, an immunotoxin, and TNF blocking agent.

According to some embodiments of the invention, regulating keratinocytes proliferation and differentiation comprises downregulating the proliferation and promoting the differentiation of keratinocytes.

According to some embodiments of the invention, the agent capable of modulating activity or expression of the IGFBP7 comprises a polypeptide having an amino acid sequence of IGFBP7.

According to some embodiments of the invention, the agent capable of modulating activity or expression of the IGFBP7 comprises a polynucleotide encoding a polypeptide having an amino acid sequence of IGFBP7.

According to some embodiments of the invention, downregulating the proliferation and promoting the differentiation is for the treatment of psoriasis.

According to some embodiments of the invention, regulating keratinocytes proliferation and differentiation comprises upregulating the proliferation.

According to some embodiments of the invention, the agent capable of modulating activity or expression of the IGFBP7 is selected from the group consisting of an oligonucleotide capable of silencing IGFBP7 expression, a neutralizing antibody, a dominant negative IGF or insulin.

According to an aspect of some embodiments of the present invention there is provided a method of treating psoriasis in a subject in need thereof, the method comprising administering to the subject a therapeutically effective amount of an agent capable of upregulating activity or expression of IGFBP7, thereby treating psoriasis.

According to some embodiments of the invention, the method further comprising administering to the subject a medicament selected from the group consisting of topical therapy (corticosteroids, vitamin D analogues, anthralin, topical retinoids, calcineurin inhibitors, salicylic acid, coal tar and moisturizers), light therapy (sun light, UVB phototherapy, narrowband UVB therapy, photochemotherapy, excimer laser), and injected or oral therapy (retinoids), immunosuppressive drugs (methotrexate, cyclosporine), immune-targeting biologic agents, immunotoxins (denileukin) and TNF blocking biologics.

According to an aspect of some embodiments of the present invention there is provided a method of promoting skin regeneration the method comprising contacting the skin with an agent capable of downregulating activity or expression of IGFBP7, thereby promoting skin regeneration.

According to some embodiments of the invention, the agent is formulated for topical administration.

According to an aspect of some embodiments of the present invention there is provided a pharmaceutical composition comprising IFGBP7 and a pharmaceutically acceptable carrier formulated for topical administration.

According to an aspect of some embodiments of the present invention there is provided a pharmaceutical composition comprising an agent capable of down-regulating activity or expression of IFGBP7 and a pharmaceutically acceptable carrier formulated for topical administration.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-D are representative images of immunostaining analysis depicting expression of IGFBP7 protein in psoriasis. Tissue sections from patients affected with plaque psoriasis (n=13) or from healthy controls (n=13) were subjected to immunostaining analysis using the mouse anti-IGFBP7 or mouse anti-KRT14 antibodies (not shown) and counterstained with hematoxylin. FIG. 1A-A representative tissue section obtained from a healthy control and stained with the mouse anti-IGFBP7 antibody; FIG. 1B-A tissue section obtained from a healthy control and stained with non-immune serum (a negative control slide); FIG. 1C-A representative tissue section obtained from a patient affected with plaque psoriasis and stained with the mouse anti-IGFBP7 antibody. FIG. 1D-A histogram depicting staining intensity in psoriasis patients and controls. Staining intensity was graded from 1-4 by 2 independent observers. Data are presented as mean staining intensity grade. Bars indicate the group means (asterisk, $p<0.01$, mean±SD).

Figure 2A:
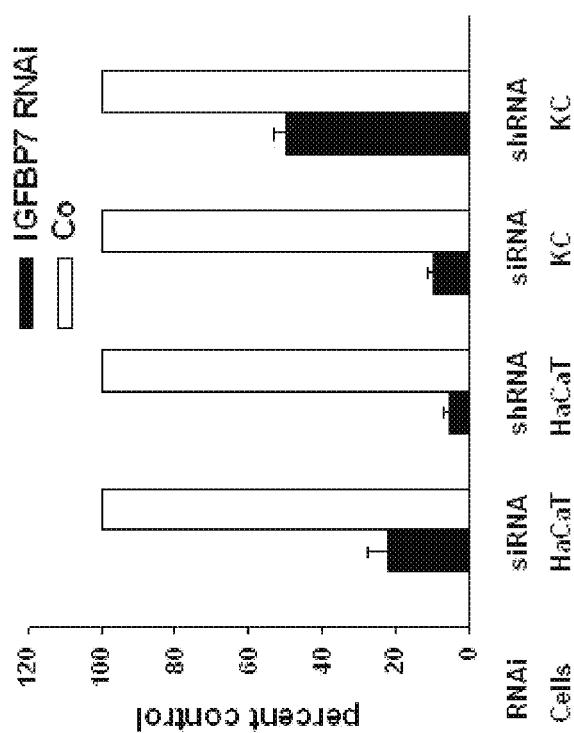
Figure 2B:
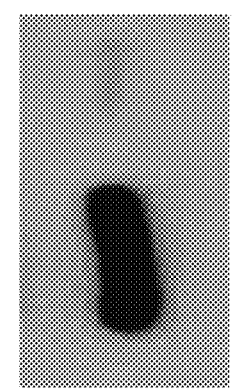

FIGS. 2A-B depict down-regulation of IGFBP7 expression in HaCat cells and primary human keratinocytes. FIG. 2A—HaCat cell lines and primary human keratinocytes were either transfected with siRNA or infected with a lentiviral vector expressing an IGFBP7-specific shRNA. Non specific siRNA or shRNA served as controls. RNA was extracted after 48 hours of culture. mRNA expression was normalized to beta actin (ACTB) or glyceraldehyde-3-phosphate dehydrogenase (GAPDH) (not shown). Results are expressed as percent of control. Data shown represent mean values±SD of three independent experiments performed in duplicates. FIG. 2B—Protein extracts from conditioned media obtained from HaCat cells stably expressing an IGFBP7-specific shRNA (shIGFBP7) or a non-specific shRNA (Co) were analyzed by immunoblotting and probed with an anti-IGFBP7. Note the significant decrease in IGFBP7 expression in the cells infected with the IGFBP7-specific shRNA.

Figure 3A:
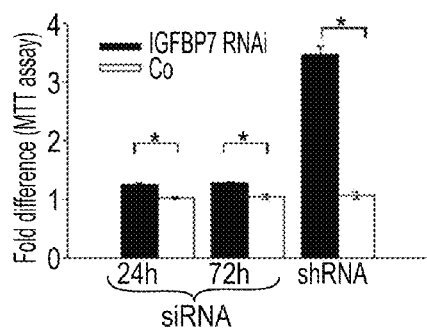
Figure 3B:
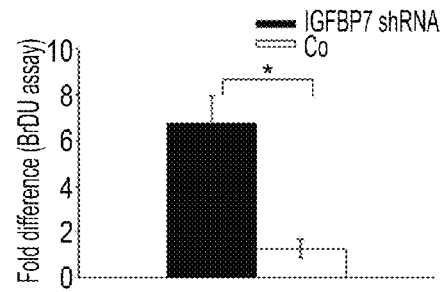
Figure 3C:
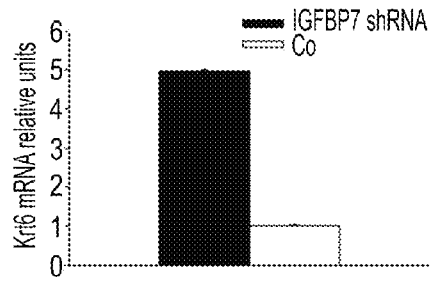
Figure 3D:
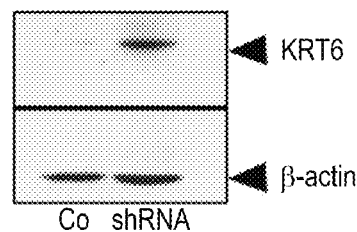
Figure 3E:
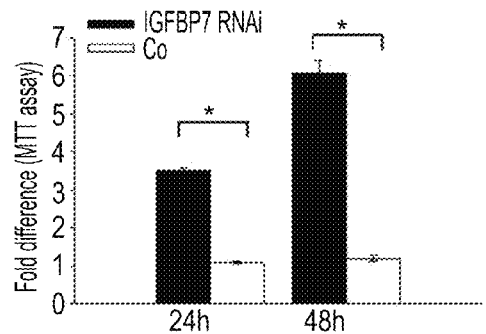
Figure 3F:
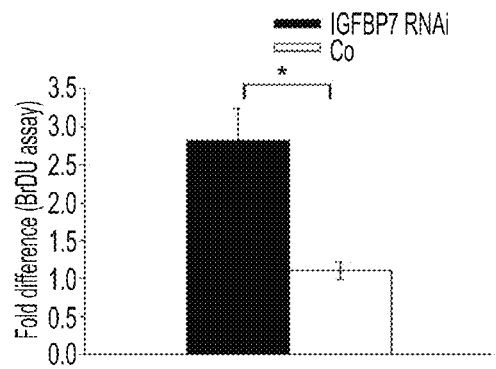

FIGS. 3A-F depict viability and proliferation assays of keratinocytes. FIG. 3A—Cell viability was assessed using the MTT assay in HaCat cells down-regulated for IGFBP7 using siRNA and cultured for 24 and 72 hours (h), as well as in HaCat cells stably expressing an IGFBP7-specific shRNA or a control shRNA. Data represent mean values±SD of three independent experiments. Asterisk, $p<0.01$ compared with control cells. FIG. 3B—HaCat cells stably expressing an IGFBP7-specific shRNA or a control shRNA were assessed using the BrDu assay (stable transfection). Data represent mean values±SD of three independent experiments. Asterisk, $p<0.01$ compared with control cells. FIGS. 3C and D—KRT6a mRNA and protein levels were assessed by qRT-PCR (FIG. 3C) and immunoblotting (FIG. 3D) in HaCat cells stably expressing an IGFBP7-specific shRNA or a control shRNA. FIGS. 3E and F—Primary keratinocytes were transiently transfected with IGFBP7-specific siRNA (IGFBP7) or with control siRNA (control) and assessed using the MTT assay (FIG. 3E; 24 and 48 hours post transfection) and the BrDu assay (FIG. 3F; 24 hours post transfection). Data represent mean values±SD of three independent experiments (Asterisk, $p<0.01$ compared with control cells). Note that when IGFBP7 is downregulated the keratinocytes are more viable and proliferative, and express higher levels of Krt6, a marker of epidermal proliferation, as compared to control cells. These results demonstrate the antiproliferative effect of IGFBP7 on keratinocytes.

Figure 4A:
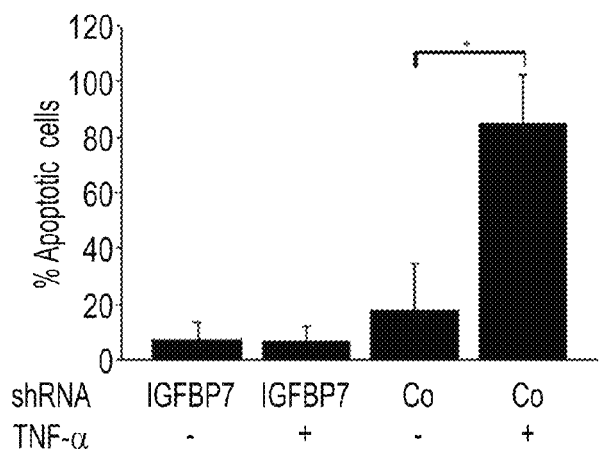
Figure 4B:
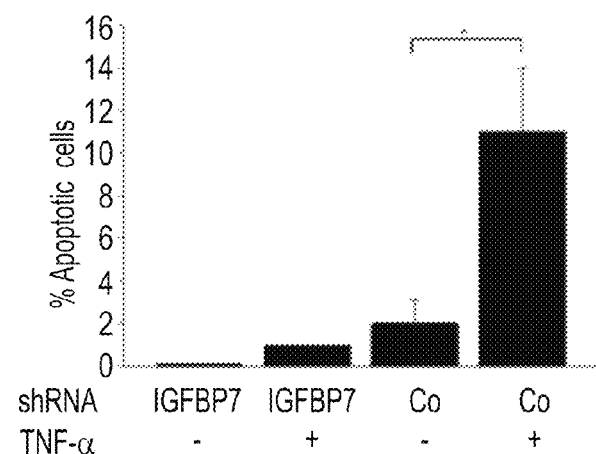
Figure 4C:
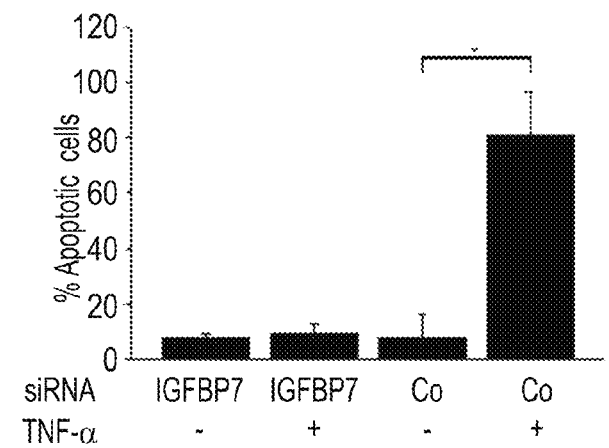

FIGS. 4A-C depict apoptosis assays in HaCat or primary keratinocyte cells. FIGS. 4A-B—HaCat cells stably expressing IGFBP7-specific (IGFBP7) or control shRNA (Co) (scrambled control), were exposed to 10 ng/µl of recombinant tumor necrosis factor-alpha (TNF-α) (+) or vehicle (−) 24 hours after transfection. Apoptosis was measured using the TUNEL assay (FIG. 4A) or the Annexin V assay (FIG. 4B). FIG. 4C—Primary keratinocytes were transiently transfected with IGFBP7-specific siRNA (IGFBP7) or with scrambled control siRNA (Co) and exposed to 10 ng/µl of recombinant TNF-α (+) or vehicle (−). Apoptotic activity was assessed by the TUNEL assay. All experiments were repeated three times. Results are provided as mean values±SD. Results were considered significant for *$p<0.01$. Note the significantly low apoptosis levels in keratinocytes cells in which IGFBP7 is downregulated, and the lack of apoptosis induction by TNF-α in cells in which IGFBP7 is downregulated. These results demonstrate that IGFBP7 is required for TNF-α-mediated apoptosis and that a decreased expression of IGFBP7 is associated with a decreased apoptosis in human keratinocytes.

Figure 5A:
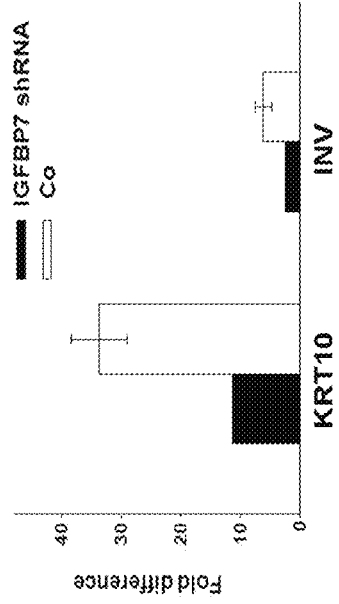
Figure 5B:
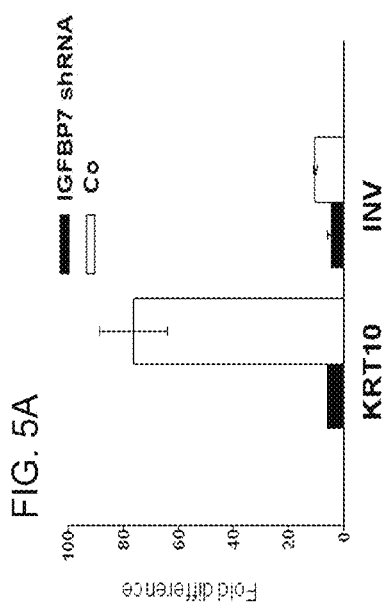
Figure 5C:
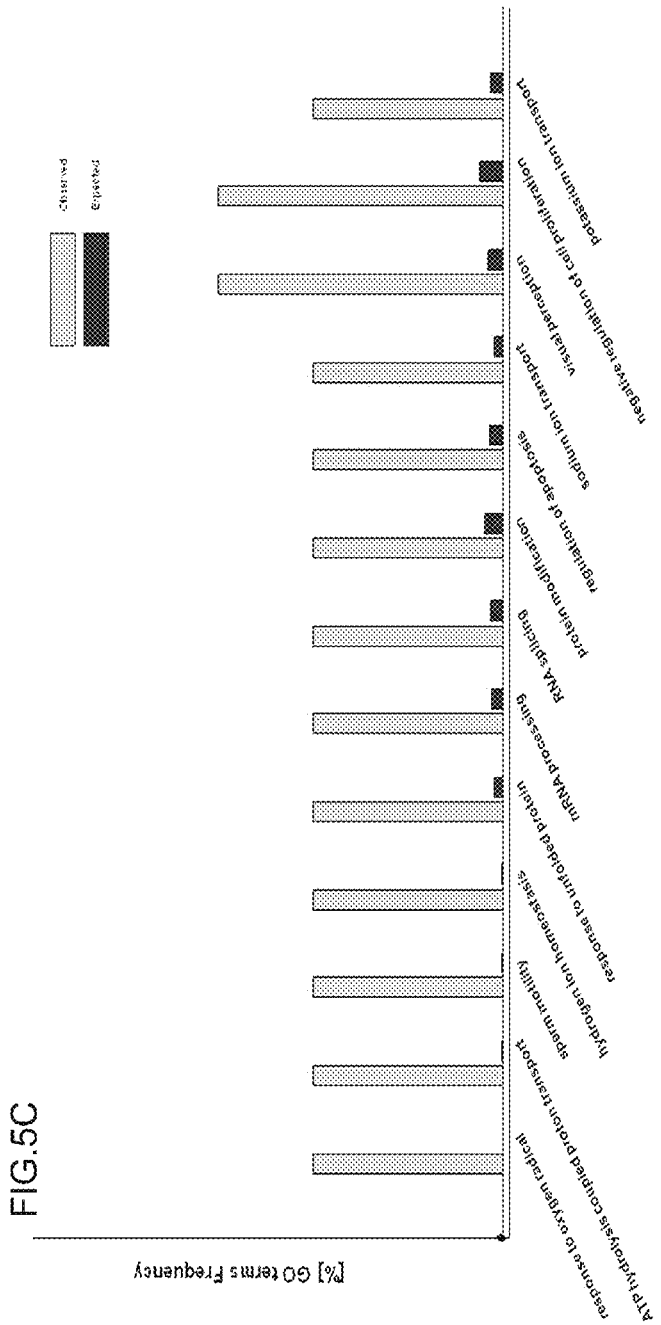

FIGS. 5A-C depict differentiation-associated events in HaCat or primary keratinocyte cells. FIGS. 5A and B—HaCat cells (FIG. 5A) or primary human keratinocytes (FIG. 5B) stably expressing an IGFBP-specific or a control shRNA were induced to differentiate by raising the extracellular calcium concentration. KRT10 and involucrin (INV) gene expression was assessed as a measure of early and late differentiation-associated events, respectively. Data represent mean values±SD of three independent experiments performed in duplicates. Data represent mean values±SD of three independent experiments performed in duplicates; These results demonstrate that IGFBP7 is required for calcium-induced keratinocyte differentiation. FIG. 5C-A global process GO term analysis was performed using the top 100 genes that showed a maximal response to IGFBP7 silencing following calcium induction in data sets obtained in primary keratinocytes and in HaCat cells. Significant terms (p value<0.01) encompass processes of direct relevance to cell proliferation and differentiation: response to oxygen radical; ATP hydrolysis coupled proton transport; sperm motility; hydrogen ion homeostasis; response to unfold protein; mRNA processing; RNA splicing; protein modification; regulation of apoptosis; sodium ion transport; visual perception; negative regulation of cell proliferation; potassium ion transport. The green bars correspond to the observed frequency of the GO terms identified as compared with their expected frequency (brown bars).

Figure 6A:
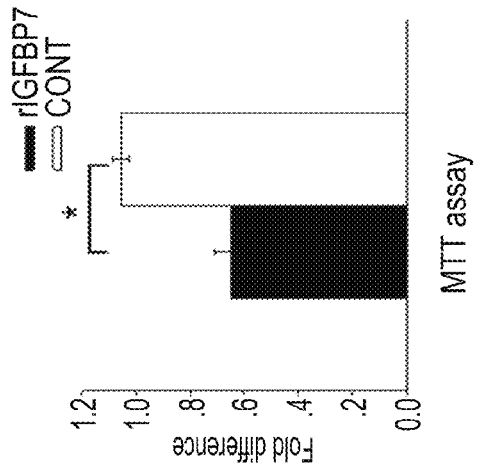
Figure 6B:
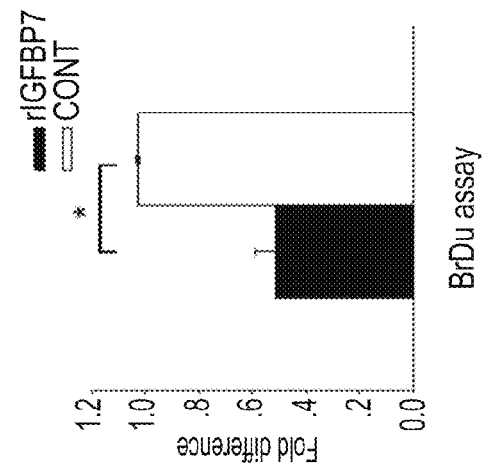
Figure 6C:
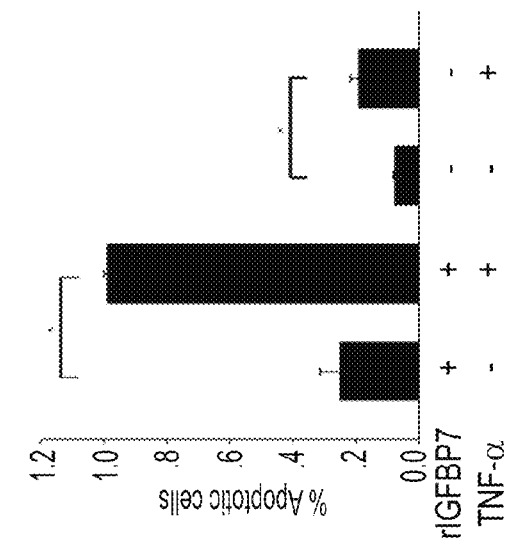

FIGS. 6A-C depict cell viability and proliferation assays of primary keratinocytes which exogenously express IGFBP7. Primary keratinocytes were treated with 1.8 µg/µl human recombinant IGFBP7 polypeptide (rIGFBP7; R&D systems Inc. Catalogue No. 1334-B7-025) for 72 hours, and then cultured in a medium lacking rIGFBP7 for 12 hours. FIGS. 6A-B—Cell viability and proliferation were assessed using the MTT (FIG. 6A) and BrDU (FIG. 6B) assays. FIG. 6C—Apoptosis was quantitated by TUNEL assay. All experiments were repeated three times. Results are provided as mean values±SD. Results were considered significant for *$p<0.01$. Note that the IGFBP7 polypeptide induces TNF-α-mediated apoptosis in keratinocyte cells (FIG. 6C) and reduces viability (FIG. 6A) and proliferation (FIG. 6B) of keratinocyte cells.

FIGS. 7A-D depict immuno assays of HaCat cells in which IGFBP7 is downregulated. To assess the effect of IGFBP7 down-regulation on signaling through the insulin receptor, protein was extracted from HaCat cells stably expressing an IGFBP7-specific shRNA or a control shRNA. Protein extracts were analyzed using immuno-blotting with antibodies directed against phosphorylated IRS-1 (pIRS, FIG. 7A, upper panel) and IRS-1 (FIG. 7A, middle panel) or phosphorylated ERK 1/2 (pERK, FIG. 7B, upper panel) and ERK2

Figure 7B:
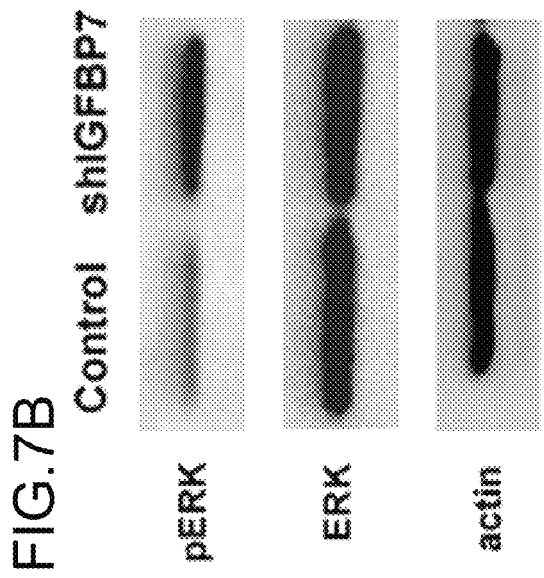
Figure 7D:
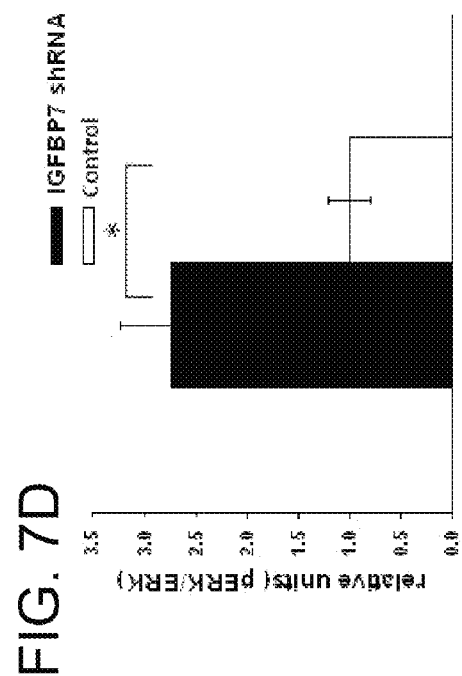
Figure 7A:
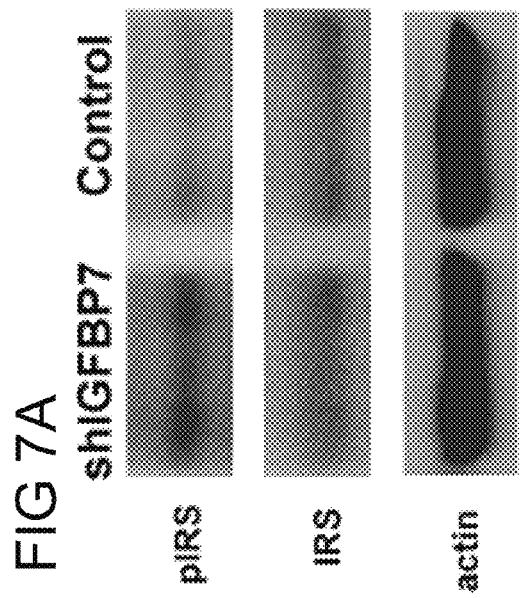
Figure 7C:
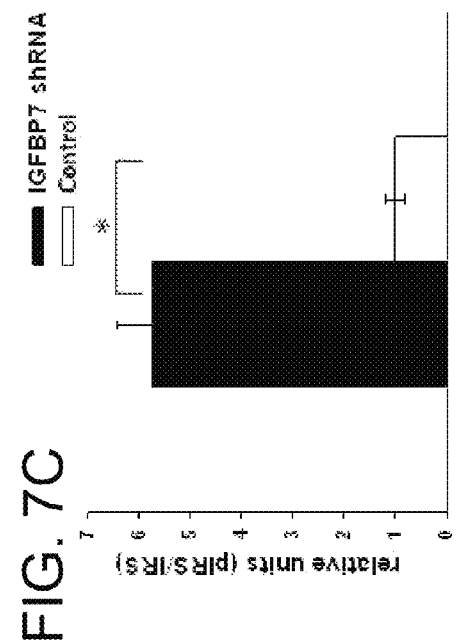

(FIG. 7B, middle panel). Immunostaining with antibodies directed against β-actin served as control (FIG. 7A, lower panel and FIG. 7B, lower panel). FIGS. 7C-D—Band intensities were assessed by densitometry. The experiments were repeated three times and the results are presented in a graph depicting the mean+SD. FIG. 7C—The ratio between the expression level of phosphorylated IRS-1 (pIRS) and IRS-1. FIG. 7D—The ratio between the expression level of phosphorylated ERK 1/2 (pERK) and ERK2. The results show that downregulation of IGFBP7 increases signaling through the insulin receptor as determined by increased phorphorylation of IRS-1 and tyrosine kinase ERK 1/2. In contrast, IGFBP7 did not influence SMAD 2/3 phosphorylation status (data not shown), suggesting that IGFBP7 affects KC (keratinocyte cells) through the modulation of IGF/insulin signaling.

Figure 8:
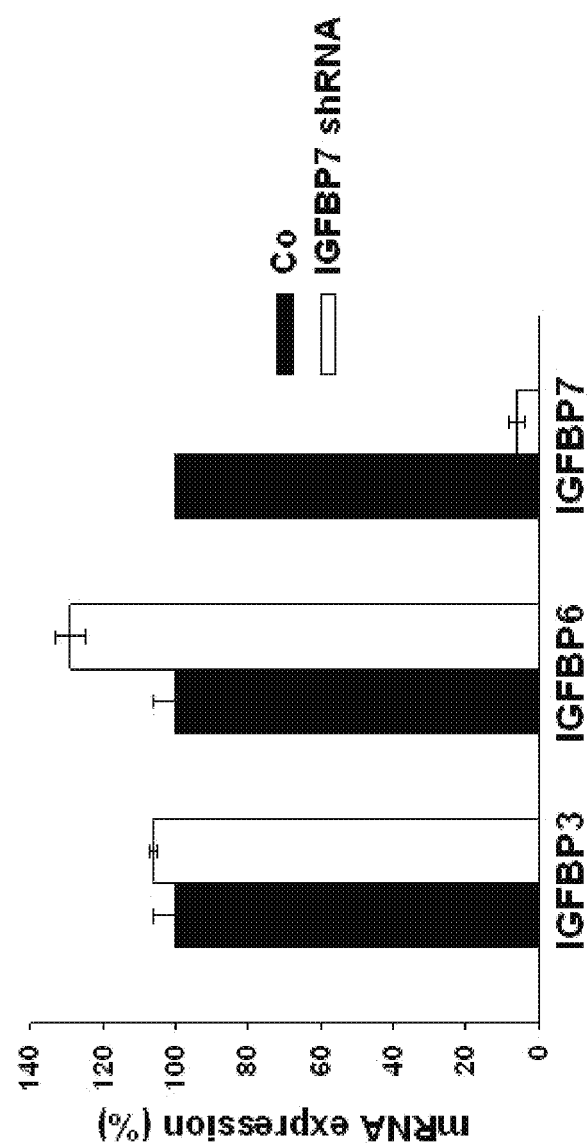

FIG. 8 is a histogram depicting mRNA expression levels of IGFBP3, IGFBP6 and IGFBP7 in HaCat cells in which IBFBP7 is downregulated by siRNA. RNA was extracted from HaCat cells stably expressing an IGFBP7-specific shRNA (IGFBP7 shRNA) or a non specific shRNA (Co). IGFBP3, IGFBP6 and IGFBP7 mRNA expression was assessed using qRT-PCR and normalized to ACTB or GAPDH. Results are expressed as percent of control. Data shown represent mean values±SD. Note that downregulation of IGFBP7 significantly reduced mRNA levels of IGFBP7 but not the mRNA levels of IGFBP3 or IGFBP6.

FIGS. 9A-D are phase contrast microscopy images depicting morphological changes in HaCat cells in which IGFBP7 is downregulated by siRNA following calcium-induced differentiation. HaCat cells stably transfected with an IGFBP7-specific (FIGS. 9A and B) or a control (FIGS. 9C and D) shRNA were plated at high density (80%) and cultured for 4 days in the presence of low concentrations (FIGS. 9A and 9C) or high concentrations (FIGS. 9B and 9D) of extracellular calcium and examined by phase contrast microscopy. While control cells adopted a typical rounded and coble-stoned appearance, no significant changes were seen in cells downregulated for IGFBP7.

Figure 10:
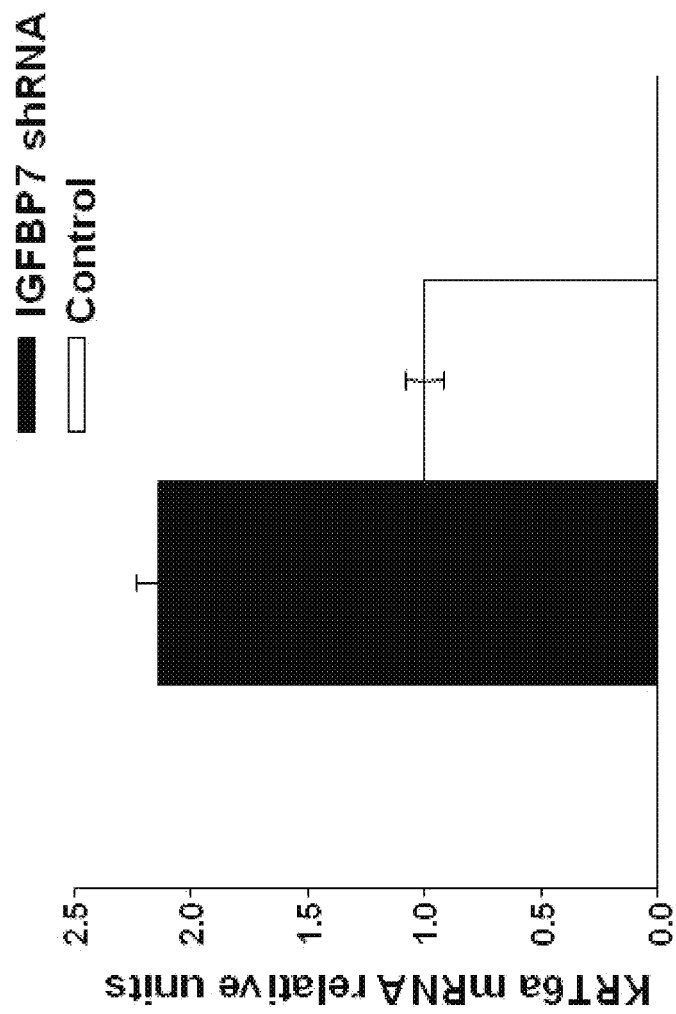

FIG. 10 is a histogram depicting KRT6a gene expression in primary keratinocytes in which IGFBP7 is down-regulated by shRNA. KRT6a mRNA levels were assessed by qRT-PCR in primary keratinocytes transiently down-regulated for IGFBP7 using a specific shRNA, as described in General Materials and Experimental Methods. Note the upregulation of KRT6a mRNA levels in keratinocytes in which IGFBP7 is down-regulated.

Figure 11:
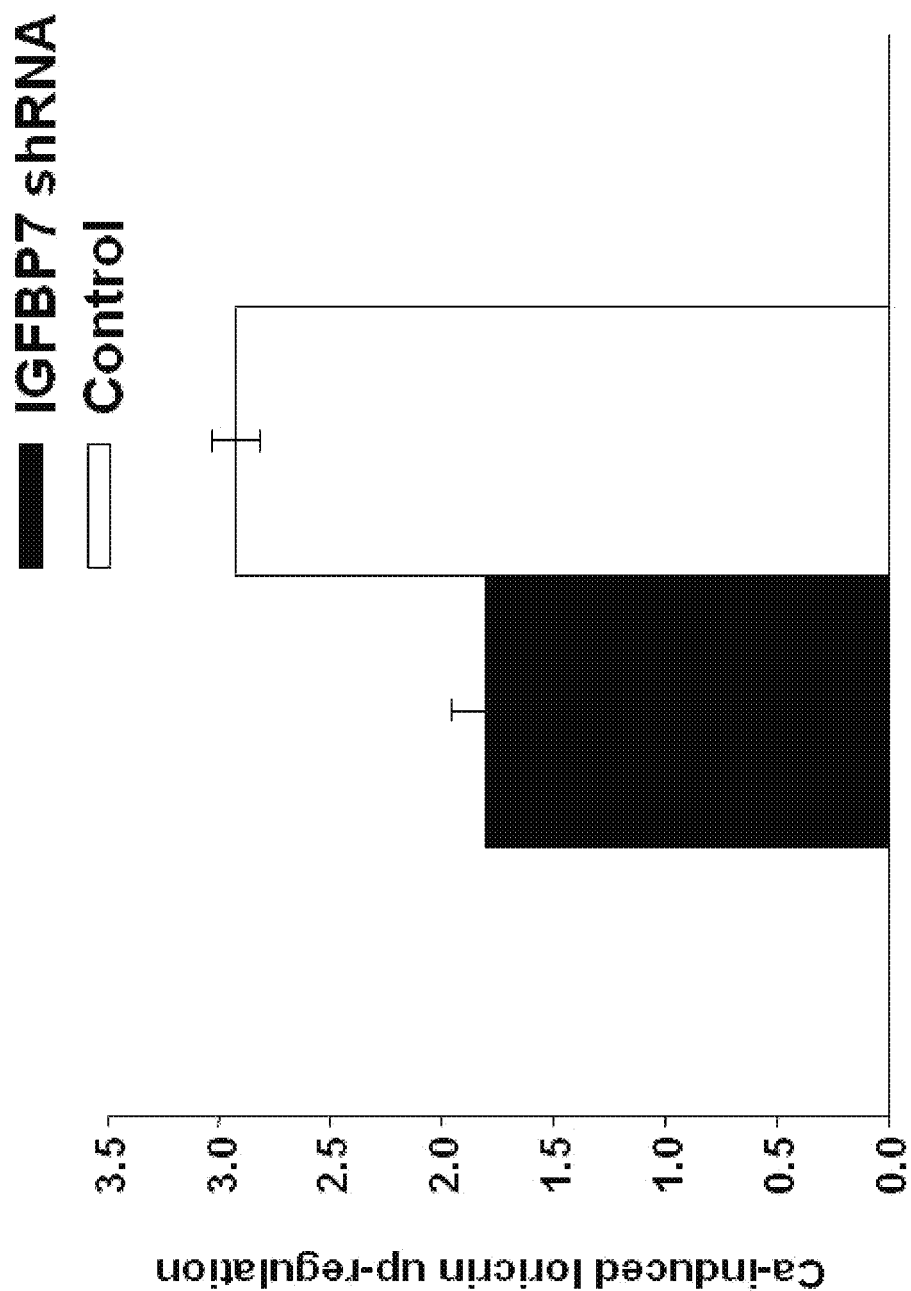

FIG. 11 is a histogram depicting calcium-induced expression of loricrin in HaCat cells. HaCat cells stably expressing an IGFBP7-specific or a control shRNA were induced to differentiate by raising the extracellular calcium concentration. Loricrin (LOR) gene expression was assessed using qRT-PCR 4 days later. Data represent mean values±SD of three independent experiments performed in duplicate. Note that while calcium induced up-regulation of loricrin in cells expressing the control shRNA, the level of loricrin expression was significantly lower in cells expressing the IGFBP7-shRNA.

Figure 12:
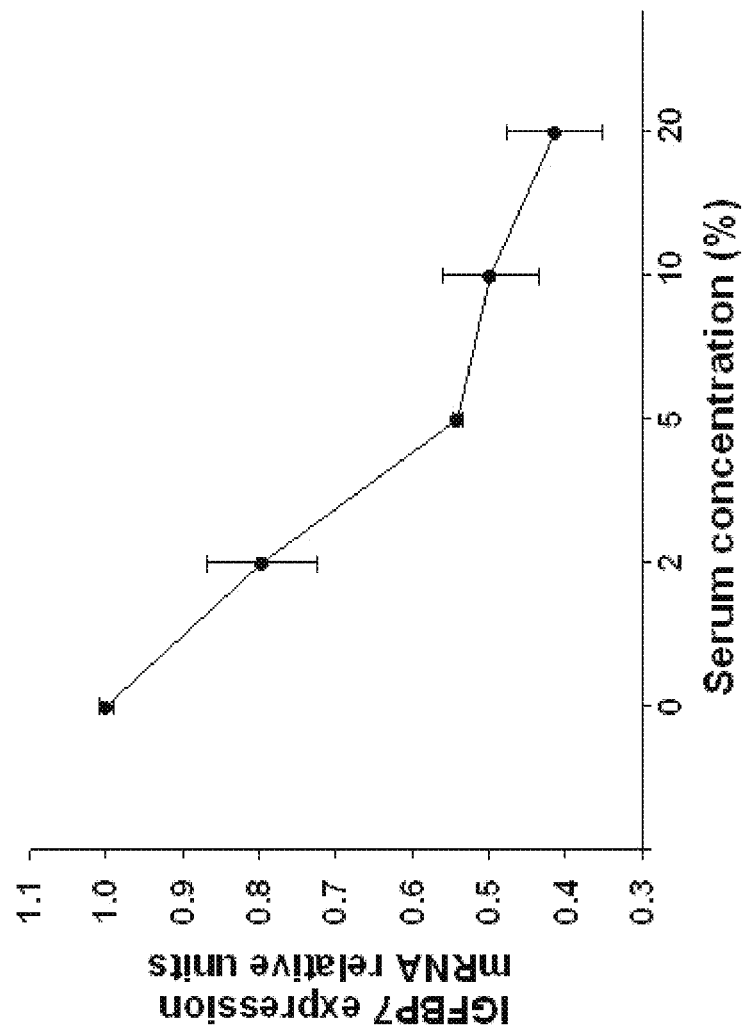

FIG. 12 is a graph depicting the effect of serum on IGFBP7 expression. HaCat cells were cultured in the presence of increasing concentrations of fetal calf serum. RNA was extracted 48 hours later and assessed for IGFBP7 expression using qRT-PCR and normalized to ACTB or GAPDH. Data shown represent mean values±SD. Note that serum decreases the IGFBP7 expression level.

Figure 13:
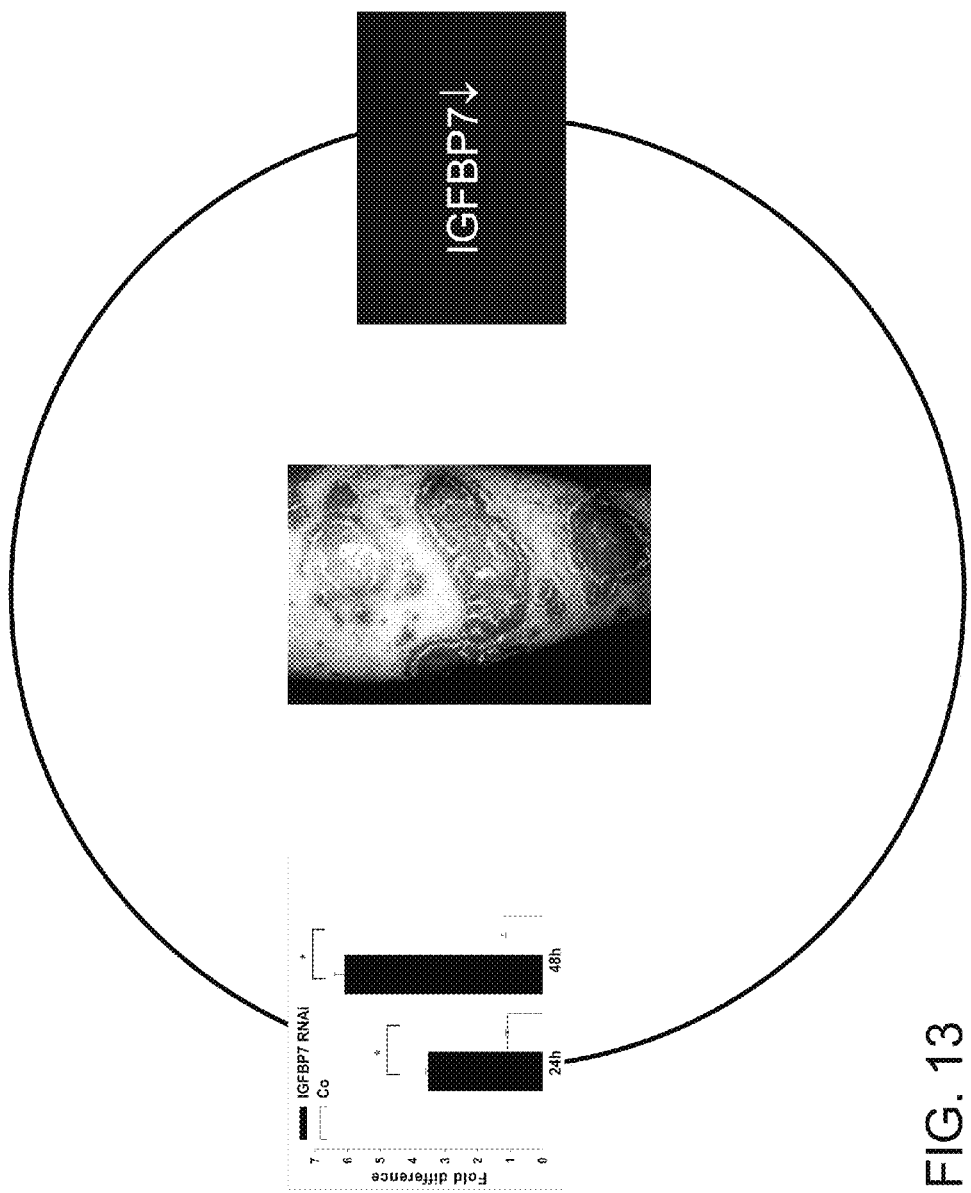

FIG. 13 depicts a model according to some embodiments of the invention: as increasing concentrations of growth factors, which are known to induce cell proliferation, were associated with decreased IGFBP7 expression, and decreased IGFBP7 expression is associated with increased proliferative activity, psoriasis can be conceived, as far as IGFBP7 role is considered, as resulting from a vicious circle, where each of the two elements (IGFBP7 and keratinocyte proliferation) consolidate the effect of the other.

Figure 14B:
Figure 14A:
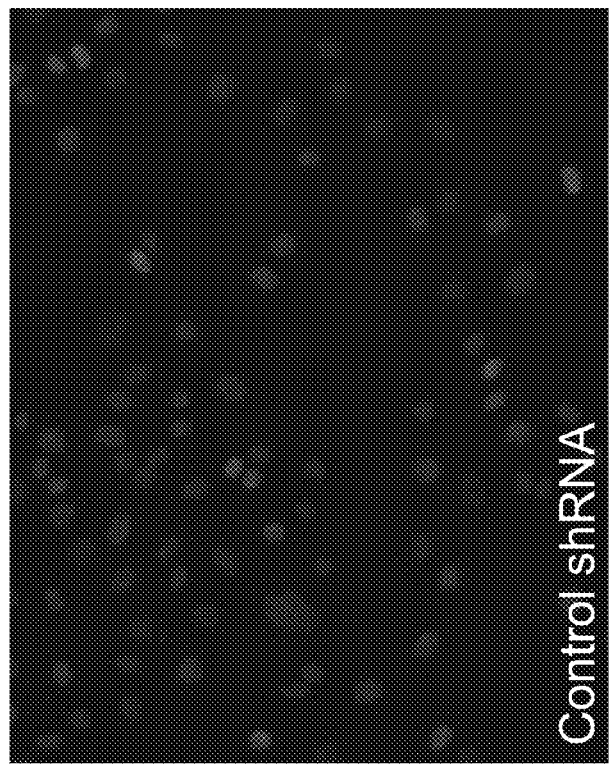

FIGS. 14A-B are fluorescent microscopy images depicting the TUNEL assay in keratinocytes. Primary keratinocytes transiently down-regulated for IGFBP7 using a specific shRNA (FIG. 14B) or a control shRNA (FIG. 14A) were subjected to TUNEL assay. Note the red staining of keratinocyte cells (corresponding to apoptotic cells) treated with a control shRNA but not with the IFGBP7-specific shRNA indicating inhibition of apoptosis in cells treated with IGFBP7 shRNA.

FIGS. 15A-D are scatter plots analyses depicting changes in gene expression in response to high calcium in wild type and IGFBP7-silenced cells. FIGS. 15A-B are scatter plots comparing changes in expression level of all genes displaying >2-fold increase (FIG. 15A) or decrease (FIG. 15B) in expression following exposure to high calcium in wild type cells (blue dots) vs. IGFBP7 silenced cells (red dots). Note that while specific genes were significantly upregulated (FIG. 15A) or downregulated (FIG. 15B) in response to high calcium in wild type cells, in IGFBP7-silenced cells these genes were not significantly changed in response to high calcium. Significant attenuation of change in expression can be seen following IGFBP7 silencing in >95% of the genes that showed differential expression following exposure to high calcium concentrations in wild type cells (FIGS. 15A-B). FIGS. 15C-D are scatter plots comparing changes in expression level of genes displaying >2-fold increase (FIG. 15C) or decrease (FIG. 15D) in expression following exposure to high calcium in wild type cells (blue dots) vs. an identical number of randomly selected genes in IGFBP7 silenced cells (red dots). The effect seen in FIGS. 15A-B is specific to genes induced or repressed by calcium as it is not seen when the same comparison is performed on a set of genes randomly selected (FIGS. 15C-D).

Figure 16:
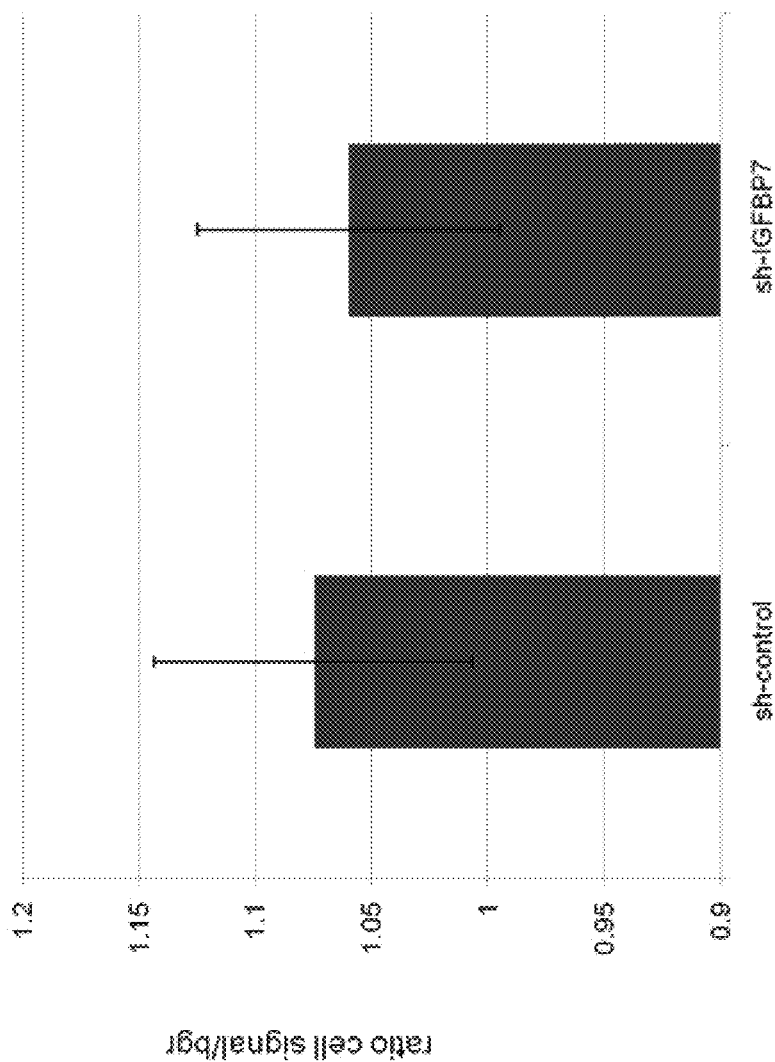

FIG. 16 is a histogram depicting the expression of beta-galactosidase, a marker for cell senescence. Note that IGFBP7 does not affect keratinocyte cell senescence.

Figure 17:
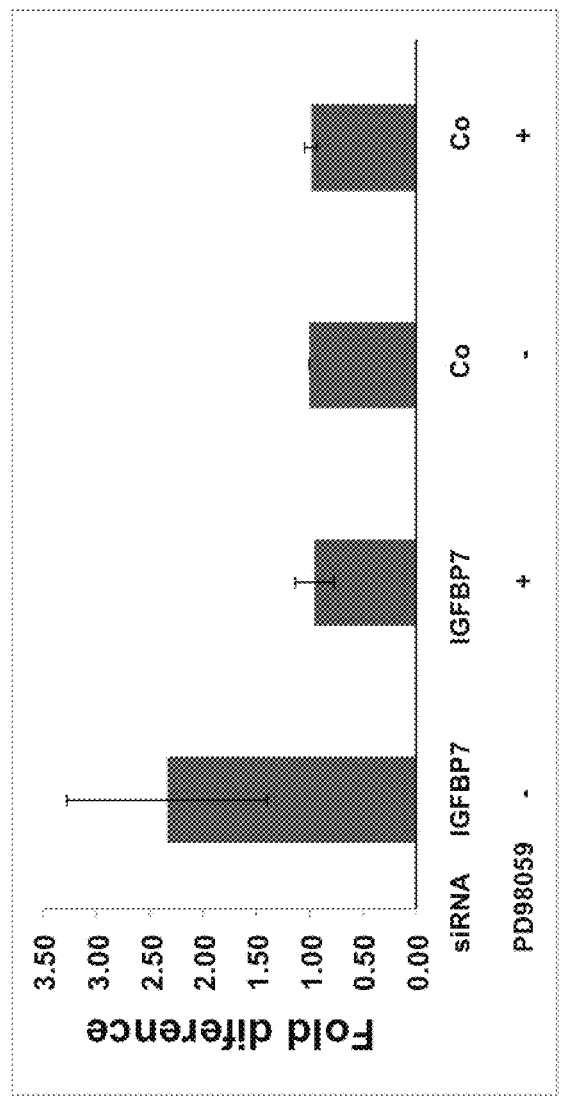

FIG. 17 is a histogram depicting the effect of ERK inhibition on keratinocytes proliferation in IFGBP7-silenced cells and control cells. Primary keratinocytes which were transfected with IGFBP7 siRNA were treated with 120 µM PD98059 (ERK inhibitor) for 72 hours, while refreshing the medium every 24 hours. Note that ERK inhibition attenuates cell proliferation induced by IGFBP7 down-regulation ($p<0.01$).

Figure 18:
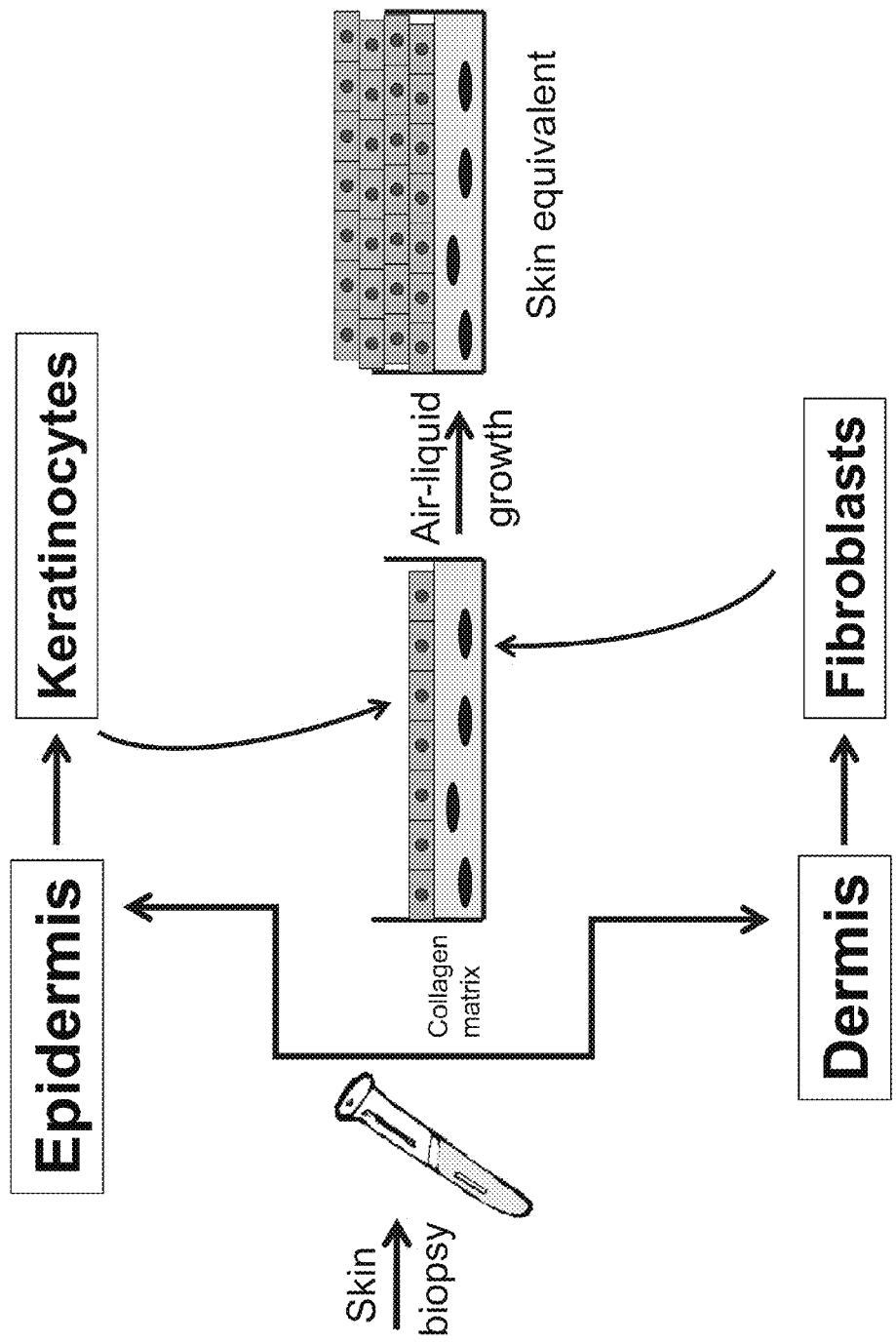

FIG. 18 is a schematic presentation describing the establishment of a tri-dimensional skin model. Briefly, primary keratinocytes and dermal fibroblasts were harvested from skin biopsies, the dermal fibroblasts were embedded into a collagen type I-containing matrix and keratinocytes were grown at air surface. Stratification occurred over a period of 2-3 weeks.

Figure 19:
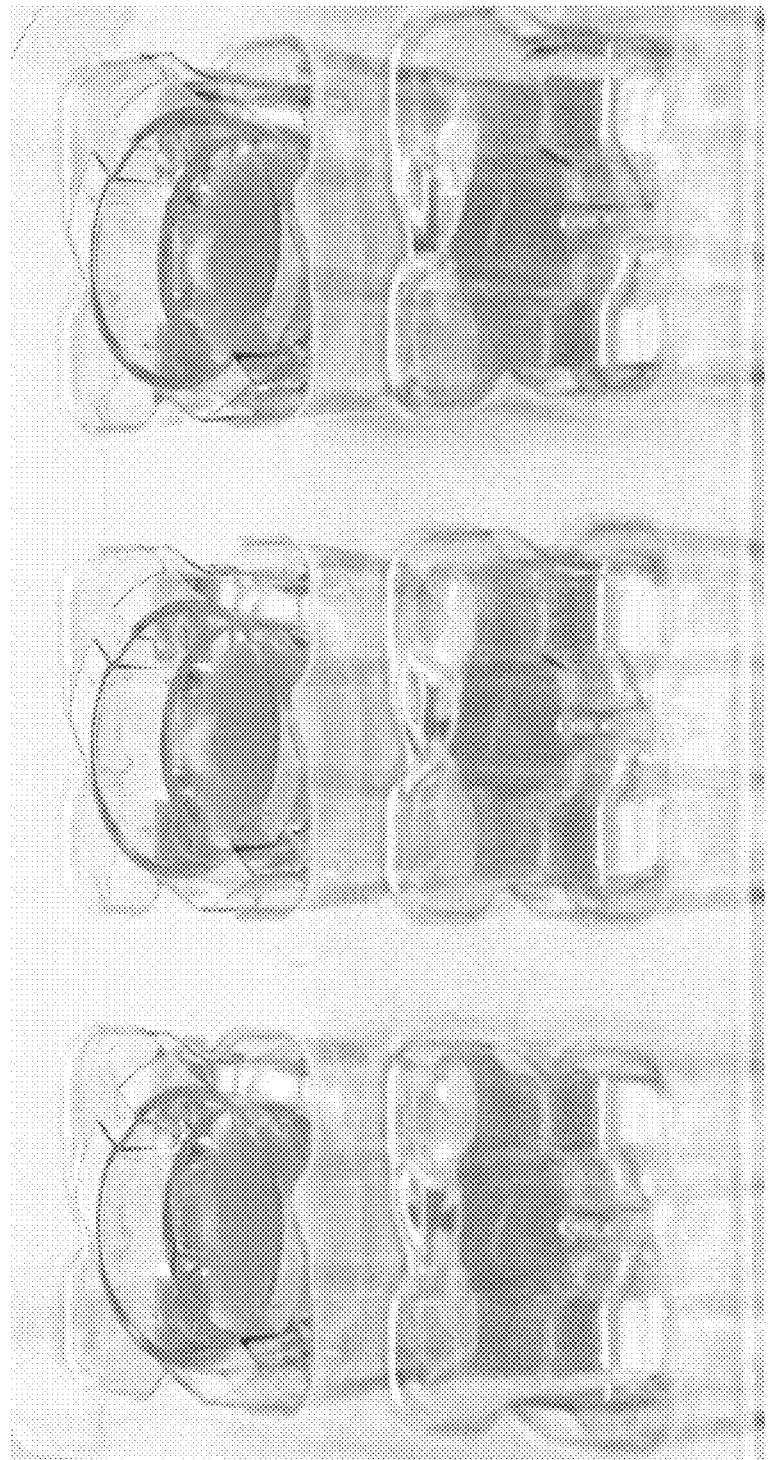

FIG. 19 is a photograph of special 6-well plates used to grow the cells at air-surface of the tri-dimensional model described in FIG. 18.

Figure 20A:
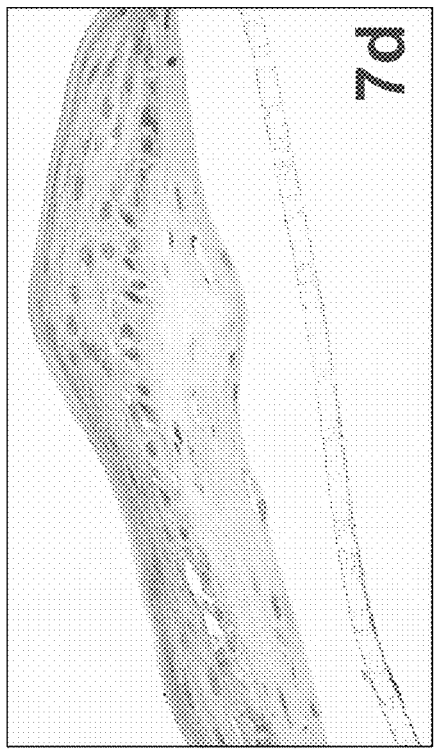
Figure 20B:
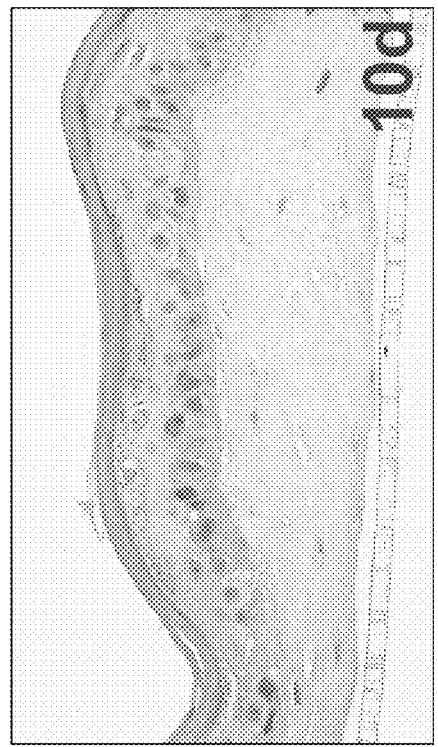
Figure 20C:
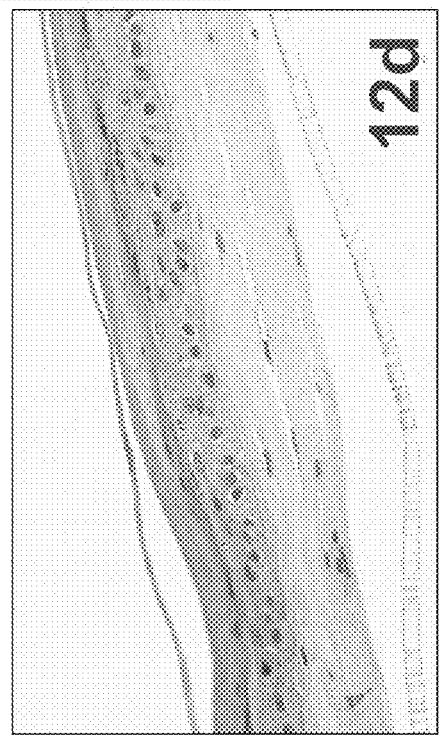

FIGS. 20A-C are microscopy images depicting H & E staining of organotypic skin equivalents (established as described in FIG. 18) grown for 7 (FIG. 20A), 10 (FIG. 20B) and 12 (FIG. 20C) days. Note the formation of all epidermal layers, the normal cornication taking place at 10 days and the desquamation starting at 12 days.

Figure 21:
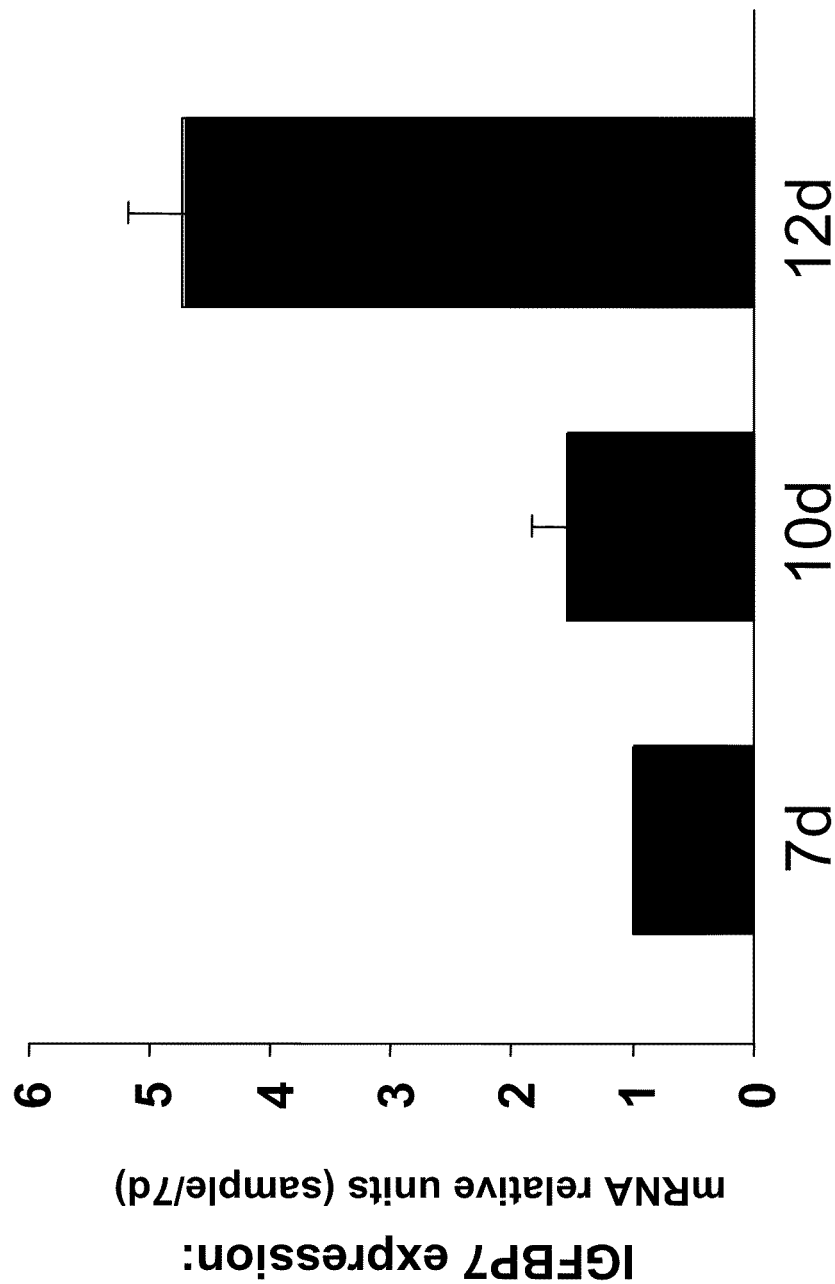

FIG. 21 is a histogram depicting IGFBP7 mRNA expression during the formation of 3-dimensional epidermis in vitro. "d"=day; Note the increase in IGFBP7 mRNA expression during skin formation.

Figure 22B:
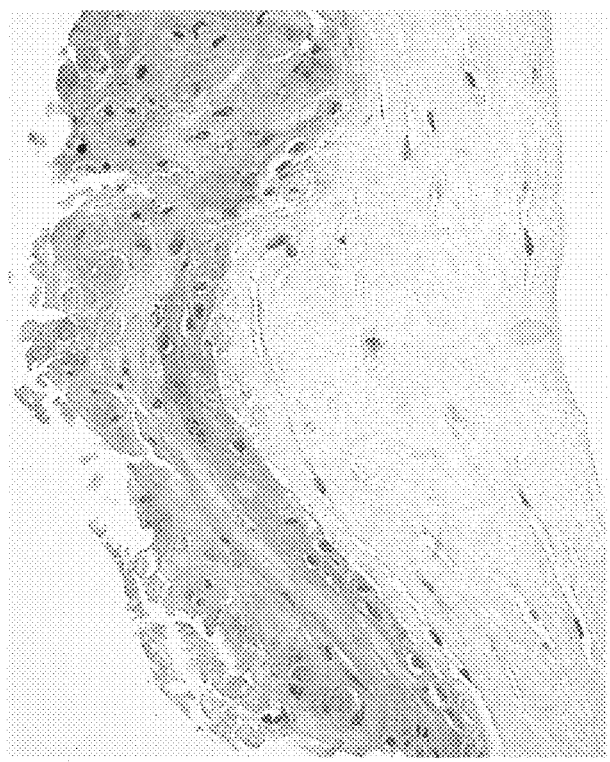
Figure 22A:
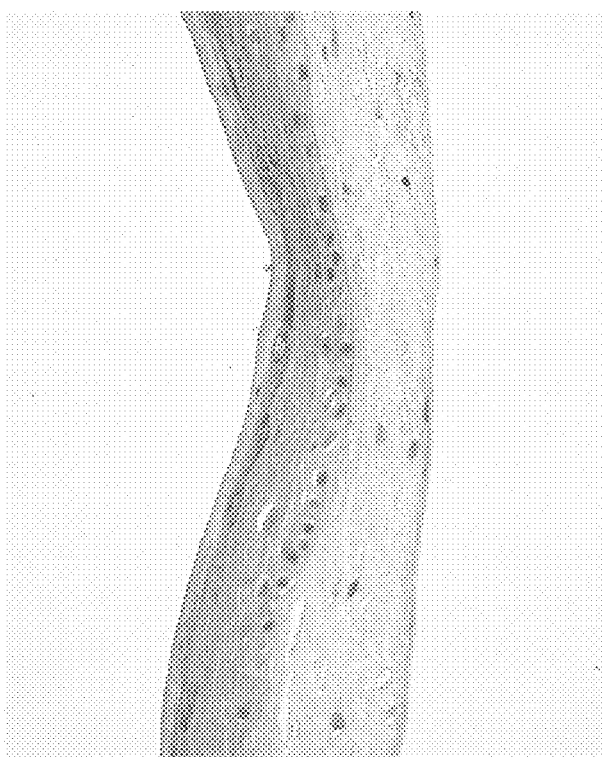

FIGS. 22A-B are microscopy images depicting H&E staining of tridimensional models transfected with control siRNA (FIG. 22A) or IGFBP7-specific siRNA (FIG. 22B), demonstrating the replication of the psoriasis phenotype using siRNA-mediated IGFBP7 down-regulation.

Figure 23:
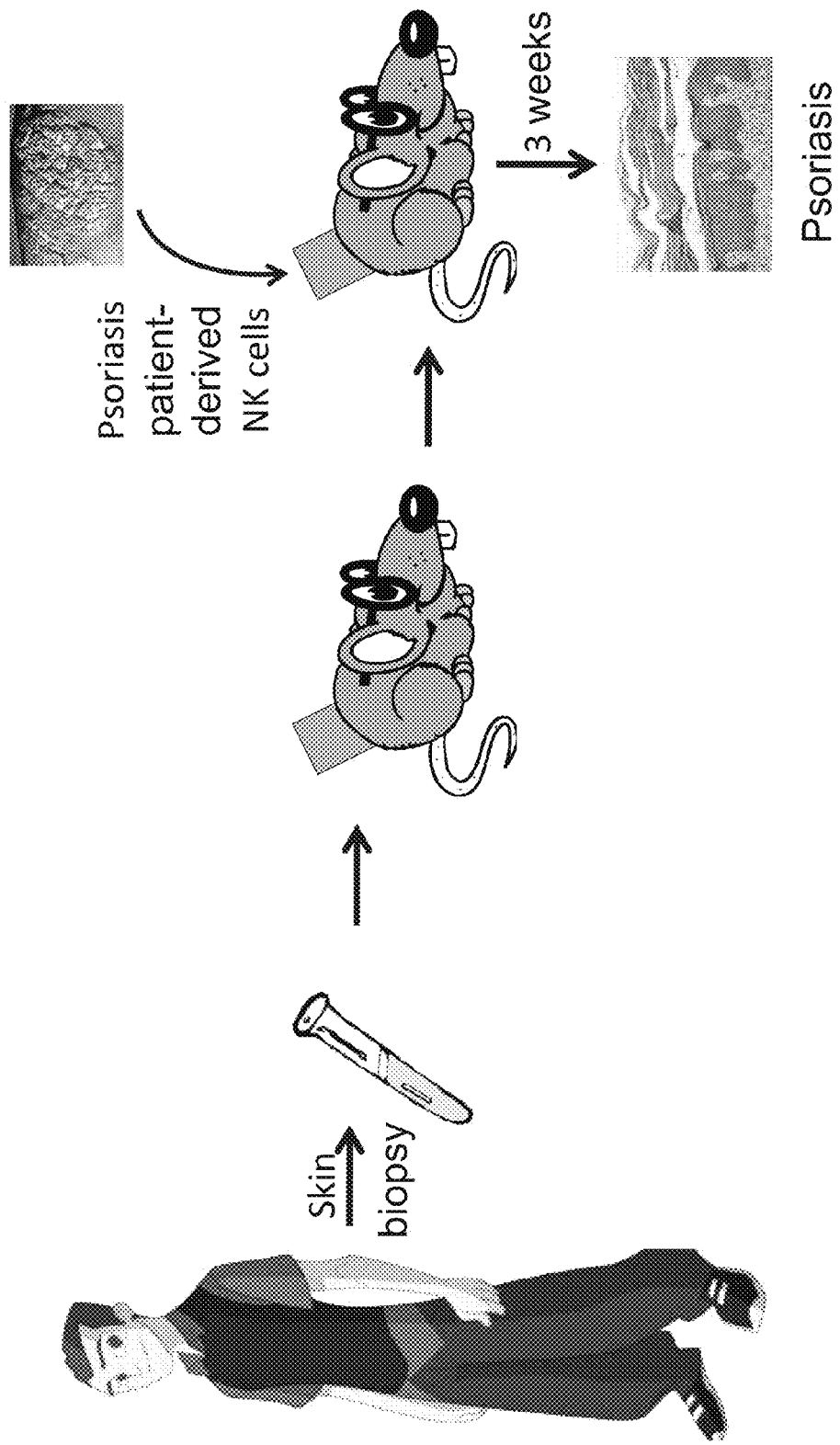

FIG. 23 is a schematic illustration of construction of an in vivo model for psoriasis. In brief, psoriasis is induced by injection of NK/T cells obtained from a psoriasis patients into normal human skin grafted onto Bg mice.

Figure 24:
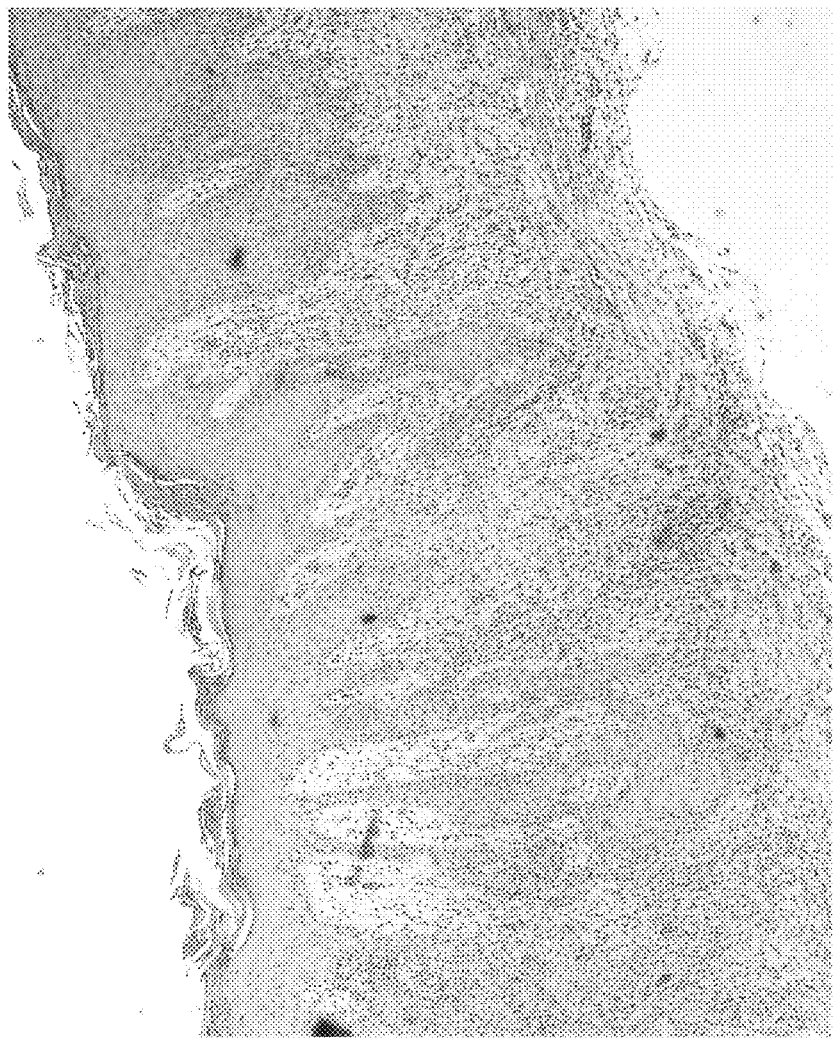

FIG. 24 is a microscopy image of Hematoxyllin & Eosine (H&E) staining of a tissue section derived from a mouse injected with PBS. Note the massive dermal infiltrate, the elongation of the rete ridges and the typical neutrophilic abscesses present in the epidermis (Magnification×40).

Figure 25:

FIG. 25 is a microscopy image of Hematoxyllin & Eosine (H&E) staining of a tissue section derived from a mouse injected with Dexamethasone. Note the normalization of the phenotype as compared with FIG. 24 (Magnification×40).

Figure 26:
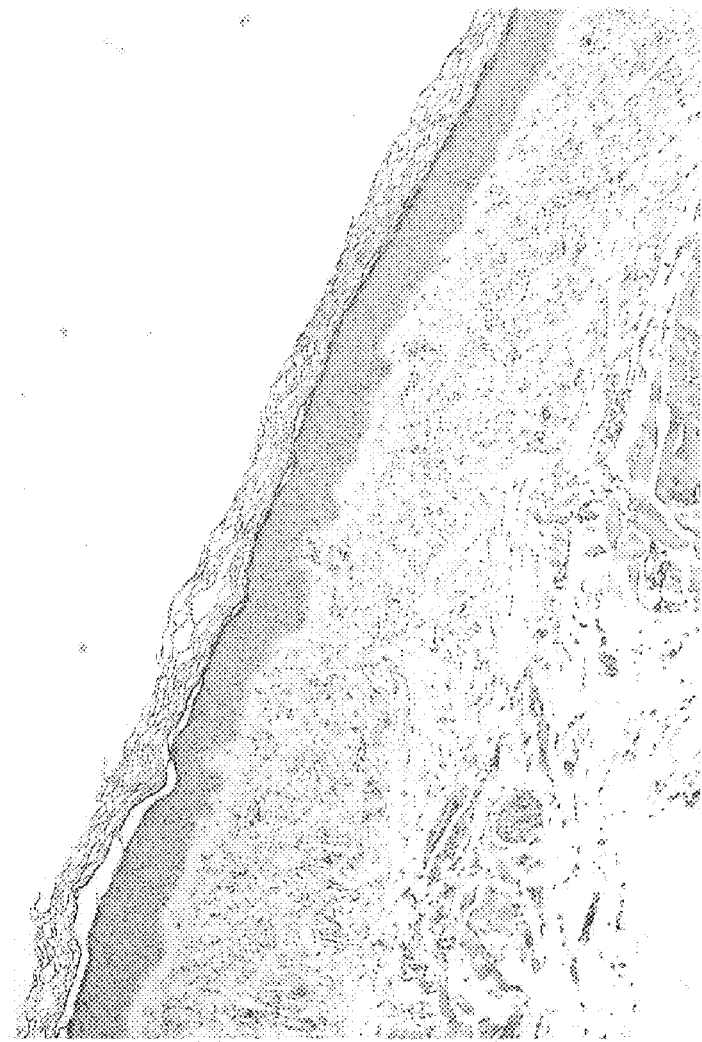

FIG. 26 is a microscopic image of Hematoxyllin & Eosine (H&E) staining of a tissue section derived from a mouse injected with IGFBP7. Note the normalization of the phenotype as compared with FIG. 24 (Magnification×40).

DESCRIPTION OF SPECIFIC EMBODIMENTS OF THE INVENTION

The present invention, in some embodiments thereof, relates to methods of regulating proliferation and/or differentiation of keratinocyets and, more particularly, but not exclusively, to methods of treating pathologies characterized by hyperproliferative keratinocytes.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The present inventors have uncovered that IGFBP7 regulates keratinocytes proliferation and differentiation.

As shown in the Examples section which follows the expression level of IGFBP7 is decreased in psoriasis tissue samples as compared to normal unaffected tissues (FIGS. 1A-D; Example 1). The present inventors have uncovered that serum stimulates downregulation of IGFBP7 expression level (FIG. 12; Example 1) and that IGFBP7 specific gene silencing (using shRNA or siRNA; FIGS. 2A-B, FIG. 8; Example 2) induces keratinocyte proliferation and viability (FIGS. 3A-F; Example 2) and decreases keratinocyte apoptosis (FIGS. 4A-C, FIGS. 14A-B; Example 2), but does not affect keratinocyte senescence (FIG. 16; Example 2). Moreover, the present inventors found that IGFBP7 is required for calcium induced keratinocyte differentiation (FIGS. 5A-C, FIGS. 9A-D, FIG. 11, Tables 3 and 4; Example 3), that IGFBP7 silencing induces phosphorylation of IRS1 and ERK in keratinocytes (FIGS. 7A-D, Example 5) and that ERK inhibition attenuates cell proliferation induced by IGFBP7 down-regulation (FIG. 17; Example 5). In addition, as shown in Example 4 of the Examples section which follows, the present inventors have uncovered that recombinant IGFBP7 inhibits proliferation and induces apoptosis in human keratinocytes (FIG. 6). Moreover, using an ex vivo model, the present inventors showed that a decrease in IGFBP7 results in a psoriasis phenotype (Example 6; FIGS. 22A-B) and that recombinant IGFBP7 cures psoriasis in a human-mouse chimeric model (FIGS. 23-26; Example 7). These results demonstrate that administration of IGFBP7 polypeptide or of a polynucleotide encoding an IGFBP7 polypeptide can induce apoptosis of keratinocyte cells and thus can be used to treat a pathology associated with hyperproliferation of keratinocytes.

According to an aspect of the present invention there is provided a method of regulating keratinocytes proliferation and differentiation the method comprising subjecting keratinocytes to an agent capable of modulating activity or expression of IGFBP7, thereby regulating keratinocytes proliferation and differentiation.

According to some embodiments of the invention regulating keratinocytes proliferation and differentiation comprises downregulating the proliferation and promoting the differentiation of keratinocytes.

According to some embodiments of the invention, downregulating the proliferation and promoting the differentiation of keratinocytes is achieved by upregulating IGFBP7 activity or expression.

As used herein the term "IGFBP7" refers to synthetic, recombinant and/or naturally occurring polynucleotide and polypeptide sequences assigned to the gene symbol IGFBP7 (insulin-like growth factor binding protein 7).

According to some embodiments of the invention, an agent capable of upregulating expression of an IGFBP7 is an exogenous polynucleotide sequence designed and constructed to express at least a functional portion of the IGFBP7. Accordingly, the exogenous polynucleotide sequence may be a DNA or RNA sequence encoding an IGFBP7 molecule, capable of inducing apoptosis of keratinocyes.

Non-limiting examples of IGFBP7 polynucleotide sequences include GenBank Accession No. NM_001553.1 (SEQ ID NO:1), nucleotides 57897244-57976539 (complement) of GenBank Accession No. NC_000004.11, nucleotides 5237126-5316421 (complement) of GenBank Accession No. NT_022853.15, nucleotides 55402267-55481286 (complement) of Accession No. AC_000047.1 (Celera), nucleotides 5227241-5306260 (complement) of GenBank Accession No. NW_922162.1 (Celera), nucleotides 53850817-53930078 (complement) of GenBank Accession No. AC_000136.1 (HuRef), nucleotides 5248335-5327596 (complement) of GenBank Accession No. NW_001838913.1 (HuRef).

IGFBP7 have been cloned from human, rat and mouse sources. Table 1 provides nucleic acid and polypeptide sequences of IGFBP7 which can be used according to some embodiments of the invention.

TABLE 1

Table 1: Provided are exemplary sequences of IGFBP7 (insulin-like growth factor binding protein 7) from various species and the percent similarity to human IGFBP7 sequences.

| Organism | Gene | % similarity to human IGFBP7 | NCBI accessions |
|---|---|---|---|
| Dog (*Canis familiaris*) | IGFBP7 | 95.04(n) 93.97(a) | GeneID: 608559; XM_845177.1 (SEQ ID NO: 2); XP_850270.1 (SEQ ID NO: 3); |

TABLE 1-continued

Table 1: Provided are exemplary sequences of IGFBP7 (insulin-like growth factor binding protein 7) from various species and the percent similarity to human IGFBP7 sequences.

| Organism | Gene | % similarity to human IGFBP7 | NCBI accessions |
|---|---|---|---|
| Chimpanzee (*Pan troglodytes*) | IGFBP7 | 99.43(n) 100(a) | GeneID: 461304; XM_517274.2 (SEQ ID NO: 4); XP_517274.2 (SEQ ID NO: 5); |
| Cow (*Bos taurus*) | IGFBP7 | 95.39(n) 95.74(a) | GeneID: 616368; NM_001102300.1 (SEQ ID NO: 6); NP_001095770.1 (SEQ ID NO: 7); |
| Rat (*Rattus norvegicus*) | Igfbp7 | 91.22(n) 91.1(a) | GeneID: 289560 NM_001013048.1 (SEQ ID NO: 8); NP_001013066.1 (SEQ ID NO: 9); |
| Mouse (*Mus musculus*) | Igfbp7 | 90.87(n) 90.75(a) | GeneID: 29817; NM_008048.2 (SEQ ID NO: 10); NP_032074.2 (SEQ ID NO: 11); |

"n" = nucleic acid sequence;
"a" = amino acid sequences.

Thus, coding sequences information for IGFBP7 is available from several databases including the GenBank database available through Hypertext Transfer Protocol://World Wide Web (dot) ncbi (dot) nlm (dot) nih (dot) gov/.

According to some embodiments of the invention, an agent capable of upregulating expression of an IGFBP7 is a polypeptide comprising at least the functional portion of IGFBP7.

Non-limiting examples of naturally occurring IGFBP7 polypeptide sequences include GenBank Accession Nos. NP_001544.1 (SEQ ID NO:12), CCDS3512.1 (SEQ ID NO:13), Q16270 (SEQ ID NO:14), EAX05521.1 (SEQ ID NO:15), EAX05520.1 (SEQ ID NO:16), AAX29723.1 (SEQ ID NO:17), AAX42962.1 (SEQ ID NO:18), AAX36927.1 (SEQ ID NO:19), and AAX36528.1 (SEQ ID NO:20).

The phrase "functional portion" as used herein refers to part of the IGFBP7 protein (i.e., a polypeptide) which exhibits functional properties of the secreted polypeptide, such as induction of apoptosis in keratinocytes and/or inhibition of keratinocyte proliferation. Assays, as described in, for example, Examples 2-7 hereinbelow may be employed to determine whether a given portion of the IGFBP7 protein is a functional portion as hereindescribed.

Methods of qualifying polypeptides which include the functional portion of IGFBP7 include in vitro assays (e.g., apoptosis assays, cell viability assay, proliferation assays performed using primary keratinocytes or keratinocytes cell lines), ex vivo assays (e.g., apoptosis assays, cell viability assay, proliferation assays performed on primary keratinocyte cultures obtained from a biopsy of hyperproliferative keratinocytes or on a tridimensional skin model as described in the Examples section) and in vivo assays (using animal models for pathologies characterized by hyperproliferative keratinocytes, by monitoring the effect of the IGFBP7 on tissue morphology using histological and immunological detection methods e.g., as described in the Examples section).

As mentioned, IGFBP7 can be a synthetic polypeptide.

The term "polypeptide" as used herein encompasses native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N(CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH=CH—), retro amide bonds (—NH—CO—), peptide derivatives (—N(R)—CH2-CO—), wherein R is the "normal" side chain, naturally presented on the carbon atom.

These modifications can occur at any of the bonds along the peptide chain and even at several (2-3) at the same time.

Natural aromatic amino acids, Trp, Tyr and Phe, may be substituted for synthetic non-natural acid such as TIC, naphthylelanine (Nol), ring-methylated derivatives of Phe, halogenated derivatives of Phe or o-methyl-Tyr.

In addition to the above, the peptides of the present invention may also include one or more modified amino acids or one or more non-amino acid monomers (e.g. fatty acids, complex carbohydrates etc).

The term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

The peptides of the present invention are preferably utilized in a linear form, although it will be appreciated that in cases where cyclicization does not severely interfere with peptide characteristics, cyclic forms of the peptide can also be utilized.

Since the present peptides are preferably utilized in therapeutics or diagnostics which require the peptides to be in soluble form, the peptides of the present invention preferably include one or more non-natural or natural polar amino acids, including but not limited to serine and threonine which are capable of increasing peptide solubility due to their hydroxyl-containing side chain.

The peptides of the present invention may be synthesized by any techniques that are known to those skilled in the art of peptide synthesis. For solid phase peptide synthesis, a summary of the many techniques may be found in J. M. Stewart and J. D. Young, Solid Phase Peptide Synthesis, W.H. Freeman Co. (San Francisco), 1963 and J. Meienhofer, Hormonal Proteins and Peptides, vol. 2, p. 46, Academic Press (New York), 1973. For classical solution synthesis see G. Schroder and K. Lupke, The Peptides, vol. 1, Academic Press (New York), 1965.

In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid can then either be attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final peptide compound. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide and so forth. Further description of peptide synthesis is disclosed in U.S. Pat. No. 6,472,505.

A preferred method of preparing the peptide compounds of the present invention involves solid phase peptide synthesis.

Large scale peptide synthesis is described by Andersson Biopolymers 2000; 55(3):227-50.

IGFBP7 can be also prepared using recombinant techniques.

For example, recombinant human IGFBP7 is available from various commercial sources such as AbDSerotec (Kidlington OXON, UK) Catalogue No. PHP178; Cell Sciences® (Canton, Mass., USA) Catalogue No. CR1511B; R&D systems Inc. (Minneapolis, Minn.); Abcam Inc. (Cambridge, Mass., USA) Catalogue No. ab50195.

To express exogenous IGFBP7 in mammalian cells, a polynucleotide sequence encoding an IGFBP7 (e.g., a polynucleotide sequence as provided above) is preferably ligated into a nucleic acid construct suitable for mammalian cell expression. Such a nucleic acid construct includes a promoter sequence for directing transcription of the polynucleotide sequence in the cell in a constitutive, tissue specific or inducible manner.

It will be appreciated that the nucleic acid construct of the present invention can also utilize polynucleotides encoding IGFBP7 homologues which exhibit the desired activity (i.e., induction of keratinocytes apoptotic activity). Such homologues can be, for example, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to the IGFBP7 polypeptide, as determined using the BestFit software of the Wisconsin sequence analysis package, utilizing the Smith and Waterman algorithm, where gap weight equals 50, length weight equals 3, average match equals 10 and average mismatch equals −9.

Constitutive promoters suitable for use with the present invention are promoter sequences which are active under most environmental conditions and most types of cells such as the cytomegalovirus (CMV) and Rous sarcoma virus (RSV). Inducible promoters suitable for use with the present invention include for example the tetracycline-inducible promoter (Zabala M, et al., Cancer Res. 2004, 64(8): 2799-804).

Non-limiting examples of tissue specific promoters which can be used to direct expression of the polynucleotide of the invention into keratinocyte cells include keratinocyte specific promoters such as the K14 promoter [e.g., GenBank Accession No. U11076 (SEQ ID NO:21), GenBank Accession No. DQ343282 (SEQ ID NO:22), nucleotides 1-2334 of GenBank Accession No. AB091380 (SEQ ID NO:23) or nucleotides 1-2258 or 1-2281 of GenBank Accession No. U11076 (SEQ ID NO:21)]; type II hair-specific keratin promoter [e.g., GenBank Accession No. AY037552 (SEQ ID NO:24)]; the keratin 4 (KRT4) promoter [e.g., nucleotides 1-1040 or 1-1103 of GenBank Accession No. AF066051 (SEQ ID NO:25); nucleotides 1-925, 1-948, 1-1010 of GenBank Accession No. X97566 (SEQ ID NO:26)]; keratin K17 promoter GenBank Accession No. S81026 (SEQ ID NO:27); keratin K5 promoter GenBank Accession No. S56203 (SEQ ID NO:28); type II hair keratin 6 promoter nucleotides 1-642, 1-647 or 1-700 of GenBank Accession No. Y19211 (SEQ ID NO:29); type II hair keratin 1 promoter [nucleotides 1-500, 1-505 or 1-550 of GenBank Accession No. Y19206 (SEQ ID NO:30)]; 65 kD keratin type II promoter [nucleotides 1-437 or 1-540 of GenBank Accession No. X05418 (SEQ ID NO:31)].

The nucleic acid construct (also referred to herein as an "expression vector") of the present invention includes additional sequences which render this vector suitable for replication and integration in prokaryotes, eukaryotes, or preferably both (e.g., shuttle vectors). In addition, a typical cloning vectors may also contain a transcription and translation initiation sequence, transcription and translation terminator and a polyadenylation signal. By way of example, such constructs will typically include a 5' LTR, a tRNA binding site, a packaging signal, an origin of second-strand DNA synthesis, and a 3' LTR or a portion thereof.

The nucleic acid construct of the present invention typically includes a signal sequence for secretion of the peptide from a host cell in which it is placed. Preferably the signal sequence for this purpose is a mammalian signal sequence or the signal sequence of the polypeptide variants of the present invention.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase the efficiency of IGFBP7 mRNA translation. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for the present invention include those derived from SV40.

In addition to the elements already described, the expression vector of the present invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

The expression vector of the present invention can further include additional polynucleotide sequences that allow, for example, the translation of several proteins from a single mRNA such as an internal ribosome entry site (IRES) and sequences for genomic integration of the promoter-chimeric polypeptide.

Examples for mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by the present invention will depend on the cell type transformed. The ability to select suitable vectors according to the cell type transformed is well within the capabilities of the ordinary skilled artisan and as such no general description of selection consideration is provided herein. For example, keratinocyte cells can be targeted using the Friend-derived retroviral vector (FOCH29-NeoR) [Arango M., et al., 2005, Dermatology Online Journal 11 (2): 2; which is incorporated herein by reference in its entirety].

Recombinant viral vectors are useful for in vivo expression of IGFBP7 since they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

Various methods can be used to introduce the expression vector of the present invention into stem cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Introduction of nucleic acids by viral infection offers several advantages over other methods such as lipofection and electroporation, since higher transfection efficiency can be obtained due to the infectious nature of viruses.

Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)]. The most preferred constructs for use in gene therapy are viruses, most preferably adenoviruses, AAV, lentiviruses, or retroviruses. A viral construct such as a retroviral construct includes at least one transcriptional promoter/enhancer or locus-defining element(s), or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide from a host cell in which it is placed. Preferably the signal sequence for this purpose is a mammalian signal sequence or the signal sequence of the polypeptide variants of the present invention. Optionally, the construct may also include a signal that directs polyadenylation, as well as one or more restriction sites and a translation termination sequence. By way of example, such constructs will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

Other than containing the necessary elements for the transcription and translation of the inserted coding sequence, the expression construct of the present invention can also include sequences engineered to enhance stability, production, purification or yield of the expressed peptide. For example, the expression of a fusion protein or a cleavable fusion protein comprising the IGFBP7 protein of some embodiments of the invention and a heterologous protein can be engineered. Such a fusion protein can be designed so that the fusion protein can be readily isolated by affinity chromatography; e.g., by immobilization on a column specific for the heterologous protein. Where a cleavage site is engineered between the IGFBP7 protein and the heterologous protein, the IGFBP7 protein can be released from the chromatographic column by treatment with an appropriate enzyme or agent that disrupts the cleavage site [e.g., see Booth et al. (1988) Immunol. Lett. 19:65-70; and Gardella et al., (1990) J. Biol. Chem. 265: 15854-15859].

As mentioned hereinabove, a variety of prokaryotic or eukaryotic cells can be used as host-expression systems to express the IGFBP7 polypeptide of the invention. These include, but are not limited to, microorganisms, such as bacteria transformed with a recombinant bacteriophage DNA, plasmid DNA or cosmid DNA expression vector containing the coding sequence; yeast transformed with recombinant yeast expression vectors containing the coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the coding sequence. Mammalian expression systems can also be used to express the polypeptides of the present invention.

Examples of bacterial constructs include the pET series of E. coli expression vectors [Studier et al. (1990) Methods in Enzymol. 185:60-89).

In yeast, a number of vectors containing constitutive or inducible promoters can be used, as disclosed in U.S. Pat. No. 5,932,447. Alternatively, vectors can be used which promote integration of foreign DNA sequences into the yeast chromosome.

In cases where plant expression vectors are used, the expression of the coding sequence can be driven by a number of promoters. For example, viral promoters such as the 35S RNA and 19S RNA promoters of CaMV [Brisson et al. (1984) Nature 310:511-514], or the coat protein promoter to TMV [Takamatsu et al. (1987) EMBO J. 6:307-311] can be used. Alternatively, plant promoters such as the small subunit of RUBISCO [Coruzzi et al. (1984) EMBO J. 3:1671-1680 and Brogli et al., (1984) Science 224:838-843] or heat shock promoters, e.g., soybean hsp17.5-E or hsp17.3-B [Gurley et al. (1986) Mol. Cell. Biol. 6:559-565] can be used. These constructs can be introduced into plant cells using Ti plasmid, Ri plasmid, plant viral vectors, direct DNA transformation, microinjection, electroporation and other techniques well known to the skilled artisan. See, for example, Weissbach & Weissbach, 1988, Methods for Plant Molecular Biology, Academic Press, NY, Section VIII, pp 421-463.

Other expression systems such as insects and mammalian host cell systems which are well known in the art and are further described hereinbelow can also be used by the present invention.

Recovery of the recombinant polypeptide is effected following an appropriate time in culture. The phrase "recovering the recombinant polypeptide" refers to collecting the whole fermentation medium containing the polypeptide and need not imply additional steps of separation or purification. Not withstanding the above, polypeptides of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

According to some embodiments of the invention down-regulating the proliferation and promoting the differentiation is for treating a pathology characterized by hyperproliferation of keratinocytes (hyperproliferative keratinocytes), e.g., epidermal hyperplasia such as occurs in psoriasis.

Thus, according to an aspect of some embodiments of the invention there is provided a method of treating a pathology characterized by hyperproliferative keratinocytes comprising administering to a subject in need thereof a therapeutically effective amount of an IGFBP7 polypeptide or a nucleic acid sequence encoding the IGFBP7 polypeptide, thereby treating the pathology characterized by the hyperproliferative keratinocytes.

The term "treating" refers to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

As used herein, the term "subject" includes mammals, preferably human beings at any age which suffer from the pathology.

As used herein the phrase "hyperproliferative keratinocytes" refers to keratinocytes that proliferate to an extent which increases the density of keratinocytes in a tissue (e.g., skin) and/or having a higher proliferation rate in a tissue as compared to keratinocytes of a non-affected (e.g., healthy) tissue, e.g., a tissue of a healthy subject.

As used herein the term "keratinocyte" refers to a cell that produces keratin and which forms the major constituent of the epidermis (constituting about 95% of the epidermis cell population).

Non-limiting examples of keratinocyte containing tissues include skin, scalp, mucosal lining of the upper digestive and respiratory tracts, and of the lower genitourinary and gastrintestinal tracts.

According to some embodiments of the invention, the phrase "hyperproliferative keratinocytes" refers to "epidermal hyperplasia", an abnormal increase in epidermis cells (excessive keratinocyte proliferation), excluding tumor formation.

Epidermal hyperplasia, which leads to expansion of the epidermis, in association with epidermal shedding are the major manifestation of psoriasis. Epidermal hyperplasia also occurs under physiological conditions (e.g., during wound-healing) and is a consequence in many individuals of topical treatment with all-trans retinoic acid (RA) or its precursor, all-trans retinol.

As used herein the phrase "a pathology characterized by hyperproliferative keratinocytes" refers to any disease, disorder or condition which is characterized by or results from hyperproliferative keratinocytes.

Non-limiting examples of pathologies which are characterized by hyperproliferative keratinocytes include psoriasis, lichen planus, pityriasis rubra pilaris (PRP), papulosquamous disease, dermatitis and lichen simplex chronicus.

According to some embodiments of the invention, the pathology characterized by the hyperproliferative keratinocytes is psoriasis.

As used herein the term "psoriasis" refers to adult and childhood psoriasis.

As used herein the term "lichen planus" refers to a chronic mucocutaneous disease that affects the skin and the oral mucosa, and presents itself in the form of papules, lesions or rashes. According to some embodiments of the invention, the term "lichen planus" encompasses annular lichen planus, linear lichen planus, hypertrophic lichen planus, atrophic lichen planus, vesiculobullous lichen planus, ulcerative lichen planus, follicular lichen planus, actinic lichen planus, lichen planus pigmentosus, site of involvement, lichen planus of the palms and soles (palmoplantar lichen planus), mucosal lichen planus, lichen planus of the nails, lichen planus of the scalp, inverse lichen planus, drug-induced lichen planus, lupus erythematosus-lichen planus overlap syndrome, lichen planus pemphigoides, keratosis lichenoides chronica, lichenoid reaction of graft-versus-host disease, lichenoid keratosis, and/or lichenoid dermatitis.

As used herein the term "pityriasis rubra pilaris (PRP)" refers to a group of chronic disorders characterized by reddish orange, scaling plaques and keratotic follicular papules.

As used herein the term "papulosquamous" disease or disorder refers to a condition which presents with both papules and scales, or both scaly papules and plaques.

As used herein the term "dermatitis" encompasses different types of inflammation of the skin, e.g. rash, which usually have in common an allergic or irritant reaction to specific agents or allergens. The term may be used to refer to eczema, which is also known as dermatitis eczema or eczematous dermatitis. According to some embodiments of the invention the term dermatitis refers to atopic dermatitis and contact dermatitis.

As used herein the term "lichen simplex chronicus" a skin disorder characterized by chronic itching and scratching which usually causes thick, leathery, brownish skin.

As used herein the term "administering" refers to any means of administration of the active agent to the subject and include systemic administration (e.g., intravenous, orally) and/or local administration (e.g., to the skin, e.g., topical administration).

Herein the term "active ingredient" refers to the IGFBP7 polypeptide or a functional portion thereof and/or a polynucleotide encoding IGFBP7 polypeptide or encoding a functional portion thereof, accountable for the biological effect (e.g., inducing apoptosis and/or inhibiting proliferation of keratinocytes).

The active agent can be administered to the individual per se or as part of a pharmaceutical composition which also includes a physiologically acceptable carrier. The purpose of a pharmaceutical composition is to facilitate administration of the active ingredient to an organism.

As used herein a "pharmaceutical composition" refers to a preparation of one or more of the active ingredients described herein with other chemical components such as physiologically suitable carriers and excipients.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include topical administration [for example, using gels, liquid sprays and patches (which comprise the active agent and which are applied on the outer surface of the skin)], subcutaneous administration, intradermal administration (e.g., by intradermal injections), intralesional administration (e.g., using a patch, gel, needle), systemic administration such as by oral, rectal, transmucosal, especially transnasal, intestinal or parenteral delivery, including intramuscular, and intramedullary injections as well as intrathecal, direct intraventricular, intracardiac, e.g., into the right or left ventricular cavity, into the common coronary artery, intravenous, intraperitoneal, intranasal, or intraocular injections.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

According to specific embodiments, administration is effected topically.

According to some embodiments of the invention, administration of the active agent into the skin of the subject is performed non-invasively, e.g., using a lotion, ointment, cream, gel, a liquid spray or a patch comprising the active agent, which are applied onto the skin of the subject.

The carrier utilized in the compositions of the invention can be in a wide variety of forms. These include emulsion carriers, including, but not limited to, oil-in-water, water-in-oil, water-in-oil-in-water, and oil-in-water-in-silicone emulsions, a cream, an ointment, an aqueous solution, a lotion or an aerosol. As will be understood by the skilled artisan, a given component will distribute primarily into either the water or oil/silicone phase, depending on the water solubility/dispersibility of the component in the composition.

Emulsions according to the present invention generally contain a pharmaceutically effective amount of an agent disclosed herein and a lipid or oil. Lipids and oils may be derived from animals, plants, or petroleum and may be natural or synthetic (i.e., man-made). Preferred emulsions also contain a humectant, such as glycerin. Emulsions will preferably further contain from about 1% to about 10%, more preferably from about 2% to about 5%, of an emulsifier, based on the weight of the carrier. Emulsifiers may be nonionic, anionic or cationic. Suitable emulsifiers are described in, for example, U.S. Pat. No. 3,755,560, issued to Dickert, et al. Aug. 28, 1973; U.S. Pat. No. 4,421,769, issued to Dixon, et al., Dec. 20, 1983; and McCutcheon's Detergents and Emulsifiers, North American Edition, pages 317-324 (1986).

The emulsion may also contain an anti-foaming agent to minimize foaming upon application to the keratinous tissue. Anti-foaming agents include high molecular weight silicones and other materials well known in the art for such use.

Suitable emulsions may have a wide range of viscosities, depending on the desired product form. Exemplary low viscosity emulsions, which are preferred, have a viscosity of about 50 centistokes or less, more preferably about 10 centistokes or less, most preferably about 5 centistokes or less. The emulsion may also contain an anti-foaming agent to minimize foaming upon application to the keratinous tissue. Anti-foaming agents include high molecular weight silicones and other materials well known in the art for such use.

One type of emulsion is a water-in-silicone emulsion. Water-in-silicone emulsions contain a continuous silicone phase and a dispersed aqueous phase. Preferred water-in-silicone emulsions of the present invention comprise from about 1% to about 60%, preferably from about 5% to about 40%, more preferably from about 10% to about 20%, by weight of a continuous silicone phase. The continuous silicone phase exists as an external phase that contains or surrounds the discontinuous aqueous phase described hereinafter.

The continuous silicone phase may contain a polyorganosiloxane oil. A preferred water-in-silicone emulsion system is formulated to provide an oxidatively stable vehicle for delivery of a pharmaceutically effective amount of an agent disclosed herein. The continuous silicone phase of these preferred emulsions comprises between about 50% and about 99.9% by weight of organopolysiloxane oil and less than about 50% by weight of a non-silicone oil. In an especially preferred embodiment, the continuous silicone phase comprises at least about 50%, preferably from about 60% to about 99.9%, more preferably from about 70% to about 99.9%, and even more preferably from about 80% to about 99.9%, polyorganosiloxane oil by weight of the continuous silicone phase, and up to about 50% non-silicone oils, preferably less about 40%, more preferably less than about 30%, even more preferably less than about 10%, and most preferably less than about 2%, by weight of the continuous silicone phase. These useful emulsion systems may provide more oxidative stability over extended periods of time than comparable water-in-oil emulsions containing lower concentrations of the polyorganosiloxane oil. Concentrations of non-silicone oils in the continuous silicone phase are minimized or avoided altogether so as to possibly further enhance oxidative stability of the active compound of the invention in the compositions. Water-in-silicone emulsions of this type are described in U.S. Pat. No. 5,691,380 to Mason et al., issued Nov. 25, 1997.

The organopolysiloxane oil for use in the composition may be volatile, non-volatile, or a mixture of volatile and non-volatile silicones. The term "nonvolatile" as used in this context refers to those silicones that are liquid under ambient conditions and have a flash point (under one atmospheric of pressure) of or greater than about 100 degrees Celsius. The term "volatile" as used in this context refers to all other silicone oils. Suitable organopolysiloxanes can be selected from a wide variety of silicones spanning a broad range of volatilities and viscosities. Examples of suitable organopolysiloxane oils include polyalkylsiloxanes, cyclic polyalkylsiloxanes, and polyalkylarylsiloxanes, which are known to those skilled in the art and commercially available.

The continuous silicone phase may contain one or more non-silicone oils. Concentrations of non-silicone oils in the continuous silicone phase are preferably minimized or avoided altogether so as to further enhance oxidative stability of the pharmaceutically effective agent in the compositions. Suitable non-silicone oils have a melting point of about 25° C. or less under about one atmosphere of pressure. Examples of non-silicone oils suitable for use in the continuous silicone phase are those well known in the chemical arts in topical personal care products in the form of water-in-oil emulsions, e.g., mineral oil, vegetable oils, synthetic oils, semisynthetic oils, etc.

Useful topical compositions of the present invention comprise from about 30% to about 90%, more preferably from about 50% to about 85%, and most preferably from about 70% to about 80% of a dispersed aqueous phase. The term "dispersed phase" is well-known to one skilled in the art it implies that the phase exists as small particles or droplets that are suspended in and surrounded by a continuous phase. The dispersed phase is also known as the internal or discontinuous phase. The dispersed aqueous phase is a dispersion of small aqueous particles or droplets suspended in and surrounded by the continuous silicone phase described hereinbefore. The aqueous phase can be water, or a combination of water and one or more water soluble or dispersible ingredients. Non-limiting examples of such optional ingredients include thickeners, acids, bases, salts, chelants, gums, water-soluble or dispersible alcohols and polyols, buffers, preservatives, sunscreening agents, colorings, and the like.

The topical compositions of the present invention typically comprise from about 25% to about 90%, preferably from about 40% to about 80%, more preferably from about 60% to about 80%, water in the dispersed aqueous phase by weight of the composition.

The water-in-silicone emulsions of the present invention preferably comprise an emulsifier. In a preferred embodiment, the composition contains from about 0.1% to about 10% emulsifier, more preferably from about 0.5% to about 7.5%, most preferably from about 1% to about 5%, emulsifier by weight of the composition. The emulsifier helps disperse and suspend the aqueous phase within the continuous silicone phase.

A wide variety of emulsifying agents can be employed herein to form the preferred water-in-silicone emulsion. Known or conventional emulsifying agents can be used in the composition, provided that the selected emulsifying agent is chemically and physically compatible with essential components of the composition, and provides the desired dispersion characteristics. Suitable emulsifiers include silicone emulsifiers, e.g., organically modified organopolysiloxanes, also known to those skilled in the art as silicone surfactants, non-silicon-containing emulsifiers, and mixtures thereof, known by those skilled in the art for use in topical personal care products.

Useful emulsifiers include a wide variety of silicone emulsifiers. These silicone emulsifiers are typically organically modified organopolysiloxanes, also known to those skilled in the art as silicone surfactants. Suitable emulsifiers are described, for example, in McCutcheon's, Detergents and Emulsifiers, North American Edition (1986), published by Allured Publishing Corporation; U.S. Pat. No. 5,011,681 to Ciotti et al., issued Apr. 30, 1991; U.S. Pat. No. 4,421,769 to Dixon et al., issued Dec. 20, 1983; and U.S. Pat. No. 3,755,560 to Dickert et al., issued Aug. 28, 1973.

Other preferred topical carriers include oil-in-water emulsions, having a continuous aqueous phase and a hydrophobic, water-insoluble phase ("oil phase") dispersed therein.

Examples of suitable carriers comprising oil-in-water emulsions are described in U.S. Pat. No. 5,073,371 to Turner, D. J. et al., issued Dec. 17, 1991, and U.S. Pat. No. 5,073,372, to Turner, D. J. et al., issued Dec. 17, 1991. An especially preferred oil-in-water emulsion, containing a structuring agent, hydrophilic surfactant and water, is described in detail hereinafter.

A preferred oil-in-water emulsion comprises a structuring agent to assist in the formation of a liquid crystalline gel network structure. Without being limited by theory, it is believed that the structuring agent assists in providing rheological characteristics to the composition which contribute to the stability of the composition. The structuring agent may also function as an emulsifier or surfactant. Preferred compositions of this invention comprise from about 0.5% to about 20%, more preferably from about 1% to about 10%, most preferably from about 1% to about 5%, by weight of the composition, of a structuring agent. The preferred structuring agents of the present invention are selected from the group consisting of stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

A wide variety of anionic surfactants are also useful herein. See, e.g., U.S. Pat. No. 3,929,678, to Laughlin et al., issued Dec. 30, 1975. In addition, amphoteric and zwitterionic surfactants are also useful herein.

The preferred oil-in-water emulsions comprise from about 0.05% to about 10%, preferably from about 1% to about 6%, and more preferably from about 1% to about 3% of at least one hydrophilic surfactant which can disperse the hydrophobic materials in the water phase (percentages by weight of the topical carrier). The surfactant, at a minimum, must be hydrophilic enough to disperse in water. Suitable surfactants include any of a wide variety of known cationic, anionic, zwitterionic, and amphoteric surfactants. See, McCutcheon's. Detergents and Emulsifiers, North American Edition (1986), published by Allured Publishing Corporation; U.S. Pat. No. 5,011,681 to Ciotti et al., issued Apr. 30, 1991; U.S. Pat. No. 4,421,769 to Dixon et al. issued to Dec. 20, 1983; and U.S. Pat. No. 3,755,560. The exact surfactant chosen depends upon the pH of the composition and the other components present. Preferred are cationic surfactants, especially dialkyl quaternary ammonium compounds, examples of which are described in U.S. Pat. No. 5,151,209 to McCall et al. issued to Sep. 29, 1992; U.S. Pat. No. 5,151,210 to Steuri et al., issued to Sep. 29, 1992; U.S. Pat. No. 5,120,532; U.S. Pat. No. 4,387,090; U.S. Pat. No. 3,155,591; U.S. Pat. No. 3,929,678; U.S. Pat. No. 3,959,461; McCutcheon's, Detergents & Emulsifiers (North American edition 1979) M.C. Publishing Co.; and Schwartz, et al., Surface Active Agents, Their chemistry and Technology, New York: Interscience Publishers, 1949.

Alternatively, other useful cationic emulsifiers include amino-amides. Nonlimiting examples of these cationic emulsifiers include stearamidopropyl PG-dimonium chloride phosphate, behenamidopropyl PG dimonium chloride, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

The preferred oil-in-water emulsion comprises from about 25% to about 98%, preferably from about 65% to about 95%, more preferably from about 70% to about 90% water by weight of the topical carrier.

The pharmaceutical or cosmetic composition of the present invention can be formulated in any of a variety of forms utilized by the pharmaceutical or cosmetic industry for skin application including solutions, lotions, sprays, creams, ointments, salves, gels, etc., as described below.

Preferably, the pharmaceutical or cosmetic composition of the present invention is formulated viscous enough to remain on the treated skin area, does not readily evaporate, and/or is not easily removed by rinsing with water, but rather is removable with the aid of soaps, cleansers and/or shampoos.

Methods for preparing compositions having such properties are well known to those skilled in the art, and are described in detail in Remington's Pharmaceutical Sciences, 1990 (supra); and Pharmaceutical Dosage Forms and Drug Delivery Systems, 6th ed., Williams & Wilkins (1995).

The topical compositions of the subject invention, including but not limited to lotions and creams, may comprise a dermatologically acceptable emollient. Such compositions preferably contain from about 2% to about 50% of the emollient. As used herein, "emollient" refers to a material useful for the prevention or relief of dryness, as well as for the protection of the skin. A wide variety of suitable emollients are known and may be used herein. See, e.g., Sagarin, Cosmetics, Science and Technology, 2nd Edition, Vol. 1, pp. 3243 (1972), which contains numerous examples of materials suitable as an emollient. A preferred emollient is glycerin. Glycerin is preferably used in an amount of from or about 0.001 to or about 20%, more preferably from or about 0.01 to or about 10%, most preferably from or about 0.1 to or about 5%, e.g., 3%.

Lotions and creams according to the present invention generally comprise a solution carrier system and one or more emollients. Lotions typically comprise from about 1% to about 20%, preferably from about 5% to about 10% of emollient; from about 50% to about 90%, preferably from about 60% to about 80% water; and a pharmaceutically effective amount of an agent described herein. A cream typically comprises from about 5% to about 50%, preferably from about 10% to about 20% of emollient; from about 45% to about 85%, preferably from about 50% to about 75% water; and a pharmaceutically effective amount of an agent described herein.

The topically applied pharmaceutical or cosmetic composition of the present invention may also include additional components which are added, for example, in order to enrich the cosmetic compositions with fragrance and skin nutrition factors.

Such components are selected suitable for use on human keratinous tissue without inducing toxicity, incompatibility, instability, allergic response, and the like within the scope of sound medical judgment. In addition, such optional components are useful provided that they do not unacceptably alter the benefits of the active compounds of the invention.

The CTFA Cosmetic Ingredient Handbook, Second Edition (1992) describes a wide variety of non-limiting cosmetic ingredients commonly used in the skin care industry, which are suitable for use in the compositions of the present invention. Examples of these ingredient classes include: abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, antifoaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin-conditioning agents (e.g., humectants, including miscellaneous and occlusive), skin soothing and/or healing agents (e.g., panthenol and derivatives (e.g., ethyl panthenol), aloe vera, pantothenic acid and its derivatives, allantoin, bisabolol, and dipotassium glycyffhizinate), skin treating agents, thickeners, and vitamins and derivatives thereof.

The pharmaceutical or cosmetic composition of the present invention can be applied directly to the skin. Alternatively, it can be delivered via normal skin application by various transdermal drug delivery systems which are known in the art, such as transdermal patches that release the composition into the skin in a time released manner. Other drug delivery systems known in the arts include pressurized aerosol bottle, iontophoresis or sonophoresis. Iontophoresis is employed to increase skin permeability and facilitate transdermal delivery. U.S. Pat. Nos. 5,667,487 and 5,658,247 discloses an ionosonic apparatus suitable for the ultrasonic-iontophoretically mediated transport of therapeutic agents across the skin. Alternatively, or in addition, liposomes or micelles may also be employed as a delivery vehicle.

There are two main types of skin patches which can be used to administer the active agent into the skin of a subject. These are the reservoir type patch and the matrix type patch. The reservoir patch usually contains a structure filled with a solid drug (active agent) and a dilute solution, or a highly concentrated drug solution within a polymer matrix and is surrounded by a film or membrane of rate-controlling material. The matrix patch contains a drug and a polymer which form a homogenous system from which the drug is released by diffusion into the external environment. It should be noted that as the release continues, its rate in the matrix type patch usually decreases since the active agent has a progressively longer distance and therefore requires a longer diffusion time to release. For further details and examples of transdermal drug delivery see Prausnitz M R., et al., 2004. Nature Reviews, 3:115-124; Scheindlin S., 2004. Transdermal drug delivery: Past, present, future. Molecular Interventions. Vol. 4:308-312; Prausnitz M R and Langer R., 2008, Nature Biotechnology. 26:1261-1268; Tanner T, and Marks R, 2008, Delivery drugs by transdermal route: review and comment. Skin Research and Technology, 14: 249-260; each of which is hereby incorporated by reference in its entirety).

A non-limiting example of an epicutaneous drug delivery patch, which can be used to administer the active agent into the skin according to the teachings of the invention, is described in Senti G., et al., 2009, J Allergy Clin Immunol. September 4. [Epub ahead of print], which is hereby incorporated by reference in its entirety).

According to some embodiments of the invention, administering the active agent to the skin is performed using a reservoir type patch.

Administering into an intact skin can be performed using an occlusive patch with semi-solid reservoir and a plastic backing adhesive contour and protective removable cover.

A semi-solid reservoir can be any gel, cream, ointment, emulsion, suspension, microparticles, using various excipients such as fats, oils (e.g., mineral oil, vaselin, vegetable oil or silicon oil), polymers, gelling agent, suspending agent, stabilizers, hydrophilic solvents, Propylene glycol, polyethylene glycols, stabilizing surfactants, colloids etc. and their combinations.

It should be noted that in order to increase delivery of the active agent into the skin, the active agent can be formulated with various vehicles designed to increase delivery to the epidermis or the dermis layers. Such vehicles include, but are not limited to liposomes, dendrimers, noisome, transfersome, microemulsion and solid lipid nanoparticles (for further details see Cevc, G. Transfersomes, liposomes and other lipid suspensions on the skin: permeation enhancement, vesicle penetration, and transdermal drug delivery. Crit. Rev. Ther. Drug Carrier Syst. 13, 257-388 (1996), which is hereby incorporated by reference in its entirety; Kogan A, Garti N. Microemulsions as transdermal drug delivery vehicles. Adv Colloid Interface Sci 2006; 123-126:369-385, which is hereby incorporated by reference in its entirety). In addition, the active agent can be mixed with chemical enhancers such as sulphoxides, azones, glycols, alkanols and terpenes which enhance delivery of active agents into the skin (for further details see Karande P, Jain A, Ergun K, Kispersky V, Mitragotri S. Design principles of chemical penetration enhancers for transdermal drug delivery. Proc Natl Acad Sci USA 2005; 102:4688-4693; Williams A C, Barry B W. Penetration enhancers. Adv Drug Deliv Rev 2004; 56:603-618; and Smith, E W.; Maibach, H I., editors. Boca Raton, Fla.: Taylor and Francis Group; 2006. Percutaneous Penetration Enhancers; each of which is hereby incorporated by reference in its entirety).

The patch may include the active agent formulated within an emulsion designed to facilitate permeabilization of drugs to the epidermis or the dermis. For example, the patch may comprise the active agent within an oil-in-glycerin emulsion, which is designed to facilitate permeabilization of the active agent through the stratum-corneum and into the dermis. A non-limiting example of an oil-in-glycerin emulsion suitable for delivery through the stratum-corneum into the dermis is described in US Patent Application No. 20040067244, which is hereby incorporated by reference in its entirety. Such an oil-in-glycerin emulsion exhibits a mean droplet size below one micron, and comprises a continuous glycerin phase; at least one vegetable oil comprising an internal phase; at least one emulsifying stabilizer; and at least one bioactive compound comprising at least one hydrophobic, moiety within its structure, wherein the composition facilitates permeabilization of the bioactive compound through the stratum-corneum and into the dermis.

According to some embodiments of the invention, administering the active agent to the skin is effected on a breached skin [e.g., a skin that has been permeabilized (e.g., ruptured) with an external object and the like or a lesional skin (a skin which include a lesion].

According to some embodiments of the invention, breaching of the skin is effected temporarily (e.g., performed for a pre-determined short period) and is designed to enable better permeabilization of the active ingredient into the skin.

Breaching of the skin can be performed, for example, by introducing micro-holes (e.g., microchannels) in the outer layer of the skin. Such microchannels can be formed using for example, the Radio-Frequency (RF)-Microchannel™ (TransPharma Medical™ Ltd.) technology [Hypertext Transfer Protocol://World Wide Web (dot) transpharmamedical (dot) com/technology_rf (dot) html].

Additionally or alternatively, delivery of the active agent (e.g., IGFBP7 polypeptide or polynucleotide encoding same) from the patch to the epidermis layer of the skin can be enhanced using physical enhancers known in the art such as ultrasound, ionophoresis, electroporation, magnetophoresis, microneedle and continuous mixing [see e.g., Rizwan M, Aqil M, Talegaonkar S, Azeem A, Sultana Y, Ali A. Enhanced transdermal drug delivery techniques: an extensive review of patents. Recent Pat Drug Deliv Formul. 2009; 3(2):105-24, which is hereby incorporated by reference in its entirety].

According to some embodiments of the invention, the pharmaceutical composition is formulated for intradermal injection.

The active agent can be administered into the dermal layer of the skin of the subject by an intradermal injection as described for the Mantoux C (1908) test. Briefly, the active agent can be injected intracutaneously (using for example, a 0.5-ml or 1.0 ml tuberculin syringe through a 26-gauge or 27-gauge needle). The syringe can be placed at an angle of 45 degrees to the skin, and the bevel of the needle is angled downward, facing the skin, and penetrating entirely but not deeper than the superficial layers of the skin. A volume of approximately 0.01 to 0.05 ml (e.g., about 0.02 ml) is gently injected to produce a small superficial bleb (Middleton's Allergy principles&practice, $6^{th}$ edition 2003).

According to some embodiments of the invention, the pharmaceutical composition is formulated for a liquid spray (e.g., a spray which includes the active agent in a pre-determined concentration and dosage).

According to some embodiments of the invention, the pharmaceutical composition is formulated for a gel (e.g., a gel which includes the active agent in a pre-determined concentration and dosage).

For example, for administration using a gel or a spray, a predefined area for administration of the active agent is selected and optionally bounded using an accessory equipment (see e.g., Hypertext Transfer Protocol://World Wide Web (dot) truetest (dot) com).

Since pathologies which are characterized by hyperproliferative keratinocytes such as psoriasis lesions often affect the skin of the scalp, the pharmaceutical or cosmetic composition of the present invention further includes emollients, surfactants and/or conditioners which are suitable for use on the scalp skin and hair.

The emollients include, but are not limited to, hydrocarbon oils and waxes, such as mineral oil, petrolatum, and the like, vegetable and animal oils and fats, such as olive oil, palm oil, castor oil, corn oil, soybean oil, and the like, and lanolin and its derivatives, such as lanolin, lanolin oil, lanolin wax, lanolin alcohols, and the like. Other emollients include esters of fatty acids having 10 to 20 carbon atoms, such as including myristic, stearic, isostearic, palmitic, and the like, such as methyl myristate, propyl myristate, butyl myristate, propyl stearate, propyl isostearate, propyl palmitate, and the like. Other emollients include fatty acids having 10 to 20 carbon atoms, including stearic, myristic, lauric, isostearic, palmitic, and the like. Emollients also include fatty alcohols having ten to twenty carbon atoms, such as cetyl, myristyl, lauryl, isostearyl, stearyl and the like.

Although some are water soluble, polyhydric alcohols and polyether derivatives are included as emollients, including glycols, glycerol, sorbitol, polyalkylene glycols and the like, such as propylene glycol, dipropylene glycol, polyethylene glycol 200-500, and the like. The water soluble examples are preferred.

An emulsifier/surfactant is preferably utilized when formulating the pharmaceutical or cosmetic composition of the present invention for use on hair.

Examples of surfactants include, but are not limited to, spolyoxyalkylene oxide condensation products of hydrophobic alkyl, alkene, or alkyl aromatic functional groups having a free reactive hydrogen available for condensation with hydrophilic alkylene oxide, polyethylene oxide, propylene oxide, butylene oxide, polyethylene oxide or polyethylene glycol Particularly effective are the condensation products of octylphenol with about 7 to about 13 moles of ethylene oxide, sold by the Rohm & Haas Company under their trademark TRITON 100® series products.

Other ingredients such as, fragrances, stabilizing agents, dyes, antimicrobial agents, antibacterial agents, anti agglomerates, ultraviolet radiation absorbers, and the like are also included in the composition of the present invention which is formulated for use on hair.

A conditioner agent stable to acid hydrolysis, such as a silicone compound having at least one quaternary ammonium moiety along with an ethoxylated monoquat is preferably also utilized in order to stabilize and optionally thicken the composition of the present invention which is formulated for use on hair.

An optional thickener also can be included to improve composition esthetics and facilitate application of the composition to the hair. Nonionic thickeners in an amount of 0% to about 3% by weight are preferred. Exemplary thickeners are methylcellulose, hydroxybutyl methylcellulose, hydroxypropylcellulose, hydroxypropyl methylcellulose, hydroxyethyl ethylcellulose and hydroxyethylcellulose, di(hydrogenated tallow) phthalic acid amide, crosslinked maleic anhydride-methyl vinyl ether copolymer, guar gum, xanthan gum and gum arabic.

The carrier of the conditioning composition is predominantly water, but organic solvents also can be included in order to facilitate manufacturing of the composition or to provide esthetic properties, such as viscosity control. Suitable solvents include the lower alcohols like ethyl alcohol and isopropyl alcohol; glycol ethers, like 2-butoxyethanol, ethylene glycol monoethyl ether, propylene glycol and diethylene glycol monoethyl ether or monomethyl ether; and mixtures thereof. Non-aqueous solvents can be present in the conditioning composition of the present invention in an amount of about 1% to about 50%, and in particular about 5% to about 25%, by weight of the total weight of the carrier in the composition.

Non-limiting conditioning agents which may be used in opaque conditioners include: stearyltrimethylammonium chloride; behenetrimethylammonium chloride; cetrimonium bromide; soytrimonium chloride; tallowtrimonium chloride; dihyrogenatedtallowedimethylammonium chloride; behentrimethylammonium methosulfate; Peg-2 Oleammonium chloride; dihyrogenatedtallowedimethylammonium bromide; dihyrogenatedtallowedimethylammonium methosulfate; palmityltrimethylammonium chloride; hydrogenated tallowtrimethylammonium chloride; hydrogenated tallowtrimethylammonium bromide; dicetyidimethylammonium chloride; distearyldimethylammonium chloride; dipalmityidimethylammonium chloride; hydrogenated tallowtrimethylammonium methosulfate; cetrimonium tosylate: eicosyltrimethylammonium chloride, and ditallowedimethylammonium chloride.

Materials that can be used to opacify compositions of the invention include fatty esters, opacifying polymers, such as styrene polymers, like OPACIFIER 653 from Morton, International, Inc.; and fatty alcohols. The following is a non-limiting list of fatty alcohols: cetyl alcohol; stearyl alcohol; cetearyl alcohol; behenyl alcohol; and arachidyl alcohol. Conditioning compositions of the invention which are not clear also can include Lexamine S-13, dicetylammonium chloride, and ceteareth-20.

Shampoo formulations are sometimes advantageous for treating scalp lesions such psoriasis of the scalp.

The hair shampoo composition of the present invention may contain nonionic surfactants or amphoteric surfactants in order to improve its cleansing performance.

Examples of the nonionic surfactant include, but are not limited to, polyoxyalkylene sorbitan fatty acid esters, polyoxyalkylene sorbitol fatty acid esters, polyoxyalkylene glycerin fatty acid esters, polyoxyalkylene fatty acid esters, polyoxyalkylene alkyl ethers, polyoxyalkylene alkylphenyl ethers, polyoxyalkylene (hydrogenated) castor oils, sucrose fatty acid esters, polyglycerin alkyl ethers, polyglycerin fatty acid esters, fatty acid alkanolamides, and alkyl glycosides. Of these, alkyl glycosides, polyoxyalkylene ($C_8$ to $C_{22}$) fatty acid esters, polyoxyethylene sorbitan fatty acid esters, polyoxyethylene hydrogenated castor oils and fatty acid alkanolamides are preferred. As the fatty acid alkanolamides, those with an acyl group having from 8 to 18, more preferably from 10 to 16 carbon atoms are preferred. As the fatty acid alkanolamides, either of monoalkanolamides or dialkanolamides may be used and those with a hydroxyalkyl group having 2 to 3 carbon atoms are preferred. Examples include oleic diethanolamide, palm kernel fatty acid diethanolamide, coconut oil fatty acid diethanolamide, lauric acid diethanolamide, polyoxyethylene coconut oil fatty acid monoethanolamide, coconut oil fatty acid monoethanolamide, lauric acid isopropanolamide and lauric acid monoethanolamide.

The amphoteric surfactants which can be used in the shampoo composition of the present invention include betaine surfactants such as alkyldimethylaminoacetic acid betaines and fatty acid amidopropylbetaines. As the fatty acid amidopropylbetaines, those with an acyl group having from 8 to 18, more preferably from 10 to 16 carbon atoms are preferred, with lauryl amidopropylbetaine, palm kernel amidopropylbetaine and cocamidopropylbetaine being especially preferred.

The nonionic surfactant and amphoteric surfactant may be incorporated in the hair shampoo composition of the present invention as needed. Two or more of them may be used in combination. When the hair shampoo composition of the present invention is provided in the form of an aqueous liquid shampoo, use of fatty acid amidopropylbetaine or fatty acid alkanolamide is preferred, because it not only improves foaming power but also provides the shampoo with adequate fluidity.

The content of the nonionic surfactant in the hair shampoo composition may fall within a range of from 0 to 15 wt. %, more preferably from 0.5 to 10 wt. %, still more preferably from 1 to 5 wt. % in the hair shampoo composition, while that of the amphoteric surfactant in the hair shampoo composition may fall within a range of from 0 to 10 wt. %, more preferably 0.5 to 8 wt. %, still more preferably from 1 to 5 wt. %.

The hair shampoo composition of the present invention may further contain a cationic polymer in consideration of the texture of foams, lubricated feeling of foams, reduction in the friction between hair strands upon shampooing and smoothness after drying. Examples of the cationic polymer include cationic cellulose derivatives, cationic starch, cationic guar gum derivatives, homopolymers of a diallyl quaternary ammonium salt, diallyl quaternary ammonium salt/acrylamide copolymers, quaternized polyvinylpyrrolidone derivatives, polyglycol-polyamine condensation products, vinylimidazolium trichloride/vinylpyrrolidone copolymers, hydroxyethyl cellulose/dimethyldiallyl ammonium chloride copolymers, vinylpyrrolidone/quaternized dimethylaminoethyl methacrylate copolymers, polyvinylpyrrolidone/alkylamino acrylate copolymers, polyvinylpyrrolidone/alkylaminoacrylate/vinyl caprolactam copolymers, vinylpyrrolidone/methacrylamidopropyl trimethylammonium chloride copolymers, alkylacrylamide/acrylate/alkylaminoalkyl acrylamide/polyethylene glycol methacrylate copolymers, adipic acid/dimethylaminohydroxypropylethylenetriamine copolymers (CALTALETINE manufactured by US Sandos Corp.), and cationic polymers described in Japanese Patent Laid-Open No. Sho 53-139734 and Japanese Patent Laid-Open No. Sho 60-36407. Of these, cationic cellulose derivatives and cationic guar gum derivatives are preferred.

Two or more of these cationic polymers may be used in combination. Its content in the hair shampoo composition of the present invention is preferably from 0.02 to 5 wt. %, more preferably from 0.05 to 1 wt. %, and even more preferably from 0.1 to 0.3 wt. % from the viewpoints of improvement in the foam quality upon shampooing, manageability of hair after drying and improvement in feel.

The hair shampoo composition of the present invention may further contain a conditioning component such as silicone in order to improve the finish after drying. Examples of the silicone include dimethylpolysiloxane, methylphenylpolysiloxane, amino-modified silicone, polyether-modified silicone, epoxy-modified silicone, fluorine-modified silicone, cyclic silicones, alkyl-modified silicones, and oxazoline-modified silicone. Of these, dimethylpolysiloxane, methylphenylpolysiloxane, amino-modified silicone polyether-modified silicone, oxazoline-modified silicone and cyclic silicones are preferred. Two or more of these silicones may be used in combination. Its (their) content preferably ranges from 0.01 to 20 wt. %, more preferably from 0.05 to 10 wt. %, still more preferably from 0.1 to 5 wt. % in the hair shampoo composition of the present invention.

The hair shampoo composition of the present invention may contain, in addition to the above-described components, water soluble polymers such as hydroxypropylmethyl cellulose, hydroxyl cellulose, polyvinyl alcohol, and polyethylene glycol; polyhydric alcohols such as sorbitol; humectants; chelating agents such as ethylene diamine tetraacetic acid (EDTA); drugs such as vitamin preparations; amino acids and derivatives thereof; fine particles of a polymer such as polyethylene, polystyrene, poly(methyl methacrylate), nylon or silicone, and hydrophobic products thereof; extracts derived from animals or plants; ultraviolet absorbers; pearling agents; antiseptics; bactericides; pH regulators; colorants; and fragrances, according to the using purpose.

The hair shampoo composition of the present invention may be provided in any form selected from liquid, powder, gel and granule as needed. A liquid composition using water or a lower alcohol as a solvent is preferred, with a liquid composition using water being especially preferred.

As mentioned above, the pharmaceutical composition can be administered systemically or locally, e.g., by injection.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuos infusion. Formulations for injection may be presented in unit dosage form, e.g., in ampoules or in multi-dose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (the above described agents) effective to prevent, alleviate or ameliorate symptoms of the pathology characterized by hyperproliferative keratinocytes (e.g., psoriasis) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide tissue (the skin tissue) levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

It will be appreciated that treatment regimen described herein may be augmented using anti psoriasis conventional medicine.

Thus, according to some embodiments of the invention, the method further comprising administering to the subject an agent capable of at least partially reducing symptoms of the pathology, wherein the agent is suitable for topical or systemic (e.g., oral or injected) administration and/or for treating the subject with light therapy.

It should be noted that administering the agent capable of at least partially reducing symptoms of the pathology can be performed prior to treatment with the IGFBP7 polypeptide or polynucleotide, concomitantly with treating with the IGFBP7 polypeptide or polynucleotide or following the treatment with the IGFBP7 polypeptide or polynucleotide.

The agent capable of at least partially reducing symptoms of the pathology can form part of the pharmaceutical composition (e.g., part of the active ingredients) in combination with the IGFBP7 polypeptide or the polynucleotide encoding the IGFBP7 polypeptide as described above.

The agent suitable for the topical therapy (topical administration of a medicament) can be a corticosteroid, a vitamin D analogue or derivative, anthralin, topical retinoid, calcineurin inhibitor, salicylic acid, coal tar and a moisturizer either in the form of a cream, an unguent, a gel or an emulsion.

According to some embodiments of the invention, the light therapy can be sun light phototherapy, type B ultraviolet (UVB) phototherapy, narrowband UVB phototherapy, photochemotherapy e.g., PUVA [a combination treatment which consists of Psoralens (P) and then exposing the skin to UVA (long wave ultraviolet radiation)] and excimer laser.

The agent suitable for the systemic therapy (systemic administration of a medicament) can be a retinoid, an immunosuppressive drug (e.g., methotrexate, cyclosporine), an immune-targeting biologic agent (e.g., Alafacept, infliximab, infliximab, etanercept, ustekinumab), an immunotoxin (e.g., denileukin), and TNF-alpha blocking biological agent (e.g., infliximab, adalimumab, etanercept, golimumab and the like).

According to some embodiments of the invention, regulating keratinocytes proliferation and differentiation comprises upregulating the proliferation by downregulating the expression level and/or activity of IGFBP7.

According to embodiments of the present invention upregulating the proliferation is for the treatment of wounds, burns, ulcers and skin regeneration in general.

Downregulation of IGFBP7 can be effected on the genomic and/or the transcript level using a variety of molecules which interfere with transcription and/or translation (e.g., RNA silencing agents, Ribozyme, DNAzyme and antisense), or on the protein level using e.g., antagonists, enzymes that cleave the polypeptide, antibodies that neutralize IGFBP7 activity ((ab51392 Abcam) and the like.

Following is a list of agents capable of downregulating expression level and/or activity of IGFBP7.

One example, of an agent capable of downregulating a IGFBP7 is an antibody or antibody fragment capable of specifically binding IGFBP7. Preferably, the antibody specifically binds at least one epitope of a IGFBP7. As used herein, the term "epitope" refers to any antigenic determinant on an antigen to which the paratope of an antibody binds.

Epitopic determinants usually consist of chemically active surface groupings of molecules such as amino acids or carbohydrate side chains and usually have specific three dimensional structural characteristics, as well as specific charge characteristics.

The term "antibody" as used in this invention includes intact molecules as well as functional fragments thereof, such as Fab, F(ab')2, and Fv that are capable of binding to macrophages. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments according to the present invention can be prepared by proteolytic hydrolysis of the antibody or by expression in E. coli or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (19720]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by [Whitlow and Filpula, Methods 2: 97-105 (1991); Bird et al., Science 242:423-426 (1988); Pack et al., Bio/Technology 11:1271-77 (1993); and U.S. Pat. No. 4,946, 778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

Humanized forms of non-human (e.g., murine) antibodies are chimeric molecules of immunoglobulins, immunoglobulin chains or fragments thereof (such as Fv, Fab, Fab', F(ab').sub.2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545, 807; 5,545,806; 5,569,825; 5,625,126; 5,633,425; 5,661,016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

Downregulation of IGFBP7 can be also achieved by RNA silencing. As used herein, the phrase "RNA silencing" refers to a group of regulatory mechanisms [e.g. RNA interference (RNAi), transcriptional gene silencing (TGS), post-transcriptional gene silencing (PTGS), quelling, co-suppression, and translational repression] mediated by RNA molecules which result in the inhibition or "silencing" of the expression of a corresponding protein-coding gene. RNA silencing has been observed in many types of organisms, including plants, animals, and fungi.

As used herein, the term "RNA silencing agent" refers to an RNA which is capable of inhibiting or "silencing" the expression of a target gene. In certain embodiments, the RNA silencing agent is capable of preventing complete processing (e.g, the full translation and/or expression) of an mRNA molecule through a post-transcriptional silencing mechanism. RNA silencing agents include noncoding RNA molecules, for example RNA duplexes comprising paired strands, as well as precursor RNAs from which such small non-coding RNAs can be generated. Exemplary RNA silencing agents include dsRNAs such as siRNAs, miRNAs and shRNAs. In one embodiment, the RNA silencing agent is capable of inducing RNA interference. In another embodiment, the RNA silencing agent is capable of mediating translational repression.

RNA interference refers to the process of sequence-specific post-transcriptional gene silencing in animals mediated by short interfering RNAs (siRNAs). The corresponding process in plants is commonly referred to as post-transcriptional gene silencing or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla. Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA.

The presence of long dsRNAs in cells stimulates the activity of a ribonuclease III enzyme referred to as dicer. Dicer is involved in the processing of the dsRNA into short pieces of dsRNA known as short interfering RNAs (siRNAs). Short interfering RNAs derived from dicer activity are typically about 21 to about 23 nucleotides in length and comprise about 19 base pair duplexes. The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex.

Accordingly, the present invention contemplates use of dsRNA to down-regulate protein expression from mRNA.

According to one embodiment, the dsRNA is greater than 30 bp. The use of long dsRNAs (i.e. dsRNA greater than 30 bp) has been very limited owing to the belief that these longer regions of double stranded RNA will result in the induction of the interferon and PKR response. However, the use of long dsRNAs can provide numerous advantages in that the cell can select the optimal silencing sequence alleviating the need to test numerous siRNAs; long dsRNAs will allow for silencing libraries to have less complexity than would be necessary for siRNAs; and, perhaps most importantly, long dsRNA could prevent viral escape mutations when used as therapeutics.

Various studies demonstrate that long dsRNAs can be used to silence gene expression without inducing the stress response or causing significant off-target effects—see for example [Strat et al., Nucleic Acids Research, 2006, Vol. 34, No. 13 3803-3810; Bhargava A et al. Brain Res. Protoc. 2004; 13:115-125; Diallo M., et al., Oligonucleotides. 2003; 13:381-392; Paddison P. J., et al., Proc. Natl. Acad. Sci. USA. 2002; 99:1443-1448; Tran N., et al., FEB S Lett. 2004; 573: 127-134].

In particular, the present invention also contemplates introduction of long dsRNA (over 30 base transcripts) for gene silencing in cells where the interferon pathway is not activated (e.g. embryonic cells and oocytes) see for example Billy et al., PNAS 2001, Vol 98, pages 14428-14433. and Diallo et al, Oligonucleotides, Oct. 1, 2003, 13(5): 381-392. doi:10.1089/154545703322617069.

The present invention also contemplates introduction of long dsRNA specifically designed not to induce the interferon and PKR pathways for down-regulating gene expression. For example, Shinagwa and Ishii [Genes & Dev. 17 (11): 1340-1345, 2003] have developed a vector, named pDECAP, to express long double-strand RNA from an RNA polymerase II (Pol II) promoter. Because the transcripts from pDECAP lack both the 5'-cap structure and the 3'-poly(A) tail that facilitate ds-RNA export to the cytoplasm, long ds-RNA from pDECAP does not induce the interferon response.

Another method of evading the interferon and PKR pathways in mammalian systems is by introduction of small inhibitory RNAs (siRNAs) either via transfection or endogenous expression.

The term "siRNA" refers to small inhibitory RNA duplexes (generally between 18-30 basepairs) that induce the RNA interference (RNAi) pathway. Typically, siRNAs are chemically synthesized as 21mers with a central 19 bp duplex region and symmetric 2-base 3'-overhangs on the termini, although it has been recently described that chemically synthesized RNA duplexes of 25-30 base length can have as much as a 100-fold increase in potency compared with 21mers at the same location. The observed increased potency obtained using longer RNAs in triggering RNAi is theorized to result from providing Dicer with a substrate (27mer) instead of a product (21mer) and that this improves the rate or efficiency of entry of the siRNA duplex into RISC.

It has been found that position of the 3'-overhang influences potency of an siRNA and asymmetric duplexes having a 3'-overhang on the antisense strand are generally more potent than those with the 3'-overhang on the sense strand (Rose et al., 2005). This can be attributed to asymmetrical strand loading into RISC, as the opposite efficacy patterns are observed when targeting the antisense transcript.

The strands of a double-stranded interfering RNA (e.g., an siRNA) may be connected to form a hairpin or stem-loop structure (e.g., an shRNA). Thus, as mentioned the RNA silencing agent of the present invention may also be a short hairpin RNA (shRNA).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop. Examples of oligonucleotide sequences that can be used to form the loop include 5'-UUCAAGAGA-3' (Brummelkamp, T. R. et al. (2002) Science 296: 550) and 5'-UUUGUGUAG-3' (Castanotto, D. et al. (2002) RNA 8:1454). It will be recognized by one of skill in the art that the resulting single chain oligonucleotide forms a stem-loop or hairpin structure comprising a double-stranded region capable of interacting with the RNAi machinery.

According to another embodiment the RNA silencing agent may be a miRNA. miRNAs are small RNAs made from genes encoding primary transcripts of various sizes. They have been identified in both animals and plants. The primary transcript (termed the "pri-miRNA") is processed through various nucleolytic steps to a shorter precursor miRNA, or "pre-miRNA." The pre-miRNA is present in a folded form so that the final (mature) miRNA is present in a duplex, the two strands being referred to as the miRNA (the strand that will eventually basepair with the target) The pre-miRNA is a substrate for a form of dicer that removes the miRNA duplex from the precursor, after which, similarly to siRNAs, the duplex can be taken into the RISC complex. It has been demonstrated that miRNAs can be transgenically expressed and be effective through expression of a precursor form, rather than the entire primary form (Parizotto et al. (2004) Genes & Development 18:2237-2242 and Guo et al. (2005) Plant Cell 17:1376-1386).

Unlike, siRNAs, miRNAs bind to transcript sequences with only partial complementarity (Zeng et al., 2002, Molec. Cell 9:1327-1333) and repress translation without affecting steady-state RNA levels (Lee et al., 1993, Cell 75:843-854; Wightman et al., 1993, Cell 75:855-862). Both miRNAs and siRNAs are processed by Dicer and associate with components of the RNA-induced silencing complex (Hutvagner et al., 2001, Science 293:834-838; Grishok et al., 2001, Cell 106: 23-34; Ketting et al., 2001, Genes Dev. 15:2654-2659; Williams et al., 2002, Proc. Natl. Acad. Sci. USA 99:6889-6894; Hammond et al., 2001, Science 293:1146-1150; Mourlatos et al., 2002, Genes Dev. 16:720-728). A recent report (Hutvagner et al., 2002, Sciencexpress 297:2056-2060) hypothesizes that gene regulation through the miRNA pathway versus the siRNA pathway is determined solely by the degree of complementarity to the target transcript. It is speculated that siRNAs with only partial identity to the mRNA target will function in translational repression, similar to an miRNA, rather than triggering RNA degradation.

Synthesis of RNA silencing agents suitable for use with the present invention can be effected as follows. First, the IGFBP7 mRNA sequence is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex [Tuschl ChemBiochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level [World Wide Web (dot) ambion (dot) com/techlib/tn/91/912 (dot) html].

Second, potential target sites are compared to an appropriate genomic database (e.g., human, mouse, rat etc.) using any sequence alignment software, such as the BLAST software available from the NCBI server [World Wide Web (dot) ncbi (dot) nlm (dot) nih (dot) gov/BLAST/]. Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

For example, a suitable IGFBP7 siRNA is available from Sigma-Aldriech

It will be appreciated that the RNA silencing agent of the present invention need not be limited to those molecules containing only RNA, but further encompasses chemically-modified nucleotides and non-nucleotides.

In some embodiments, the RNA silencing agent provided herein can be functionally associated with a cell-penetrating peptide." As used herein, a "cell-penetrating peptide" is a peptide that comprises a short (about 12-30 residues) amino acid sequence or functional motif that confers the energy-independent (i.e., non-endocytotic) translocation properties associated with transport of the membrane-permeable complex across the plasma and/or nuclear membranes of a cell. The cell-penetrating peptide used in the membrane-permeable complex of the present invention preferably comprises at least one non-functional cysteine residue, which is either free or derivatized to form a disulfide link with a double-stranded ribonucleic acid that has been modified for such linkage. Representative amino acid motifs conferring such properties are listed in U.S. Pat. No. 6,348,185, the contents of which are expressly incorporated herein by reference. The cell-penetrating peptides of the present invention preferably include, but are not limited to, penetratin, transportan, pIs1, TAT(48-60), pVEC, MTS, and MAP.

mRNAs to be targeted using RNA silencing agents include, but are not limited to, those whose expression is correlated with an undesired phenotypic trait. Exemplary mRNAs that may be targeted are those that encode truncated proteins i.e. comprise deletions. Accordingly the RNA silencing agent of the present invention may be targeted to a bridging region on either side of the deletion. Introduction of such RNA silencing agents into a cell would cause a down-regulation of the mutated protein while leaving the non-mutated protein unaffected.

Another agent capable of downregulating a IGFBP7 is a DNAzyme molecule capable of specifically cleaving an mRNA transcript or DNA sequence of the IGFBP7. DNAzymes are single-stranded polynucleotides which are capable of cleaving both single and double stranded target sequences (Breaker, R. R. and Joyce, G. Chemistry and Biology 1995; 2:655; Santoro, S. W. & Joyce, G. F. Proc. Natl, Acad. Sci. USA 1997; 943:4262) A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (Santoro, S. W. & Joyce, G. F. Proc. Natl, Acad. Sci. USA 199; for rev of DNAzymes see Khachigian, L M [Curr Opin Mol Ther 4:119-21 (2002)].

Examples of construction and amplification of synthetic, engineered DNAzymes recognizing single and double-stranded target cleavage sites have been disclosed in U.S. Pat. No. 6,326,174 to Joyce et al. DNAzymes of similar design directed against the human Urokinase receptor were recently observed to inhibit Urokinase receptor expression, and successfully inhibit colon cancer cell metastasis in vivo (Itoh et al, 20002, Abstract 409, Ann Meeting Am Soc Gen Ther World Wide Web (dot) asgt (dot) org). In another application, DNAzymes complementary to bcr-abl oncogenes were successful in inhibiting the oncogenes expression in leukemia cells, and lessening relapse rates in autologous bone marrow transplant in cases of CML and ALL.

Downregulation of a IGFBP7 can also be effected by using an antisense polynucleotide capable of specifically hybridizing with an mRNA transcript encoding the IGFBP7.

Design of antisense molecules which can be used to efficiently downregulate a IGFBP7 must be effected while considering two aspects important to the antisense approach. The first aspect is delivery of the oligonucleotide into the cytoplasm of the appropriate cells, while the second aspect is design of an oligonucleotide which specifically binds the designated mRNA within cells in a way which inhibits translation thereof.

The prior art teaches of a number of delivery strategies which can be used to efficiently deliver oligonucleotides into a wide variety of cell types [see, for example, Luft J Mol Med 76: 75-6 (1998); Kronenwett et al. Blood 91: 852-62 (1998); Rajur et al. Bioconjug Chem 8: 935-40 (1997); Lavigne et al. Biochem Biophys Res Commun 237: 566-71 (1997) and Aoki et al. (1997) Biochem Biophys Res Commun 231: 540-5 (1997)].

In addition, algorithms for identifying those sequences with the highest predicted binding affinity for their target mRNA based on a thermodynamic cycle that accounts for the energetics of structural alterations in both the target mRNA and the oligonucleotide are also available [see, for example, Walton et al. Biotechnol Bioeng 65: 1-9 (1999)].

Such algorithms have been successfully used to implement an antisense approach in cells. For example, the algorithm developed by Walton et al. enabled scientists to successfully design antisense oligonucleotides for rabbit beta-globin (RBG) and mouse tumor necrosis factor-alpha (TNF alpha) transcripts. The same research group has more recently reported that the antisense activity of rationally selected oligonucleotides against three model target mRNAs (human lactate dehydrogenase A and B and rat gp130) in cell culture as evaluated by a kinetic PCR technique proved effective in almost all cases, including tests against three different targets in two cell types with phosphodiester and phosphorothioate oligonucleotide chemistries.

In addition, several approaches for designing and predicting efficiency of specific oligonucleotides using an in vitro system were also published (Matveeva et al., Nature Biotechnology 16: 1374-1375 (1998)].

Several clinical trials have demonstrated safety, feasibility and activity of antisense oligonucleotides. For example, antisense oligonucleotides suitable for the treatment of cancer have been successfully used [Holmund et al., Curr Opin Mol Ther 1:372-85 (1999)], while treatment of hematological malignancies via antisense oligonucleotides targeting c-myb gene, p53 and Bcl-2 had entered clinical trials and had been shown to be tolerated by patients [Gerwitz Curr Opin Mol Ther 1:297-306 (1999)].

More recently, antisense-mediated suppression of human heparanase gene expression has been reported to inhibit pleural dissemination of human cancer cells in a mouse model [Uno et al., Cancer Res 61:7855-60 (2001)].

Thus, the current consensus is that recent developments in the field of antisense technology which, as described above, have led to the generation of highly accurate antisense design algorithms and a wide variety of oligonucleotide delivery systems, enable an ordinarily skilled artisan to design and implement antisense approaches suitable for downregulating expression of known sequences without having to resort to undue trial and error experimentation.

Another agent capable of downregulating a IGFBP7 is a ribozyme molecule capable of specifically cleaving an mRNA transcript encoding a IGFBP7. Ribozymes are being increasingly used for the sequence-specific inhibition of gene expression by the cleavage of mRNAs encoding proteins of interest [Welch et al., Curr Opin Biotechnol. 9:486-96 (1998)]. The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders [Welch et al., Clin Diagn Virol. 10:163-71 (1998)]. Most notably, several ribozyme gene therapy protocols for HIV patients are already in Phase 1 trials. More recently, ribozymes have been used for transgenic animal research, gene target validation and pathway elucidation. Several ribozymes are in various stages of clinical trials. ANGIOZYME was the first chemically synthesized ribozyme to be studied in human clinical trials. ANGIOZYME specifically inhibits formation of the VEGF-r (Vascular Endothelial Growth Factor receptor), a key component in the angiogenesis pathway. Ribozyme Pharmaceuticals, Inc., as well as other firms have demonstrated the importance of anti-angiogenesis therapeutics in animal models. HEPTAZYME, a ribozyme designed to selectively destroy Hepatitis C Virus (HCV) RNA, was found effective in decreasing Hepatitis C viral RNA in cell culture assays (Ribozyme Pharmaceuticals, Incorporated—WEB home page).

Still another agent capable of downregulating IGFBP7 activity is a non-functional variant of IGFBP7-effector protein, also termed as dominant negative. Such a dominant negative variant is an effector protein which binds IGFBP7 but cannot exert downstream signaling therefrom. Examples of such include dominant negative IGF and dominant negative insulin. Such agents are capable of binding insulin but cannot bind IRS1/2 for example.

Any of the downregulating agents described herein can be included in a pharmaceutical composition along with a pharmaceutically acceptable carrier as described above.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Methods

Cell Cultures—

HaCat cells, a spontaneously immortalized human keratinocyte line, were kindly provided by Dr. Dina Ron (Technion, Haifa, Israel). The cells were maintained in high-glucose DMEM medium containing 0.075 mM or 1.4 mM $CaCl_2$ supplemented with 10% fetal calf serum, 1% L-glutamine and 1% penicillin/streptomycin (Biological Industries, Beit-Ha-Emek, Israel).

Primary human keratinocytes were purchased from CELLnTEC Advanced Cell Systems (Bern, Switzerland). Cells were grown in KC growth medium (KGM) containing 0.15 mM $CaCl_2$ supplemented with growth factor bullet kit (Lonza, Md. USA). Medium was changed every 2-3 days. Cells were used at passage 3. For differentiation, cells were cultured in KGM media and 1.4 mM $CaCl_2$.

Immunohistochemistry—

Formaldehyde-fixed 5-μm paraffin-embedded sections were treated with 3% $H_2O_2$ in methanol for 15 min at room temperature, warmed in a microwave oven in citrate buffer for 15 min at 90° C., and stained with mouse monoclonal anti-IGFBP7 antibodies (R&D Systems, Minneapolis Minn., USA), anti-keratin 14 antibodies (BioGenex, San Ramon, Calif.), or preimmune rabbit antiserum for 1 hour at room temperature. After extensive washings in phosphate-buffered saline, the antibodies were revealed using the ABC technique (Zymed Laboratories, South San Francisco, Calif., USA), and the slides were counterstained with hematoxylin.

siRNA Transfection—

Primary KC cells were cultured in six-well plates at a density of $8\times10^4$ cells per well before transfection with 66 nmol $l^{-1}$ siRNA duplexes against IGFBP7 or negative control siRNA (Invitrogene Carlsbad, Calif., USA) using Lipofectamine 2000 (Invitrogen, Carlsbad, Calif., USA). Five different siRNA species were tested for down-regulation of IGFBP7. The siRNA IGFBP7 duplex that was selected for further use in this study consisted of 5'-rGrCUrGrGUrAUrCUrCrCUrCUrArArGUTT-3' (SEQ ID NO:32) and 5'-rArCUUrArGrArGrGrArGrAUrArCrCrArGrCTT-3' (SEQ ID NO:33) (Sigma-Proligo, Tex., USA). As a negative control, a standard scrambled siRNA purchased from InVitrogen was used (Catalogue No. 12935200).

shRNA Lentiviral Transduction—

To achieve stable gene down-regulation, a DNA shRNA-expressing lentiviral vector was used (5'-CCGGCAATC-CACTAACACTTTAGTTCTCGAGAAC-TAAAGTGTTAGTGGATTG TTTTTG; SEQ ID NO:34; hIGFBP7 NM_001553 lentiviral particles Sigma, cat No. TRCN0000077943). Non-target sh-control lentiviral particles were purchased from Sigma, Catalogue No. SHC002V. The shRNA-expressing lentiviral vector contain viral packaging signals, regulatory elements and puromycin resistance gene to package the shRNA sequence into infectious virions (Sigma-Aldrich, St Louis, Mo., USA). HaCat cells were transduced with shRNA Lentiviral Particles according to the manufacturer's recommendations. Briefly, 24 hours prior to transduction, cells were grown in six-well plates to $1.6\times10^4$ cells/well. 1-5 μl of viral stock and 2 μl of 4 mg/ml Polybrene was added to the cells for 18-20 hours incubation at 37° C. in 5% $CO_2$ humidified incubator. The amount of the viral stock was determined according to desired MOI (MOI=5) and total Transducing Units/ml supplied by Sigma. The formula for calculation is (total number of cells per well)*(desired MOI) =total transducing units (TU) needed; TU needed/(TU/ml supplied)=total ml of lentiviral particles for each well. 24 hours after transduction the cells were washed twice in PBS×1 and maintained in complete growth medium. After expansion in culture for 48 hours, the cells were maintained in growth medium supplemented with puromycin at a final concentration of 4 μg/ml. Selection was performed in the presence of puromycin for one week. Selected clones were frozen in liquid nitrogen prior to further use.

Primary keratinocytes were transduced according to the same protocol as described for HaCat cells with slight modifications. 24 hours after transduction the cells were washed twice in PBS×1 and maintained in KGM medium containing 0.15 mM or 1.4 mM $CaCl_2$. After expansion in culture for 72 hours the cells were used for in vitro assays.

Quantitative Reverse Transcription-PCR—

RNA was extracted from cultured cells using an RNA extraction kit (Roche Mannheim, Germany). cDNA was synthesized from 500 ng of total RNA using the Reverse-iT first strand synthesis kit (ABgene, Epson, UK) and random hexamers. cDNA PCR amplification was carried out using the SYBR Green JumpStart Taq ReadyMix (Sigma-Aldrich, St Louis, Mo., USA) on a M×3000 p/5 p multifilter system (Stratagene, Cedar Creek, Tex., USA) with gene-specific intron-crossing oligonucleotide pairs listed in Table 2 below. To ensure the specificity of the reaction conditions, at the end of the individual runs, the melting temperature (Tm) of the amplified products was measured to confirm its homogeneity. Cycling conditions were as follows: 95° C. for 10 minutes, 95° C. for 10 seconds, 62° C. for 15 seconds, and 72° C. for 25 seconds for a total of 40 cycles. Each sample was analyzed in triplicate. For quantification, standard curves were obtained using serially diluted cDNA amplified in the same real-time PCR run. Results were normalized to ACTB and GAPDH mRNA levels. After the quantification procedure, the products were resolved by 2.5% agarose gel electrophoresis to confirm that the reaction had amplified DNA fragments of expected size.

transferred onto a nitrocellulose membrane (Trans-Blot Bio-Rad, Hercules, Calif., USA). After 1 hour blocking with 1× Tris-buffered saline (20 mM Tris, 150 mM NaCl) with 3% BSA and 0.01% Tween 20, blots were incubated with primary antibodies. The primary antibodies included antibodies to p-IRS-1, IRS-1, p-ERK 1/2, ERK 2, SMAD 2/3, p-SMAD 2/3 (Santa Cruz Biotechnology, Santa Cruz, Calif., USA); IGFBP7 (R&D Systems, Minneapolis Minn., USA); Cytokeratin 6 (ABCAM, Cambridge, Mass., USA). The blots were washed three times with Tris-buffered saline-Tween (20 mM Tris HCl, 4 mM Tris base, 140 mM NaCl, 1 mM EDTA, 0.1% Tween 20). After incubation with secondary horseradish peroxidase-conjugated anti-mouse or anti-rabbit antibody (Sigma-Aldrich, St Louis, Mo., USA) and subsequent washings, proteins were detected using the EZ-ECL chemiluminescence detection kit (Biological Industries, Beit Haemek, Israel). To compare the amount of protein in the different samples, the blots were re-probed with a mouse monoclonal

TABLE 2

Oligonucleotide sequences

| Gene Symbol | Forward primer | SEQ ID NO: | Reverse primer | SEQ ID NO: |
|---|---|---|---|---|
| IGFBP7 | CGAGCAAGGTCCTTCCATAGTG | 35 | CCGATGACCTCACAGCTCAAG | 36 |
| KRT10 | GGAAGAATCAAACTATGAGCTG | 37 | ATTGTCGATCTGAAGCAGG | 38 |
| KRT6A | CTGAATGGCGAAGGCGTT | 39 | CCACTGCCGACACCACT | 40 |
| IVL | TGTTCCTCCTCCAGTCAATA | 41 | GCTTTGATGGGACCTCCACT | 42 |
| ACTB | CGATCACATTAGTGCCATTC | 43 | AGGTGGACAGCGAGGCCAGGA | 44 |
| GAPDH | GAGTCAACGGATTTGGTCGT | 45 | GACAAGCTTCCCGTTCTCAGCC | 46 |

Table 2. Provided are the primers used to amplify the indicated genes along with their sequence identifiers.

Microarray Hybridization and Data Analysis—

Total RNA (200 ng) was reverse transcribed and cRNA (complementary RNA) prepared using TotalPrep RNA Amplification Kit (Applied Biosystems/Ambion, Austin, USA) according to manufacturer's protocol. 1.5 µg of biotinylated cRNA was hybridized to Sentrix Human WG-6 v2 array (encompassing 48,701 transcript targets), washed, and scanned on a BeadArray Reader (Illumina, San Diego, Calif.). The scanning data were exported to MatLab sofware, quantile normalized and transcripts with detection p value greater than 0.01 were removed from the analysis (more than 13,000 transcripts had a p value <0.01). In the global GO term analysis, all GO terms that were present in the gene set more than once were tested. The gene set was composed from the top 100 genes whose calcium-induced up- or down-regulation was most markedly affected by IGFBP7 silencing. For each term the same number of genes as in the gene set was randomly selected and the number of times it appeared in this set was calculated. The process was repeated 100 times and a histogram of this GO term frequency was built. The results were analyzed using the One-sample Wilcoxon Signed-Ranks Test to assess relative enrichment in our experimental gene set.

Western Blotting—

Cells were homogenized in Cellytic MT lysis/extraction reagent (Sigma-Aldrich, St Louis, Mo., USA) and protease inhibitors mix, including 1 mM PMSF, 1 mg ml-1 aprotinin and leupeptin (Sigma-Aldrich, St Louis, Mo., USA). Following centrifugation at 10,000×g for 10 minutes at 4° C., proteins were electrophoresed through a 10% SDS-PAGE and antibody to β-actin (Abcam, Cambridge, UK) and secondary horseradish peroxidase-conjugated anti-mouse antibody (Sigma-Aldrich, St Louis, Mo., USA).

MTT Assay—

The MTT test is based on the selective ability of living cells to reduce the yellow salt MTT (3-(4,5-dimethylthiazolyl-2)-2,5-diphenyltetrazolium bromide) (Sigma, Aldrich St Louis, Mo., USA) to a purple-blue insoluble formazan precipitate. MTT was dissolved in phosphate buffered saline (PBS) at 5 mg/ml and added to each well (10% of total volume) for 30 min incubation at 37° C. After incubation the media was removed and the purple formazan product dissolved in dimethylsulphoxide (DMSO). The supernatants were collected and then scanned with an ELISA reader Zenyth 200 (Anthos Labtec, Cambridge, UK) at 560 nm.

BrDu Assay—

The incorporation rate of BrdU was determined by Cell Proliferation ELISA BrdU colorimetric kit (Roche, Mannheim, Germany) according to manufacturer's protocol. Absorbance at 450 nm was measured using an ELISA reader. Briefly, cells were cultured in 6-well plates and incubated with BrdU for 6 hours at 37° C. Then the cells were fixed and the DNA was denatured by adding FixDenat solution. The anti-BrdU POD antibody was added for 90 min at RT and the cells were rinsed. Immune complexes were detected by adding substrate solution at absorbance 450 nm using ELISA reader Zenyth 200 (Anthos Labtec, Cambridge, UK).

TUNEL Assay—

Apoptosis was assessed using the TUNEL kit (Roche, Mannheim, Germany) according to the manufacturer's protocol. Briefly, cells were plated on cover slips with or without the addition of 10 ng/ml of TNF-α (PeproTech, Rocky Hill, N.J., USA) for 12 hours, air-dried and fixed with a freshly prepared fixation solution (4% paraformaldehyde in phosphate-buffered saline) and then rinsed twice with phosphate buffered saline. Cells were permeabilized with 0.1% Triton X-100 in 0.1% sodium citrate. Cell samples were incubated in a humidified atmosphere for 1 hour at 37° C. in the dark in the presence of the TUNEL reaction mixture and counterstained with DAPI. More than 1,000 cells were counted for each slide and examined under a fluorescent microscope Zeiss Axioscope 2 (Carl Zeiss MicroImaging, Inc., Thornwood, N.Y.). Image analysis was performed with Image-Pro Plus 5 software. Differences in apoptotic activity were considered significant at p-values <0.01 calculated using a standard Student's t-test.

Annexin V Assay—

Annexin V assay was performed using ApoAlert® Annexin V Apoptosis Kit (Clontech Laboratories, Inc., CA, USA) according to the manufacturer's protocol. Briefly, cells were plated on cover slips with or without the addition of 10 ng/ml of TNF-α (PeproTech, Rocky Hill, N.J., USA) for 12 hours, rinsed with supplied binding buffer and incubated with Annexin V and Propidium Iodide at room temperature for 15 minutes in the dark. Hoechst stain was used to counterstain the cells. More than 1,000 cells were counted for each slide and examined under a fluorescent microscope Carl Zeiss MicroImaging, Inc., Thornwood, N.Y.). Image analysis was performed with Image-Pro Plus 5 software. Differences in apoptotic activity were considered significant at p values <0.01 calculated using a standard Student's t-test.

Senescence Associated-β-Galactosidase Assay—

Cells were seeded 48 hours prior to staining at $2-4\times10^4$ cells/well in six well plates. This cell density ensures that the staining is performed before the cultures reach confluency. SA-β-Gal staining was performed as previously described with minor modifications (Dimri G P, Lee X, et al. 1995. A biomarker that identifies senescent human cells in culture and in aging skin in vivo. Proc Natl Acad Sci USA 92:9363-9367). Briefly, the cells were washed with cold PBS, and fixed for 5 min with 0.5% glutaraldehyde diluted in cold PBS. After fixation, cells were washed in PBS and incubated for 8 hours at 37° C. in staining solution containing 1 mg/ml 5-bromo-4-chloro-3-indolyl-β-D-galactoside (X-Gal) (Roche, Mannheim, Germany) and the rest of the components as previously described (Dimri et al., 1995, Supra). For staining at different pH values, 0.1 M citric acid and 0.2 M $Na_2HPO_4$ solutions were mixed at appropriate proportions. Following the incubation period at 37° C., cells were washed three times with cold PBS and stored in PBS at 4° C. until images were collected.

Quantitative analysis of the images was performed using a Matlab application for cell marking (SegmentGui) and color analysis [Hypertext Transfer Protocol://md (dot) technion (dot) ac (dot) il/pictures/storage/45/47 (dot) zip]. For each measurement, a minimum of 250 randomly chosen cells were marked manually. Kolmogorov-Smirnov test was used for statistical analysis. Differences below p value of 0.05 were considered significant.

Example 1

IGFBP7 Expression is Decreased in Psoriatic Skin Compared with Normal Skin

Experimental Results

IGFBP7 Expression is Decreased in Psoriatic Skin Compared with Normal Skin—

Previous data showed that psoriasis is associated with decreased expression of IGFBP7 (Hochberg et al., 2007). To confirm these data in an independent set of patients, the present inventors have examined by immunohistochemistry the expression of IGFBP7 protein in a series of psoriatic (n=13) and control (n=13) biopsies (FIG. 1D). IGFBP7 was found to be expressed strongly throughout the normal epidermis (FIG. 1A), whereas its expression was either absent or very weak in psoriatic epidermis (FIG. 1C). These results demonstrate that in skin of psoriasis patients there is a decreased expression of IGFBP7.

Serum Stimulation Downregulates IGFBP7 Expression—

To test the effect of serum on IGFBP7 expression levels, HaCat cells were cultured in the presence of increasing concentrations of fetal calf serum and the level of IGFBP7 RNA were determined 48 hours later. As shown in FIG. 12, serum stimulation was found to down-regulate IGFBP7 expression, suggesting a possible role for EGFR signaling in the regulation of IGFBP7 expression. In contrast no effect of calcium on IGFBP7 was observed (data not shown).

Example 2

Downregulation of IGFBP7 Increases Keratinocyte Proliferation, Viability and Apoptosis To test whether IGFBP7 is involved in the pathogenesis of psoriasis, a disorder characterized by abnormal proliferation and differentiation of epidermal keratinocytes, the present inventors induced downregulation of IGFBP7 in keratinocyte cells as follows.

Experimental Results

IGFBP7 siRNA Results in Specific Down-Regulation of IGFBP7 and not Other Genes in the IGFNP Family—

The present inventors assessed the role for IGFBP7 expression in the regulation of epidermal keratinocyte proliferation. siRNA and shRNA were used to transiently and stably decrease IGFBP7 expression in HaCat cells, respectively and shRNA was used to transiently decrease IGFBP7 expression in human primary keratinocytes. Down-regulation of IGFBP7 was confirmed by qRT-PCR (FIG. 2A) and immunoblotting of conditioned media (FIG. 2B). To exclude off-target effects of the siRNA and shRNA used, the present inventors tested the effect of IGFBP7 down-regulation on the levels of expression of other members of the IGFBP family and found no significant changes in their mRNA levels (FIG. 8), suggesting that the siRNA and shRNA used specifically targeted IGFBP7.

Downregulation of IGFBP7 Increases Keratinocyte Cell Viability and Proliferation—

Downregulation of IGFBP7 in HaCat cells increased cell viability as assessed by the MTT assay (FIG. 3A) and cell proliferation rates as determined by BrDU incorporation (FIG. 3B). Concomitant with an increase in cell proliferation, the expression of KRT6, a marker of epidermal proliferation, was up-regulated in HaCat cells (FIGS. 3C and 3D) and primary keratinocytes (FIG. 10) which were down-regulated for IGFBP7. These data was further confirmed in primary keratinocytes using both the MTT (FIG. 3E) and the BrDU incorporation assays (FIG. 3F).

Decreased IGFBP7 Expression is Associated with Decreased Apoptosis in Keratinocytes—

IGFBP7 has been shown to induce cell apoptosis and senescence in a number of cancer cell lines (Akaogi et al., 1996; Burger et al., 2005; Ruan et al., 2007; Sato et al., 2007; Wajapeyee et al., 2008; Wilson et al., 2002). The present inventors assessed the effect of IGFBP7 downregulation on apoptotic activity in keratinocytes. HaCat cells were stably or transiently transfected with either IGFBP7-specific or control shRNA or siRNA, and apoptosis was estimated using the TUNEL and annexin V assays. The present inventors found out that decreased IGFBP7 expression in HaCat cells lead to a concomitant decrease in apoptotic activity even in the presence of 10 ng/μl of recombinant TNF-α (FIGS. 4A-B). Similarly, downregulation of IGFBP7 by IGFBP7-specific siRNA in primary keratinocytes prevented TNF-α-induced cell apoptosis (FIG. 4C). Similarly, apoptosis was significantly inhibited in primary keratinocytes transiently down-regulated with an IGFBP7-shRNA as shown using the TUNEL assay (FIGS. 14A-B).

Decreased IGFBP7 does not Affect Keratinocyte Senescence—

No effect of IGFBP7-down-regulation on senescence rates in human keratinocytes was observed as determined by the expression of beta-galactosidase, a marker for cell senescence (FIG. 16).

Example 3

IGFBP7 is Involved in Calcium Induced Differentiation of Keratinocytes

Experimental Results

IGFBP7 is Required for Calcium-Induced Expression of Genes Associated with Keratinocyte Differentiation—

To investigate the role of IGFBP7 in epidermal homeostasis, the present inventors induced differentiation of HaCat cells expressing either IGFBP7-specific or control shRNA in the presence of 1.4 mM $Ca^{2+}$ medium as previously described (Boukamp P, Petrussevska R T, et al., 1988. Normal keratinization in a spontaneously immortalized aneuploid human keratinocyte cell line. J Cell Biol 106:761-771). Down-regulation of IGFBP7 was found to block the induction of three markers of keratinocyte differentiation, KRT10, involucrin (FIG. 5A) and loricrin (FIG. 11). In addition, cells down-regulated for IGFBP7 failed to demonstrate morphological changes characteristic of calcium-induced differentiation (FIGS. 9A-D). Similar results were obtained with primary keratinocytes (FIG. 5B), suggesting that IGFBP7 may also be involved in the regulation of keratinocyte differentiation.

IGFBP7 Regulates the Expression of Genes Associated with Calcium-Induced Keratinocyte Differentiation—

To further investigate this possibility at a broader level, the present inventors performed a global gene expression analysis to assess the effect of IGFBP7 down-regulation on the expression of genes differentially expressed in HaCat cells cultured under low and high extracellular calcium concentrations. It was found by the present inventors that IGFBP7 down-regulation significantly attenuated the expression of 99.6% and 76.2% of genes displaying more than 2.5-fold change in expression in response to an increase in extracellular calcium concentration in HaCat cells and primary keratinocytes respectively. A global pathway GO (Gene ontology) analysis of the two data sets (p value <0.01) show that several of the process terms found to be significantly enriched in the analysis were relevant to regulation of proliferation and differentiation (FIG. 5C). Taken together, these data suggest that IGFBP7 regulates the expression of genes associated with calcium-induced keratinocyte differentiation.

To assess the effect of IGFBP7 down-regulation on the expression of genes differentially expressed in HaCat cells cultured under low and high extracellular calcium concentrations, the present inventors calculated the fold change of all genes represented on the array (~48,000 transcripts) in response to an increased concentration of extracellular calcium in IGFBP7-down regulated cells and control cells (Tables 3 and 4 below; and FIGS. 15A-D). The genes were then sorted according to the differences (fold change of the fold changes) between the two data sets fold changes. The top 100 genes (100 up, 100 down) are listed in Tables 3 and 4 below.

TABLE 3

Top 100 genes whose calcium-induced regulation was most markedly down affected by IGFBP7 silencing

| Down index | Probe Id # | Gene Symbol | Fold Change* |
|---|---|---|---|
| 1 | 6940070 | SCGB1A1 | 16.3304 |
| 2 | 2470722 | LYNX1 | 11.431 |
| 3 | 6280576 | S100A8 | 7.3454 |
| 4 | 5050682 | SLC39A2 | 6.8848 |
| 5 | 2680475 | UBD | 6.1127 |
| 6 | 1260270 | ATP6V1B1 | 5.9157 |
| 7 | 6580437 | PLAT | 5.7885 |
| 8 | 4540520 | CLDN8 | 5.7463 |
| 9 | 1090064 | CD74 | 5.3426 |
| 10 | 4490356 | KRT4 | 4.8539 |
| 11 | 6020594 | GCNT3 | 4.5458 |
| 12 | 6520767 | TOP2A | 4.4445 |
| 13 | 7570440 | E2F2 | 4.2843 |
| 14* | 290544 | MMP13 | 4.1875 |
| 15* | 2640609 | S100P | 4.0117 |
| 16 | 1690301 | ABP1 | 3.9195 |
| 17 | 5290739 | FZD10 | 3.8779 |
| 18 | 5960427 | IQGAP3 | 3.8329 |
| 19 | 110040 | PNCK | 3.8256 |
| 20 | 3780326 | GBP2 | 3.7385 |
| 21 | 5570500 | ALDH3B2 | 3.659 |
| 22 | 3450497 | TRIM31 | 3.639 |
| 23 | 5390014 | ITLN2 | 3.5343 |
| 24* | 4590669 | SERPINB4 | 3.5168 |
| 25 | 2900471 | TTK | 3.4925 |
| 26 | 1850093 | TNFSF10 | 3.3984 |
| 27 | 5360463 | DEFB1 | 3.3324 |
| 28 | 6510168 | SAA2 | 3.3281 |
| 29 | 460072 | CDCA5 | 3.3026 |
| 30 | 7610343 | C6ORF173 | 3.2944 |
| 31 | 6270092 | DTL | 3.2647 |
| 32 | 2680370 | HLA-DRA | 3.2631 |
| 33 | 540128 | SLCO2A1 | 3.2501 |
| 34 | 2970437 | TLR5 | 3.2377 |
| 35 | 4150474 | KRT13 | 3.2271 |
| 36 | 1240333 | VTCN1 | 3.1957 |
| 37 | 6660414 | CEP55 | 3.1584 |
| 38 | 7320020 | C18ORF45 | 3.1258 |
| 39 | 6220450 | DHRS9 | 3.1112 |
| 40 | 6980458 | SNCAIP | 3.0914 |
| 41 | 1580524 | BARX2 | 3.078 |
| 42 | 2030730 | MMP12 | 3.0729 |
| 43 | 3610619 | ST6GALNAC1 | 3.06 |
| 44 | 6480500 | HLA-DPA1 | 3.0502 |
| 45 | 5080288 | MCM10 | 3.0425 |
| 46 | 10307 | CCL2 | 2.9786 |
| 47 | 3060605 | ASPM | 2.9758 |
| 48 | 6040379 | HLA-DRB4 | 2.9747 |
| 49 | 6290561 | HLA-DQA1 | 2.9632 |
| 50 | 1470750 | TJP3 | 2.9446 |
| 51 | 5340484 | CDC2 | 2.9338 |
| 52 | 2450603 | UBE2C | 2.901 |
| 53 | 3060736 | AURKB | 2.8951 |

TABLE 3-continued

Top 100 genes whose calcium-induced regulation was most markedly down affected by IGFBP7 silencing

| Down index | Probe Id # | Gene Symbol | Fold Change* |
|---|---|---|---|
| 54 | 3170497 | CRABP2 | 2.8724 |
| 55 | 5310128 | KRT15 | 2.8459 |
| 56 | 840612 | HMMR | 2.8269 |
| 57 | 3060056 | HAS3 | 2.8237 |
| 58 | 10215 | CD86 | 2.8135 |
| 59 | 2750632 | OLFM4 | 2.7965 |
| 60 | 5390594 | HCAP-G | 2.7914 |
| 61 | 7400162 | KIAA1199 | 2.7914 |
| 62 | 5870743 | HLA-DMB | 2.7763 |
| 63 | 620343 | SLPI | 2.7747 |
| 64 | 4010053 | HLA-DRB3 | 2.7716 |
| 65 | 5960128 | TAF15 | 2.7534 |
| 66 | 4880400 | VSNL1 | 2.7509 |
| 67 | 380538 | CDH5 | 2.7439 |
| 68 | 10524 | PRC1 | 2.7438 |
| 69 | 6900592 | MALL | 2.7319 |
| 70 | 3520066 | PDZK1IP1 | 2.7282 |
| 71 | 2970731 | RAET1G | 2.7194 |
| 72 | 2760164 | EVA1 | 2.7069 |
| 73 | 1820040 | SAA1 | 2.6988 |
| 74 | 5570253 | TROAP | 2.6965 |
| 75 | 6330152 | KIAA0101 | 2.6745 |
| 76 | 3370403 | C15ORF48 | 2.6686 |
| 77 | 5720647 | ADAM19 | 2.6423 |
| 78 | 7400097 | TCN1 | 2.6372 |
| 79 | 4250379 | FOS | 2.6193 |
| 80 | 6940280 | ORC1L | 2.6157 |
| 81 | 4920719 | TRIM22 | 2.5946 |
| 82 | 4290114 | NUSAP1 | 2.5688 |
| 83 | 6770594 | CD82 | 2.5585 |
| 84 | 6100091 | EGR2 | 2.5493 |
| 85 | 1090500 | KRT1 | 2.5451 |
| 86 | 2340541 | FGFR3 | 2.5427 |
| 87 | 5310079 | MAP3K8 | 2.5353 |
| 88 | 4540364 | SERPINB3 | 2.5315 |
| 89 | 2060196 | AQP3 | 2.5286 |
| 90 | 5220072 | CFB | 2.5099 |
| 91 | 6330484 | GPR110 | 2.5075 |
| 92 | 4040221 | SERPINB1 | 2.505 |
| 93 | 20465 | KLK11 | 2.4987 |
| 94 | 7160040 | PRIM1 | 2.4943 |
| 95 | 6620725 | KIF2C | 2.4837 |
| 96 | 6520167 | BIRC3 | 2.4812 |
| 97 | 6220554 | HS.25318 | 2.4578 |
| 98 | 5820360 | C10ORF99 | 2.444 |
| 99 | 7160706 | INDO | 2.4422 |
| 100 | 5810184 | SYTL2 | 2.4247 |

Table 3.
*Genes validated by qRT-PCR.
*Fold change (up or down) of IGFBP7 silencing affect on calcium-induced regulation was calculated using the following equation: [{wt(Ca+/Ca−)}/{silence IGFBP7 (Ca+/Ca−)}]

TABLE 4

Top 100 genes whose calcium-induced regulation was most markedly up affected by IGFBP7 silencing

| Up index | Probe Id # | Symbol | Fold Change* |
|---|---|---|---|
| 1 | 1010136 | HSPA6 | 31.4967 |
| 2 | 3120097 | RGS7 | 7.2332 |
| 3 | 3710035 | HMOX1 | 6.2995 |
| 4 | 4540575 | ARL4 | 4.742 |
| 5 | 4290370 | HS.570017 | 4.3452 |
| 6 | 2760239 | AKR1C3 | 4.1106 |
| 7 | 1470369 | CCL26 | 4.0743 |
| 8 | 4480010 | HS3ST2 | 3.8787 |
| 9 | 7050372 | TXNRD1 | 3.8565 |
| 10* | 4900541 | CYP1A1 | 3.7022 |
| 11 | 130709 | ABL2 | 3.5947 |
| 12* | 2100301 | INSIG1 | 3.5775 |
| 13 | 3400292 | PSG11 | 3.549 |

TABLE 4-continued

Top 100 genes whose calcium-induced regulation was most markedly up affected by IGFBP7 silencing

| Up index | Probe Id # | Symbol | Fold Change* |
|---|---|---|---|
| 14 | 630010 | ANKRD1 | 3.5442 |
| 15 | 4780475 | DUSP1 | 3.5115 |
| 16 | 4880593 | LOC648517 | 3.4567 |
| 17 | 4780376 | CDH2 | 3.4565 |
| 18 | 6250138 | PNLIPRP3 | 3.3927 |
| 19 | 6960634 | INSIG1 | 3.3512 |
| 20 | 7040719 | TNFSF15 | 3.3435 |
| 21 | 2970646 | SLC7A11 | 3.3424 |
| 22 | 6940524 | PDE5A | 3.3205 |
| 23 | 6040601 | CTH | 3.2527 |
| 24 | 7150603 | DNAJA4 | 3.1471 |
| 25 | 5860333 | F3 | 3.1227 |
| 26 | 5260193 | PSG5 | 3.1128 |
| 27 | 7200114 | CTGF | 3.1025 |
| 28 | 5860300 | HSPA1A | 2.9478 |
| 29 | 3190292 | TAGLN | 2.9395 |
| 30 | 130563 | HSD17B2 | 2.8586 |
| 31 | 5900367 | HS.553217 | 2.8318 |
| 32 | 780255 | HSPA1L | 2.8305 |
| 33 | 7610546 | HMFN0839 | 2.816 |
| 34 | 6580491 | PAPSS2 | 2.7948 |
| 35 | 3840253 | FAM46A | 2.7782 |
| 36 | 4150750 | DCBLD2 | 2.7549 |
| 37 | 6840022 | HS.387982 | 2.735 |
| 38 | 4890048 | ARL4 | 2.6492 |
| 39 | 5310184 | FGD3 | 2.6445 |
| 40 | 160132 | CREB5 | 2.6292 |
| 41 | 2640576 | SAMD4A | 2.6247 |
| 42 | 5870243 | ELL2 | 2.6161 |
| 43 | 1820068 | CPA4 | 2.6068 |
| 44 | 6980095 | IRS2 | 2.6066 |
| 45 | 3060465 | MAP2 | 2.6058 |
| 46 | 4730082 | LOC644760 | 2.5786 |
| 47 | 5670341 | LOC554223 | 2.5774 |
| 48 | 4290376 | RHOB | 2.5764 |
| 49 | 7510487 | AQP11 | 2.5697 |
| 50 | 20010 | DHCR7 | 2.5495 |
| 51 | 5050347 | DLC1 | 2.5445 |
| 52 | 4180524 | CA12 | 2.543 |
| 53 | 4880086 | ETV5 | 2.5405 |
| 54 | 6330315 | DST | 2.5404 |
| 55 | 1230528 | HSPH1 | 2.5257 |
| 56 | 2340093 | AFF4 | 2.5239 |
| 57 | 940142 | SQSTM1 | 2.5162 |
| 58 | 7160398 | INHBE | 2.5114 |
| 59 | 2650324 | ANXA10 | 2.5052 |
| 60 | 3400494 | PTPDC1 | 2.5032 |
| 61 | 2940255 | PLA2G4C | 2.4848 |
| 62 | 2100379 | PPP1R3C | 2.4559 |
| 63 | 7050451 | GCLM | 2.4486 |
| 64 | 2320538 | FADS3 | 2.4472 |
| 65 | 1940048 | OKL38 | 2.4467 |
| 66 | 6760735 | TRPV6 | 2.4313 |
| 67 | 510528 | VEGF | 2.4267 |
| 68 | 1050324 | LPIN1 | 2.4072 |
| 69 | 3130273 | GAB2 | 2.3723 |
| 70 | 1980240 | PLEKHC1 | 2.3577 |
| 71* | 780600 | KLK6 | 2.3436 |
| 72 | 2680711 | HKDC1 | 2.3371 |
| 73 | 3830133 | HS.556018 | 2.3197 |
| 74 | 6100228 | NFIL3 | 2.3145 |
| 75 | 520184 | RAB32 | 2.3115 |
| 76 | 380731 | TUBA1 | 2.3106 |
| 77 | 3850669 | LXN | 2.3094 |
| 78 | 150703 | ATF3 | 2.3052 |
| 79 | 780228 | RARB | 2.2983 |
| 80 | 2140192 | DKK1 | 2.2962 |
| 81 | 3440411 | HSPA1B | 2.2913 |
| 82 | 4760100 | PTHLH | 2.2861 |
| 83 | 2070672 | FIBCD1 | 2.2837 |
| 84 | 7210343 | HS.107418 | 2.2837 |
| 85 | 1470176 | TUBB2B | 2.2813 |
| 86 | 5960201 | SNAI2 | 2.2727 |
| 87 | 780692 | FLG | 2.2588 |
| 88 | 7510577 | HS.551128 | 2.2452 |

TABLE 4-continued

Top 100 genes whose calcium-induced regulation was most markedly up affected by IGFBP7 silencing

| Up index | Probe Id # | Symbol | Fold Change* |
|---|---|---|---|
| 89 | 7400692 | ISL1 | 2.2303 |
| 90 | 610639 | RAB3IL1 | 2.2282 |
| 91 | 6200095 | COL5A1 | 2.2199 |
| 92 | 5130309 | HS.159264 | 2.2186 |
| 93 | 6760170 | LOC338758 | 2.2184 |
| 94 | 1170576 | HS.575324 | 2.2136 |
| 95 | 4730195 | HIST1H4H | 2.2122 |
| 96 | 5810066 | LOC285989 | 2.2104 |
| 97 | 60121 | LOC399900 | 2.1984 |
| 98 | 580445 | NEXN | 2.1814 |
| 99 | 2260594 | NOLA1 | 2.1768 |
| 100 | 650709 | SLC2A6 | 2.1554 |

Table 4.
*Genes validated by qRT--□PCR.
*Fold change (up or down) of IGFBP7 silencing affect on calcium-induced regulation was calculated using the following equation: [{silence IGFBP7 (Ca+/Ca−)}/{wt (Ca+/Ca−)}].

Example 4

IGFBP7 Inhibits Proliferation and Induces Apoptosis of Keratinocytes

Experimental Results
Recombinant IGFBP7 Inhibits Proliferation and Induces Apoptosis in Human Keratinocytes—

To confirm the involvement of IGFBP7 in the regulation of keratinocyte proliferation and differentiation, the present inventors examined the effect of recombinant human IGFBP7 polypeptide (rIGFBP7) on primary keratinocyte cells. Addition of rIGFBP7 resulted in a decrease in viable cell counts in primary human keratinocyte cultures, as determined by the MTT assay (FIG. 6A). This observation was most probably accounted for by a decrease in cell proliferation as determined by the BrDU assay (FIG. 6B) as well as by an increase in keratinocyte apoptosis as shown in FIG. 6C. rIGFBP7 lacked significant effect on cell differentiation (data not shown).

Example 5

IGFBP7-Silencing Induces Phosphorylation of IRS1 and Erk in Keratinocytes

Experimental Results
Effect of IGFBP7 Downregulation on TGF-β and Insulin Signaling—

To investigate the signaling pathway(s) affected by IGFBP7 down-regulation, the present inventors used HaCat cells stably down-regulated for IGFBP7. IGFBP7 down-regulation was found to induce the phosphorylation of the insulin receptor associated-insulin receptor substrate 1 (IRS1) and of the tyrosine kinase ERK 1/2, suggesting interference with signaling through the insulin receptor (FIGS. 7A-D). In contrast, IGFBP7 did not influence SMAD 2/3 phosphorylation status (data not shown).

ERK Inhibition Attenuates Cell Proliferation Induced by IGFBP7 Down-Regulation—

To further investigate the involvement of ERK in IGFBP7-mediated cell proliferation primary keratinocytes which were transfected with IGFBP7 siRNA were treated with the ERK inhibitor PD98059 (120 μM for 72 hours, while refreshing the medium every 24 hours). As shown in FIG. 17, inhibition of ERK prevented the induction of keratinocyte proliferation observed in IGFBP-silenced cells.

Example 6

Down-Regulation of IGFBP7 in a Physiologically Relevant Model Induces a Psoriasis-Like Phenotype in the Absence of Immunological Elements The present inventors used a three-dimensional organotypic cell culture system to model the role of decreased IGFBP7 expression in the pathogenesis of psoriasis (FIGS. 18 and 19). In this model system, keratinocytes are grown at the air liquid interface on a support consisting of collagen and fibroblasts for up to 2 weeks. During this time, keratinocytes fully differentiate, forming a multilayered, cornified epithelium which faithfully replicates most physiological aspects of normal epidermal biology. The present inventors established the conditions necessary to grow such three-dimensional skin equivalents. Histological and immunohistochemical analyses confirmed the existence of a legitimate differentiation program in these cultures. At days 7 and 10 the skin equivalent showed the features of intact epidermal differentiation and presence of the main layers of epidermis: basal, spinous, granular and cornified layers and dermis. At day 12, the stratum corneum was thickened and desquamation, i.e., detachment of cornified keratinocytes, occurred (FIG. 20). IGFBP7 expression was found to increase with progressive stratification of the artificial epidermis (FIG. 21).

To confirm the physiological relevance of these findings in keratinocyte monolayers, the present inventors suppressed the expression of IGFBP7 by RNA interference in skin organotypic cultures. Proliferating keratinocytes were transfected with IGFBP7-specific or control small interfering RNAs by electroporation. Subsequently, the transfected cells were cultured as the epidermal component of an in vitro skin equivalent model on a support of collagen and fibroblasts at the air liquid interface. Punch biopsies were taken at 14 days of culture, formalin-fixed and processed for H&E staining. Punch biopsies were also taken at day 7 for RNA extraction, transcribed to cDNA and analyzed by qRT-PCR for IGFBP7 mRNA expression. IGFBP7 specific siRNA suppressed IGFBP7 expression to less than 60% of the normal level in skin equivalents as measured at day 7 (data not shown). The effect of siRNAs was sustained for at least 7 days in organotypic skin model (data not shown). H&E staining of skin equivalents downregulated for IGFBP7 revealed striking changes at day 14, including abnormal stratification, absence of granular layer, parakeratosis and marked hyperkeratosis (FIGS. 22A and B).

Example 7

Recombinant IGFBP7 Cures Psoriasis Ina Humanized Mouse Model

To assess the effect of IGFBP7 on psoriasis, the present inventors used a chimeric mouse model (FIG. 23). The model is based on the use of normal skin from healthy controls that is grafted onto beige-SCID mice. The grafts are then injected with NK/T cells isolated from psoriatic patients (Gilhar et al., 2002). The peripheral blood mononuclear cells isolated from psoriatic patients are cultured in NK complete medium [RPMI 1640, 10% human AB serum (Sigma-Aldrich, St Louis, Mo., USA), 1% glutamine, and 1% antibiotics penicillin/streptomycin (Biological Industries, Beit Haemek, Israel) and 100 U/ml IL-2 (Pepro Tech Inc., Rocky Hill, N.J., USA] during 3 weeks. Such cell lines express heterogeneous NK cell markers and exhibit NK cytotoxicity. Four weeks after skin engraftment the NK cells are injected into human skin explants on beige-SCID mice lacking T-, B- and NK-cells and within next 4 weeks a skin phenotype indistinguishable from genuine human psoriasis is developed (Gilhar et al., 2002).

In the experimental system used herein, two weeks after NK injection (6 weeks after engraftment) 3 groups of mice were treated with intralesional PBS, topical dexamethasone and intralesional IGFBP7. The effect of the treatment was monitored by histology analysis two weeks after the treatment (8 weeks after engraftment).

As expected, all five mice treated with PBS displayed typical psoriatic features on histology including acanthosis (thickening of the stratum spinosum), elongation of rete ridges, parakeratosis (retention of nuclei in cells of the stratum corneum), and hyperkeratosis (thickening of stratum corneum) and a dense mononuclear infiltrate in the dermis (FIG. 24). All these characteristics were absent in all five mice treated with dexamethasone (FIG. 25). Dexamethasone, a synthetic steroid, acts as an anti-inflammatory and immunosuppressant agent. In the group of mice treated with rIGFBP7, three mice showed full recovery (FIG. 26), one mouse recovered partially (50%) and one animal only showed features of psoriasis on histology. Interestingly, while treatment with rIGFBP7 reversed the psoriatic phenotype in the epidermis, mononuclear infiltrating cells could still be seen in the dermis albeit in smaller numbers, suggesting that IGFBP7 mainly targets the epidermal component of the disease pathogenesis.

Analysis of Results

IGFBP7 Regulates Keratinocyte Proliferation, Differentiation and Apoptosis—

Insulin-like growth factor (IGF)-binding protein (IGFBP) 7 belongs to IGFBP superfamily, which is involved in the regulation of IGF signaling. IGFBP7 has been implicated in a number of processes such as modulation of sex hormone release, neutralization of mitogenic signals, induction of senescence, regulation of adhesion and angiogenesis in cancer cells. In addition, IGFBP7 was found to be down-regulated in the psoriatic epidermis, with UVB phototherapy restoring its expression to normal (Hochberg M., et al., 2007).

The present inventors studied the effect of IGFBP7 on 4 parameters of potential relevance to psoriasis cardinal features: cell proliferation, differentiation, apoptosis and senescence. The present inventors found that low IGFBP7 expression triggers cell proliferation, blocks differentiation, decreases apoptosis and has no effect on senescence rates both in HaCat cells and primary human keratinocytes. Conversely, rIGFBP7 was found to induce cell apoptosis and to decrease cell proliferation.

The role of IGFBP7 in the regulation of keratinocyte proliferation and differentiation, which are abnormal in psoriasis, was studies in an in vitro system in which IGFBP7 is downregulated. HaCat cells and primary human keratinocytes were transfected with IGFBP7-specific shRNA-expressing lentiviral vectors. Down-regulation of IGFBP7 was found to enhance keratinocyte proliferation in both systems. In addition, IGFBP7 down-regulation was associated with a marked decrease in keratinocyte susceptibility to TNF-α-induced apoptosis but lacked any effect on senescence. Down-regulation of IGFBP7 was also found to block expression of genes associated with calcium-induced differentiation of human keratinocytes.

In addition, recombinant IGFBP7 was found to significantly inhibit keratinocyte proliferation and enhance keratinocyte apoptosis. These data position IGFBP7 as a major regulator of keratinocyte proliferation and differentiation, suggesting a potential role for this protein in the pathophysiology and treatment of hyperproliferative disorders such as psoriasis.

Using an ex vivo model the present inventors showed that decrease in IGFBP7 results in a psoriasis phenotype (Example 6; FIGS. 22A-B). In addition, using an in vivo model, the present inventors demonstrate that recombinant IGFBP7 cures psoriasis in a human-mouse chimeric model (FIGS. 23-26; Example 7).

In conclusion, these data position IGFBP7 as a key regulator of keratinocyte differentiation and proliferation, and therefore suggest this protein as an attractive target for the treatment of various pathologies associated with keratinocyte abnormal proliferation and differentiation.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

Additional References are Cited Text

Akaogi K, Okabe Y, Sato J, Nagashima Y, Yasumitsu H, Sugahara K, et al. (1996) Specific accumulation of tumor-derived adhesion factor in tumor blood vessels and in capillary tube-like structures of cultured vascular endothelial cells. ProcNatlAcadSciUSA 93:8384-8389.

Bernerd F, Magnaldo T, Darmon M (1992) Delayed onset of epidermal differentiation in psoriasis. J Invest Dermatol 98:902-910.

Bovenschen H J, Seyger M M, Van de Kerkhof P C (2005) Plaque psoriasis vs. atopic dermatitis and lichen planus: a comparison for lesional T-cell subsets, epidermal proliferation and differentiation. Br J Dermatol 153:72-78.

Bowen A R, Hanks A N, Murphy K J, Florell S R, Grossman D (2004) Proliferation, apoptosis, and survivin expression in keratinocytic neoplasms and hyperplasias. Am J Dermatopathol 26:177-181.

Burger A M, Leyland-Jones B, Banerjee K, Spyropoulos D D, Seth A K (2005) Essential roles of IGFBP-3 and IGFBP-rP1 in breast cancer. EurJCancer 41:1515-1527.

Degeorges A, Wang F, Frierson H F, Jr., Seth A, Sikes R A (2000) Distribution of IGFBP-rP1 in normal human tissues. JHistochemCytochem 48:747-754.

Candille S I, Kaelin C B, Cattanach B M, Yu B, Thompson D A, Nix M A, Kerns J A, Schmutz S M, Millhauser G L, Barsh G S. A-defensin mutation causes black coat color in domestic dogs. Science. 2007 Nov. 30; 318(5855):1418-23.

Chamorro C I, Weber G, Gronberg A, Pivarcsi A, Stable M. The human antimicrobial peptide LL-37 suppresses apoptosis in keratinocytes. J Invest Dermatol. 2009 April; 129(4):937-44.

Duncan, Janet I. Differential Inhibition of Cutaneous T-Cell-Mediated Reactions and Epidermal Cell Proliferation by Cyclosporin A, FK-506, and Rapamycin. Journal of Investigative Dermatology 1994 (102): 84-88.

Gazel A, Ramphal P, Rosdy M, De W B, Tornier C, Hosein N, et al. (2003) Transcriptional profiling of epidermal keratinocytes: comparison of genes expressed in skin, cultured keratinocytes, and reconstituted epidermis, using large DNA microarrays. JInvest Dermatol 121:1459-1468.

Genua M, Pandini G, Cassarino M F, Messina R L, Frasca F (2009) c-Abl and insulin receptor signalling. Vitam Horm 80:77-105.

Griffiths C E, Barker J N (2007) Pathogenesis and clinical features of psoriasis. Lancet 370:263-271.

Gunduz K, Demireli P, Vatansever S, Inanir I (2006) Examination of bcl-2 and p53 expressions and apoptotic index by TUNEL method in psoriasis. J Cutan Pathol 33:788-792.

Haider A S, Peters S B, Kaporis H, Cardinale I, Fei J, Ott J, et al. (2006) Genomic analysis defines a cancer-specific gene expression signature for human squamous cell carcinoma and distinguishes malignant hyperproliferation from benign hyperplasia. J Invest Dermatol 126:869-881.

Hochberg M, Zeligson S, Amariglio N, Rechavi G, Ingber A, Enk C D (2007) Genomic-scale analysis of psoriatic skin reveals differentially expressed insulin-like growth factor-binding protein-7 after phototherapy. BrJDermatol 156: 289-300.

Komine M, Karakawa M, Takekoshi T, Sakurai N, Minatani Y, Mitsui H, Tada Y, Saeki H, Asahina A, Tamaki K. Early inflammatory changes in the "perilesional skin" of psoriatic plaques: is there interaction between dendritic cells and keratinocytes? J Invest Dermatol. 2007 August; 127(8):1915-22.

Krueger J G, Bowcock A (2005) Psoriasis pathophysiology: current concepts of pathogenesis. Ann Rheum Dis 64 Suppl 2:ii30-36.

Krüger-Krasagakis S, Galanopoulos V K, Giannikaki L, Stefanidou M, Tosca A D. Programmed cell death of keratinocytes in infliximab-treated plaque-type psoriasis. Br J. Dermatol. 2006 March; 154(3):460-6.

Lande Roberto, Josh Gregorio, Valeria Facchinetti, Bithi Chatterjee, Yi-Hong Wang, Bernhard Homey, Wei Cao, Yui-Hsi Wang, Bing Su, Frank O. Nestle, et al. Plasmacytoid dendritic cells sense self-DNA coupled with antimicrobial peptide. Nature 449, 564-569 (16 Sep. 2007)

Laporte M, Galand P, Fokan D, de Graef C, Heenen M (2000) Apoptosis in established and healing psoriasis. Dermatology 200:314-316.

Lopez-Bermejo A, Khosravi J, Corless C L, Krishna R G, Diamandi A, Bodani U, et al. (2003) Generation of anti-insulin-like growth factor-binding protein-related protein 1 (IGFBP-rP1/MAC25) monoclonal antibodies and immunoassay: quantification of IGFBP-rP1 in human serum and distribution in human fluids and tissues. JClinEndocrinolMetab 88:3401-3408.

Lowes M A, Bowcock A M, Krueger J G (2007) Pathogenesis and therapy of psoriasis. Nature 445:866-873.

McKay I A, Leigh I M (1995) Altered keratinocyte growth and differentiation in psoriasis. ClinDermatol 13:105-114.

Nair R P, Duffin K C, Helms C, Ding J, Stuart P E, Goldgar D, et al. (2009) Genome-wide scan reveals association of psoriasis with IL-23 and NF-kappaB pathways. Nat Genet. 41:199-204.

Nair R P, Stuart P E, Nistor I, Hiremagalore R, Chia N V, Jenisch S, et al. (2006) Sequence and haplotype analysis supports HLA-C as the psoriasis susceptibility 1 gene. Am J Hum Genet. 78:827-851.

Neely E K, Morhenn V B, Hintz R L, Wilson D M, Rosenfeld R G (1991) Insulin-like growth factors are mitogenic for human keratinocytes and a squamous cell carcinoma. J Invest Dermatol 96:104-110.

Nickoloff B J, Bonish B K, Marble D J, Schriedel K A, DiPietro L A, Gordon K B, et al. (2006) Lessons learned from psoriatic plaques concerning mechanisms of tissue repair, remodeling, and inflammation. JInvestigDermatolSympProc 11:16-29.

Raj D, Brash D E, Grossman D (2006) Keratinocyte apoptosis in epidermal development and disease. J Invest Dermatol 126:243-257.

Rahmoun M, Molès JP, Pedretti N, Mathieu M, Fremaux I, Raison-Peyron N, Lecron J C, Yssel H, Pène J. Cytokine-induced CEACAM1 expression on keratinocytes is characteristic for psoriatic skin and contributes to a prolonged lifespan of neutrophils. J Invest Dermatol. 2009 March; 129(3):671-81.

Ruan W, Xu E, Xu F, Ma Y, Deng H, Huang Q, et al. (2007) IGFBP7 plays a potential tumor suppressor role in colorectal carcinogenesis. Cancer BiolTher 6:354-359.

Sadagurski M, Nofech-Mozes S, Weingarten G, White M F, Kadowaki T, Wertheimer E (2007) Insulin receptor substrate 1 (IRS-1) plays a unique role in normal epidermal physiology. JCell Physiol 213:519-527.

Sato Y, Chen Z, Miyazaki K (2007) Strong suppression of tumor growth by insulin-like growth factor-binding protein-related protein 1/tumor-derived cell adhesion factor/mac25. Cancer Sci 98:1055-1063.

Shon et al. Exp Dermatol. 2008 August; 17(8):703-12.

Vissers W H, van Vlijmen I, van Erp P E, de Jong E M, van de Kerkhof P C (2008) Topical treatment of mild to moderate plaque psoriasis with 0.3% tacrolimus gel and 0.5% tacrolimus cream: the effect on SUM score, epidermal proliferation, keratinization, T-cell subsets and HLA-DR expression. Br J Dermatol 158:705-712.

Wajapeyee N, Serra R W, Zhu X, Mahalingam M, Green M R (2008) Oncogenic BRAF induces senescence and apoptosis through pathways mediated by the secreted protein IGFBP7. Cell 132:363-374.

Wertheimer E, Spravchikov N, Trebicz M, Gartsbein M, Accili D, Avinoah I, et al. (2001) The regulation of skin proliferation and differentiation in the IR null mouse: implications for skin complications of diabetes. Endocrinology 142:1234-1241.

Wertheimer E, Trebicz M, Eldar T, Gartsbein M, Nofeh-Moses S, Tennenbaum T (2000) Differential roles of insulin receptor and insulin-like growth factor-1 receptor in differentiation of murine skin keratinocytes. JInvest Dermatol 115:24-29.

Wilson H M, Birnbaum R S, Poot M, Quinn L S, Swisshelm K (2002) Insulin-like growth factor binding protein-related protein 1 inhibits proliferation of MCF-7 breast cancer cells via a senescence-like mechanism. Cell Growth Differ 13:205-213.

Wrone-Smith T, Mitra R S, Thompson C B, Jasty R, Castle V P, Nickoloff B J (1997) Keratinocytes derived from psoriatic plaques are resistant to apoptosis compared with normal skin. AmJPathol 151:1321-1329.

Yamanaka Y, Wilson E M, Rosenfeld R G, Oh Y (1997) Inhibition of insulin receptor activation by insulin-like growth factor binding proteins. JBiolChem 272:30729-30734.

Yang C F, Hwu W L, Yang L C, Chung W H, Chien Y H, Hung C F, et al. (2008) A promoter sequence variant of ZNF750 is linked with familial psoriasis. J Invest Dermatol 128: 1662-1668.

Yang J, Li Y, Liu Y Q, Long J W, Tian F, Dong J, et al. (2009) Expression of antiapoptotic protein c-FLIP is upregulated in psoriasis epidermis. Eur J Dermatol 19:29-33.

Zenz R, Eferl R, Scheinecker C, Redlich K, Smolen J, Schonthaler H B, et al. (2008) Activator protein 1 (Fos/Jun) functions in inflammatory bone and skin disease. Arthritis ResTher 10:201.

Zenz R, Wagner E F (2006) Jun signalling in the epidermis: From developmental defects to psoriasis and skin tumors. IntJBiochemCellBiol 38:1043-1049.

Zhang X J, Huang W, Yang S, Sun L D, Zhang F Y, Zhu Q X, et al. (2009) Psoriasis genome-wide association study identifies susceptibility variants within LCE gene cluster at 1q21. Nat Genet. 41:205-210.

Zenz R, Eferl R, Kenner L, Florin L, Hummerich L, Mehic D, Scheuch H, Angel P, Tschachler E, Wagner E F. Psoriasis-like skin disease and arthritis caused by inducible epidermal deletion of Jun proteins. Nature. 2005 Sep. 15; 437 (7057):369-75.

Koegel H, von Tobel L, Schafer M, Alberti S, Kremmer E, Mauch C, Hohl D, Wang X J, Beer H D, Bloch W, Nordheim A, Werner S. Loss of serum response factor in keratinocytes results in hyperproliferative skin disease in mice. J Clin Invest. 2009 April; 119(4):899-910. doi: 10.1172/JCI37771. Epub 2009 Mar. 23.

What is claimed is:

1. A method of treating a pathology characterized by hyperproliferative keratinocytes comprising administering to a subject in need thereof a therapeutically effective amount of an insulin-like growth factor binding protein 7 (IGFBP7) polypeptide, thereby treating the pathology characterized by hyperproliferative keratinocytes.

2. The method of claim 1, wherein said pathology characterized by said hyperproliferative keratinocytes is psoriasis.

3. The method of claim 1, wherein said pathology characterized by said hyperproliferative keratinocytes is selected from the group consisting of psoriasis, lichen planus, pityriasis rubra pilaris (PRP), papulosquamous disease, dermatitis and lichen simplex chronicus.

4. The method of claim 3, wherein said dermatitis is selected from the group consisting of atopic dermatitis and contact dermatisis.

5. The method of claim 1, further comprising treating the subject with light therapy.

6. The method of claim 5, further comprising treating the subject with an agent suitable for topical administration, wherein said agent is selected from the group consisting of a corticosteroid, a vitamin D analogue or derivative, anthralin, topical retinoid, calcineurin inhibitor, salicylic acid, coal tar and a moisturizer.

7. The method of claim 5, wherein said light therapy is selected from the group consisting of sun light phototherapy, UVB phototherapy, narrowband UVB phototherapy, photochemotherapy, PUVA and excimer laser.

8. The method of claim 5, further comprising treating the subject with an agent suitable for systemic administration, wherein said agent is selected from the group consisting of a retinoid, an immunosuppressive drug, an immune-targeting biologic agent, an immunotoxin, and a tumor necrosis factor (TNF) blocking agent.

9. A method of treating a pathology characterized by hyperproliferative keratinocytes comprising administering to a subject in need thereof a therapeutically effective amount of a polynucleotide delivery vehicle, wherein said delivery vehicle contains a polynucleotide that encodes an insulin-like growth factor binding protein 7 (IGFBP7) polypeptide, thereby treating the pathology characterized by hyperproliferative keratinocytes.

10. The method of claim 9, wherein said pathology characterized by said hyperproliferative keratinocytes is psoriasis.

11. The method of claim 9, wherein said pathology characterized by said hyperproliferative keratinocytes is selected from the group consisting of psoriasis, lichen planus, pityriasis rubra pilaris (PRP), papulosquamous disease, dermatitis and lichen simplex chronicus.

12. The method of claim 9, further comprising treating the subject with light therapy.

13. The method of claim 12, wherein said light therapy is selected from the group consisting of sun light phototherapy, UVB phototherapy, narrowband UVB phototherapy, photochemotherapy, PUVA and excimer laser.

* * * * *

SEQUENCE LISTING

```
<160> NUMBER OF SEQ ID NOS: 46

<210> SEQ ID NO 1
<211> LENGTH: 1124
<212> TYPE: DNA
<213> ORGANISM: Homo sapiens

<400> SEQUENCE: 1
gccgctgcca ccgcacccg ccatggagcg gccgtcgctg cgcgccctgc tcctcggcgc      60
cgctgggctg ctgctcctgc tcctgcccct ctcctcttcc tcctcttcgg acacctgcgg    120
cccctgcgag ccggcctcct gcccgcccct gccccgctg gctgcctgc tgggcgagac     180 ccgcgacgcg tgcggctgct gccctatgtg cgcccgcggc gagggcgagc cgtgcggggg    240
tggcggcgcc ggcagggggt actgcgcgcc gggcatggag tgcgtgaaga gccgcaagag    300
gcggaagggt aaagccgggg cagcagccgg cggtccgggt gtaagcggcg tgtgcgtgtg    360
caagagccgc tacccggtgt gcggcagcga cggcaccacc tacccgagcg gctgccagct    420
gcgcgccgcc agccagaggg ccgagagccg cggggagaag gccatcaccc aggtcagcaa    480
gggcacctgc gagcaaggtc cttccatagt gacgccccc aaggacatct ggaatgtcac    540
tggtgcccag gtgtacttga gctgtgaggt catcggaatc ccgacacctg tcctcatctg    600
gaacaaggta aaaggggtc actatggagt tcaaggaca gaactcctgc ctggtgaccg      660
ggacaacctg gccattcaga cccggggtgg cccagaaaag catgaagtaa ctggctgggt    720
gctggtatct cctctaagta aggaagatgc tggagaatat gagtgccatg catccaattc    780
ccaaggacag gcttcagcat cagcaaaaat tacagtggtt gatgccttac atgaaatacc    840
agtgaaaaaa ggtgaaggtg ccgagctata aacctccaga atattattag tctgcatggt    900
taaaagtagt catggataac tacattacct gttcttgcct aataagtttc ttttaatcca    960
atccactaac actttagtta tattcactgg ttttacacag agaaatacaa aataaagatc   1020
acacatcaag actatctaca aaatttatt atatatttac agaagaaaag catgcatatc   1080
attaaacaaa taaatactt tttatcacaa aaaaaaaaaa aaaa                     1124

<210> SEQ ID NO 2
<211> LENGTH: 1171
<212> TYPE: DNA
<213> ORGANISM: Canis familiaris

<400> SEQUENCE: 2
cgggccgggc ggggcgccgg gtttaaggct cgggcccgcg gggcccccctc agtcgcgctc    60 ccgcccgccg ccgcgcccag ccatggagcg gccgccgctg cgcgccctgc tgctcggcgc   120
```

```
cgccggggtg ctgctcctgc tcctgcccct ctcctcttcc tcctcttcgg acgcctgcgg    180 ccccctgcgcg ccggccgcct gcccgcccct gccccgcgg ggctgcccgc tgggcgagac    240
ccgcgacgcg tgcggctgct gcccggtgtg cgcgcgcggc gagggcgagc cgtgcggggg    300
cggcggcgcc ggcaggggc actgcgcgcc gggcatggag tgcgtgaaga gccgcaagag    360
gcggaagggt aaagccgggg cagcagccgg cggctcggcg gcgagcggcg tgtgcgtgtg    420
caagagccgc tacccggtgt gcggcagcga cggcgtcacc tacccagcg gctgccagct    480 gcgcgccgcc agcctgcggg ccgagagccg cggggagaag gccgtcaccc aggtcagcaa    540 gggcaccctgc gagcaaggtc cttccattgt gacaccccc aaggacatct ggaatgtcac    600
tggcgcccag gtgtacttga gctgtgaggt catcggaatc ccaaccctg tcctcatctg    660 gaacaaggta aaaggggta actatggagt tcaaaggaca gaactcttgc ctggtgaccg    720
ggacaacctg gctattcaga cccggggtgg cccagaaaag catgaagtca ctggttgggt    780
gctggtatct cctctcagta aggaggatgc tggagaatac gagtgccatg catccaattc    840
ccaaggacag gcttcagcat cagcaaaaat cacagtggtt gatgccttac atgaaatacc    900
agtgaaaaaa ggtgaaggtg ctgacctata aactgcagaa tgtattaatc tgcatcacta    960
aaagtagtcc tggtaactac agcctctgtt cttgcctaat aaccagtttc ttttcatcca   1020
gtccactaac gcttagttat atattcactg gttttacata aggaaatcc aaaataaaga   1080 taacacatca agactatcta caaaatttta ttgtctattt acagaagaaa agcatgcatg   1140
taattaaaat caataaaatg ctttctctca c                                   1171
```

<210> SEQ ID NO 3
<211> LENGTH: 282
<212> TYPE: PRT
<213> ORGANISM: Canis familiaris

<400> SEQUENCE: 3

```
Met Glu Arg Pro Pro Leu Arg Ala Leu Leu Gly Ala Ala Gly Val
1               5                   10                  15

Leu Leu Leu Leu Leu Pro Leu Ser Ser Ser Ser Ser Asp Ala Cys
                20                  25                  30

Gly Pro Cys Ala Pro Ala Ala Cys Pro Leu Pro Pro Arg Gly Cys
            35                  40                  45

Pro Leu Gly Glu Thr Arg Asp Ala Cys Gly Cys Pro Val Cys Ala
        50                  55                  60

Arg Gly Glu Gly Glu Pro Cys Gly Gly Gly Ala Gly Arg Gly His
65                  70                  75                  80

Cys Ala Pro Gly Met Glu Cys Val Lys Ser Lys Arg Arg Lys Gly
                85                  90                  95

Lys Ala Gly Ala Ala Gly Gly Ser Ala Ala Ser Gly Val Cys Val
            100                 105                 110

Cys Lys Ser Arg Tyr Pro Val Cys Gly Ser Asp Gly Val Thr Tyr Pro
        115                 120                 125

Ser Gly Cys Gln Leu Arg Ala Ala Ser Leu Arg Ala Glu Ser Arg Gly
    130                 135                 140

Glu Lys Ala Val Thr Gln Val Ser Lys Gly Thr Cys Glu Gln Gly Pro
145                 150                 155                 160

Ser Ile Val Thr Pro Pro Lys Asp Ile Trp Asn Val Thr Gly Ala Gln
                165                 170                 175

Val Tyr Leu Ser Cys Glu Val Ile Gly Ile Pro Thr Pro Val Leu Ile
            180                 185                 190
```

```
Trp Asn Lys Val Lys Arg Gly Asn Tyr Gly Val Gln Arg Thr Glu Leu
        195                 200                 205

Leu Pro Gly Asp Arg Asp Asn Leu Ala Ile Gln Thr Arg Gly Gly Pro
    210                 215                 220

Glu Lys His Glu Val Thr Gly Trp Val Leu Val Ser Pro Leu Ser Lys
225                 230                 235                 240

Glu Asp Ala Gly Glu Tyr Glu Cys His Ala Ser Asn Ser Gln Gly Gln
                245                 250                 255

Ala Ser Ala Ser Ala Lys Ile Thr Val Val Asp Ala Leu His Glu Ile
        260                 265                 270

Pro Val Lys Lys Gly Glu Gly Ala Asp Leu
        275                 280

<210> SEQ ID NO 4
<211> LENGTH: 3226
<212> TYPE: DNA
<213> ORGANISM: Pan troglodytes

<400> SEQUENCE: 4
```

| | | | |
|---|---|---|---|
| atgcacgctg cagtgttaca cgttcagtta aaaagtgaaa gcaacttcca tgtctgcatc | | | 60 |
| ggagaggcca gtgttcctgg aagagaggc tttcaagttg agtttgcaga ggacttcgca | | | 120 |
| gaaagactga ggaagagtcc accgtttgta tcaaaaacct cctggaatgc tggtgaagac | | | 180 |
| tgggggcgct ttaggtgcct ccgtggcagc tccaacgagg aaggagctgg acccctgct | | | 240 |
| cctctcagct gcgctctgga gggcgagcag ttcagcaaga actcaaaaca agggcacagc | | | 300 |
| tctcacacgg attccagcct gctgggcgag acccgcgacg cgtgcggctg ctgcccgatg | | | 360 |
| tgcgcccgcg cgagggcga gccgtgcggg ggtggcggtg caggcagggg gtactgcgcg | | | 420 |
| ccgggcatgg agtgcgtcaa gagccgcaag aggcggaagg gtaaagccgg gcagcagcc | | | 480 |
| ggcggtccgg gtgtaagcgg cgtgtgcgtg tgcaagagcc gctacccggt gtgcggcagc | | | 540 |
| gacggcacca cctacccgag cggctgccag ctgcgcgccg ccagccagag ggccgagagc | | | 600 |
| cgcggggaga aggccatcac ccaggtcagc aagggcacct gcgagcaagg tccttccata | | | 660 |
| gtgacgcccc ccaaggacat ctggaatgtc actggtgccc aggtgtactt gagctgtgag | | | 720 |
| gtcatcggaa tcccgacacc tgtcctcatc tggaacaagg taaaaggggt cactatgga | | | 780 |
| gttcaaagga cagaactcct gcctggtgac cgggacaacc tggccattca gacccggggt | | | 840 |
| ggcccagaaa agcatgaagt aactggctgg gtgctggtat ctcctctaag taaggaagat | | | 900 |
| gctggagaat atgagtgcca tgcatccaat tcccaaggac aggcttcagc atcagcaaaa | | | 960 |
| attacagtgg ttgatgcctt acatgaaata ccagtgaaaa aggtgaaggt gccgagcta | | | 1020 |
| taaacctcca gaatattatt agtctgcatg gttaaaagta gtcatggata actacattac | | | 1080 |
| ctgttcttgc ctaataagtt tcttttaatc caatccacta acactttagt tatattcact | | | 1140 |
| ggttttacac agagaaatac aaaataaaga tcacacatca agactatcta caaaaattta | | | 1200 |
| ttatatattt acagaagaaa agcatgcata tcattaaaca aataaaatac tttttatcac | | | 1260 |
| aacacaatac atatttgtca ttttaaaaa gccacacaat agaaacaaga caccaagata | | | 1320 |
| tttaattatc ttgttgactc ctgtaaaata gctaaacact catcattcgc ggtgcaatac | | | 1380 |
| tcatagacat aagttcctga acaatagtt tgcatgcata aggcattcgc accaaagaaa | | | 1440 |
| tctgaaaaga aaaacaaat ggtaattagc agaattgtac tgaagtgacc ccacttctct | | | 1500 |
| accccagaaa aagacaaaga tctggtactg tagataatga ataaatgagt ggagctgaga | | | 1560 |

```
acacacattc tgctacctca gcttatggtg gttctttctc ctagtaggct ttggtatttt    1620
acccattctg ccagacataa tttatattca cccacctcaa ctaaaaggtt ttcaaaaact    1680
cattgtttaa aatcccttgt acaaagtctt attatttcca aaagatgaat agcttagaga    1740
aattaccaca ctaaaaccta aactggtttt tagaaaaatc gaattatctt ttccttattt    1800
agaactagga atcttacaga agcatgctat caaaattgtg aaaatgccaa tctgttccac    1860
cacactaaat ctgcctggat agaccaacac agtttcctct aaacaaatat caacagccag    1920
taaagtctat acacacctgg gttttattgc ggcagcccct gcattcatat gtatgggtcc    1980
tggtgttggc aatcgccatt attccacaaa gattgcaaac atgaacctga tatggatctg    2040
atgcctcaaa caatctttcc cttaaaaact gggctgctcc atgggcaatc tgacaatctc    2100
gttccatttc tccaaaacgc aggccaccat cactgttaag aggaaaaaat tattactttg    2160
tacttatttt ttattataaa caccgccttg aataatggca aggtggaga ataatatttg    2220 caaagacgga gaactaggct ctaattttta taccctagca ttctctctat tggtggggag    2280
aggagaagtc taccaactat ttgacgtgca ttagaaagtc cccaaatggg ctaagcaaag    2340
tggctcaccc ctgtaatccc agcactttgg gaagcggact gggtgggtct cttgagctca    2400
ggagcctggg caacatggcg agaccccatc tctattttt aacaaataaa aataaaaaca    2460
gaaggactcc ccaaatggag tggatacatt agattcttaa gtagagcatt taattttcct    2520
cataagacac aataaagcat agagtggagg ttcatcatgc tatcatttaa ctttctagaa    2580
ttcaactcta tactaaaaaa atgaataatg aaaagacaa tctaaataag gcagcttgtc    2640
aatggaatga ctgtcccagg caatcaacct tgaaatcata atacatgtt ggctgaagta    2700 atggaaagaa caggtaaatg ataataggtt tccccaacat aagaagtgaa ataaatgcat    2760
tattcagatg tccaggcaaa tagatggtga tggcttcctt aacatactta atatccaaaa    2820
tacacaaaat aaaaccaatg ggtttataat gatattccac caaaacaaaa aaatcattgg    2880
tcgacttcgg accactgatc tggatgatta gacaaccagc tcactatttt gaaaactggt    2940
aaataaagag aatcaagcat ttattcctgc ccttactata agaacaacat cactaggtaa    3000
ccaaacagtt gaggaaacaa agttttagaa gtagtctggc taaaaactga agaaggactg    3060
agaaaaaata gaatggtatc agttggaaat cgctatttaa ttaaggtctt tagtaatagc    3120
tgctaaaatc ataaaaagaa aggcaaccag atactggaag tatagaatac cacctataaa    3180
gtattactgc caaaaaactc aaaccctaaa tctcaagcct caagat                   3226
```

<210> SEQ ID NO 5
<211> LENGTH: 340
<212> TYPE: PRT
<213> ORGANISM: Pan troglodytes

<400> SEQUENCE: 5

```
Met His Ala Ala Val Leu His Val Gln Leu Lys Ser Glu Ser Asn Phe
1               5                   10                  15

His Val Cys Ile Gly Glu Ala Ser Val Pro Gly Lys Arg Gly Phe Gln
            20                  25                  30

Val Glu Phe Ala Glu Asp Phe Ala Glu Arg Leu Arg Lys Ser Pro Pro
        35                  40                  45

Phe Val Ser Lys Thr Ser Trp Asn Ala Gly Glu Asp Trp Gly Arg Phe
    50                  55                  60

Arg Cys Leu Arg Gly Ser Ser Asn Glu Glu Gly Ala Gly Thr Pro Ala
65                  70                  75                  80
```

```
            Pro Leu Ser Cys Ala Leu Glu Gly Glu Gln Phe Ser Lys Asn Ser Lys
                         85                  90                  95

Gln Gly His Ser Ser His Thr Asp Ser Ser Leu Leu Gly Glu Thr Arg
                        100                 105                 110

Asp Ala Cys Gly Cys Cys Pro Met Cys Ala Arg Gly Glu Gly Glu Pro
                        115                 120                 125

Cys Gly Gly Gly Gly Ala Gly Arg Gly Tyr Cys Ala Pro Gly Met Glu
                        130                 135                 140

Cys Val Lys Ser Arg Lys Arg Arg Lys Gly Ala Gly Ala Ala Ala
            145                 150                 155                 160

Gly Gly Pro Gly Val Ser Gly Val Cys Val Cys Lys Ser Arg Tyr Pro
                        165                 170                 175

Val Cys Gly Ser Asp Gly Thr Thr Tyr Pro Ser Gly Cys Gln Leu Arg
                        180                 185                 190

Ala Ala Ser Gln Arg Ala Glu Ser Arg Gly Glu Lys Ala Ile Thr Gln
                        195                 200                 205

Val Ser Lys Gly Thr Cys Glu Gln Gly Pro Ser Ile Val Thr Pro Pro
                        210                 215                 220

Lys Asp Ile Trp Asn Val Thr Gly Ala Gln Val Tyr Leu Ser Cys Glu
            225                 230                 235                 240

Val Ile Gly Ile Pro Thr Pro Val Leu Ile Trp Asn Lys Val Lys Arg
                        245                 250                 255

Gly His Tyr Gly Val Gln Arg Thr Glu Leu Leu Pro Gly Asp Arg Asp
                        260                 265                 270

Asn Leu Ala Ile Gln Thr Arg Gly Gly Pro Glu Lys His Glu Val Thr
                        275                 280                 285

Gly Trp Val Leu Val Ser Pro Leu Ser Lys Glu Asp Ala Gly Glu Tyr
                        290                 295                 300

Glu Cys His Ala Ser Asn Ser Gln Gly Gln Ala Ser Ala Ser Ala Lys
            305                 310                 315                 320

Ile Thr Val Val Asp Ala Leu His Glu Ile Pro Val Lys Lys Gly Glu
                        325                 330                 335

Gly Ala Glu Leu
                        340

<210> SEQ ID NO 6
<211> LENGTH: 1141
<212> TYPE: DNA
<213> ORGANISM: Bos taurus

<400> SEQUENCE: 6
gactcgcgct cccgctgccg ccaccgcgcc ccgccatgga gcggccgccg ctgcccgccc      60
tgctcctcgg cgccgccggg ctgctgctcc tgctcctgcc cctctcctct tcctcctctt     120
cggacgcctg cggcccctgc gagccggccg cctgcccgcc cctgccccg cggggctgcc      180 agctgggcga cccgcgac gcgtgcggct gctgcccggt atgcgcccgc ggcgagggcg       240
agccgtgcgg gggcggcggc gccggcaggg ggcactgcgc gccgggcatg gagtgcgtga     300
agagccgcaa gaggcggagg ggtaaagccg gggcagcagc gggcggcccg gttgtgagcg     360
gcgtgtgtgt gtgcaagagc cgctaccccg tgtgcgcag cgacggtgtc acctactcca     420
gcggctgcca gctgcgcgcc gccagcctca gggccgagag ccgcggggag aaggccatca     480
cccaggtcag caagggcacc tgcgagcaag tccttccat cgtgacgccc ccaaggaca     540 tctggaatgt cactggtgcc caggtgtatt tgagctgcga ggtcatcgga atccccaccc     600
```

```
ctgtcctcat ctggaacaag gtaaaaaggg gtcactatgg agttcaaaga acagaactct    660
tgcctggtga ccgagacaac ctggccattc agacccgggg tggtccagaa aagcatgaag    720
ttactggctg ggtgctggta tctcctctta gtaaggaaga tgccggagaa tatgagtgcc    780
atgcatccaa ttcccaagga caggcttcag catcagcaaa aattacagtg gttgatgcct    840
tacatgaaat accagtgaaa aaggtgaag gtgctgagct gtaaacctgc agaatgtatt     900
agtctgcata gctaaaagta gtcatgggta actacagcct cctgttcttg cctagtaacc    960
agtttctttt catccagtcc actaacactt gagctatatt cactgatttt acacagtgaa   1020
atacgaaatt aagataacac accaagacta tctacaaaaa tttattgtct atttacagaa   1080
gaaaagcatg cgtatcatta aacaaataa aatgtgtttt ctcacaaaaa aaaaaaaaa     1140 a                                                                   1141
```

<210> SEQ ID NO 7
<211> LENGTH: 282
<212> TYPE: PRT
<213> ORGANISM: Bos taurus

<400> SEQUENCE: 7

```
Met Glu Arg Pro Pro Leu Pro Ala Leu Leu Gly Ala Ala Gly Leu
1               5                   10                  15

Leu Leu Leu Leu Pro Leu Ser Ser Ser Ser Ser Asp Ala Cys
            20                  25                  30

Gly Pro Cys Glu Pro Ala Ala Cys Pro Pro Leu Pro Pro Arg Gly Cys
        35                  40                  45

Gln Leu Gly Glu Thr Arg Asp Ala Cys Gly Cys Pro Val Cys Ala
    50                  55                  60

Arg Gly Glu Gly Glu Pro Cys Gly Gly Gly Ala Gly Arg Gly His
65                  70                  75                  80

Cys Ala Pro Gly Met Glu Cys Val Lys Ser Lys Arg Arg Gly
                85                  90                  95

Lys Ala Gly Ala Ala Ala Gly Gly Pro Val Val Ser Gly Val Cys Val
                100                 105                 110

Cys Lys Ser Arg Tyr Pro Val Cys Gly Ser Asp Gly Val Thr Tyr Ser
            115                 120                 125

Ser Gly Cys Gln Leu Arg Ala Ala Ser Leu Arg Ala Glu Ser Arg Gly
        130                 135                 140

Glu Lys Ala Ile Thr Gln Val Ser Lys Gly Thr Cys Glu Gln Gly Pro
145                 150                 155                 160

Ser Ile Val Thr Pro Lys Asp Ile Trp Asn Val Thr Gly Ala Gln
                165                 170                 175

Val Tyr Leu Ser Cys Glu Val Ile Gly Ile Pro Thr Pro Val Leu Ile
            180                 185                 190

Trp Asn Lys Val Lys Arg Gly His Tyr Gly Val Gln Arg Thr Glu Leu
        195                 200                 205

Leu Pro Gly Asp Arg Asp Asn Leu Ala Ile Gln Thr Arg Gly Gly Pro
    210                 215                 220

Glu Lys His Glu Val Thr Gly Trp Val Leu Val Ser Pro Leu Ser Lys
225                 230                 235                 240

Glu Asp Ala Gly Glu Tyr Glu Cys His Ala Ser Asn Ser Gln Gly Gln
                245                 250                 255

Ala Ser Ala Ser Ala Lys Ile Thr Val Val Asp Ala Leu His Glu Ile
            260                 265                 270
```

Pro Val Lys Lys Gly Glu Gly Ala Glu Leu
             275                 280

<210> SEQ ID NO 8
<211> LENGTH: 1125
<212> TYPE: DNA
<213> ORGANISM: Rattus norvegicus

<400> SEQUENCE: 8

| | | | | | |
|---|---|---|---|---|---|
| cgcgtctagc | cacccatca | tggagcggtc | accgcgcgcc | ctgctgctgg | gtgcagccgg | 60 |
| attgctgctc | ctgctcctgc | ccctctcctc | ttcctcctct | tccgatgcct | gcggcccgtg | 120 |
| cgtgccggcc | tcctgccccg | cgctgccccc | gttcggctgc | ccgctgggtg | agacccgcga | 180 |
| cgcgtgcggc | tgctgcccag | tgtgcgctcg | cggcgagggt | gagccgtgcg | ggggcggcgc | 240 |
| ggccggcggg | gggcactgcg | cgccgggcat | ggagtgcgtg | aagagccgca | agaggcggag | 300 |
| gggtaaagcc | ggggcagcag | ccggcggtcc | cgcgaccctc | gccgtgtgcg | tgtgcaagag | 360 |
| ccgctacccg | gtgtgcggca | gcgacggcgt | cacctacccc | agcggctgcc | agctgcgcgc | 420 |
| cgccagcctg | cgcgctgaga | gccgcggaga | aaggccatc | acccaggtca | gcaaaggcac | 480 |
| ctgcgagcaa | ggtccttcca | tagtgacgcc | ccccaaggac | atctggaaca | tcactggcgc | 540 |
| caaggtgtac | ttgagctgcg | aagtcatcgg | aatcccaacc | cctgtcctca | tctggaacaa | 600 |
| ggtaaaaagg | gatcactctg | gagttcaaag | gacagaactc | ttgcctggtg | accgggaaaa | 660 |
| cctggccatt | cagacccggg | gtggtccaga | aaagcatgaa | gtaactggct | gggtgctggt | 720 |
| atctcctcta | agtaaggaag | acactggaga | atacgagtgc | cacgcgtcca | attcccaagg | 780 |
| acaggcttca | gcgtcggcca | aaattacagt | ggttgatgcc | atacacgaaa | taccagtgaa | 840 |
| aaaaggtgaa | ggtgctcagc | tataaacctg | cgaatacatt | agcctctgta | gctgacgcgc | 900 |
| tctcagacag | ctgacagctg | taaccccact | cctgcctgac | atattccttt | gaacctaaca | 960 |
| cactaacact | ttattacagc | cagctgattt | tacagagaaa | tcaaagataa | cacataagac | 1020 |
| tatctacaaa | agtttattgt | ttatttacag | aaaaagcatg | cagagcttta | aacaaaacaa | 1080 |
| ataaaattct | tattacaaca | ggaaaaaaaa | aaaaaaaaa | aaaaa | | 1125 |

<210> SEQ ID NO 9
<211> LENGTH: 281
<212> TYPE: PRT
<213> ORGANISM: Rattus norvegicus

<400> SEQUENCE: 9

Met Glu Arg Ser Pro Arg Ala Leu Leu Leu Gly Ala Ala Gly Leu Leu
1               5                   10                  15

Leu Leu Leu Leu Pro Leu Ser Ser Ser Ser Ser Asp Ala Cys Gly
            20                  25                  30

Pro Cys Val Pro Ala Ser Cys Pro Ala Leu Pro Pro Phe Gly Cys Pro
        35                  40                  45

Leu Gly Glu Thr Arg Asp Ala Cys Gly Cys Pro Val Cys Ala Arg
    50                  55                  60

Gly Glu Gly Glu Pro Cys Gly Gly Ala Gly Gly His Cys
65                  70                  75                  80

Ala Pro Gly Met Glu Cys Val Lys Ser Arg Lys Arg Arg Gly Lys
                85                  90                  95

Ala Gly Ala Ala Ala Gly Gly Pro Ala Thr Leu Ala Val Cys Val Cys
            100                 105                 110

Lys Ser Arg Tyr Pro Val Cys Gly Ser Asp Gly Val Thr Tyr Pro Ser

```
            115                 120                 125
Gly Cys Gln Leu Arg Ala Ala Ser Leu Arg Ala Glu Ser Arg Gly Glu
    130                 135                 140

Lys Ala Ile Thr Gln Val Ser Lys Gly Thr Cys Glu Gln Gly Pro Ser
145                 150                 155                 160

Ile Val Thr Pro Pro Lys Asp Ile Trp Asn Ile Thr Gly Ala Lys Val
                165                 170                 175

Tyr Leu Ser Cys Glu Val Ile Gly Ile Pro Thr Pro Val Leu Ile Trp
            180                 185                 190

Asn Lys Val Lys Arg Asp His Ser Gly Val Gln Arg Thr Glu Leu Leu
        195                 200                 205

Pro Gly Asp Arg Glu Asn Leu Ala Ile Gln Thr Arg Gly Gly Pro Glu
    210                 215                 220

Lys His Glu Val Thr Gly Trp Val Leu Val Ser Pro Leu Ser Lys Glu
225                 230                 235                 240

Asp Thr Gly Glu Tyr Glu Cys His Ala Ser Asn Ser Gln Gly Gln Ala
                245                 250                 255

Ser Ala Ser Ala Lys Ile Thr Val Val Asp Ala Ile His Glu Ile Pro
            260                 265                 270

Val Lys Lys Gly Glu Gly Ala Gln Leu
        275                 280
```

<210> SEQ ID NO 10
<211> LENGTH: 1279
<212> TYPE: DNA
<213> ORGANISM: Mus musculus

<400> SEQUENCE: 10

```
actcgcgcgc tcgcatccag ccaccttatg atggagcggc cgccgcgcgc cctgctgctg      60
ggtgcagccg gactgctgct cctgctcctg cccctctcct cttcctcctc ttcggatgcc     120
tgcggcccgt gcgtgccggc ctcctgcccc gcgctgcccc ggctcggctg cccgctgggt     180
gagacccgcg acgcgtgcgg gtgctgcccg gtgtgtgctc gcggcgaggg tgagccgtgc     240
gggggcggcg cggccggcgg gggcactgc gcgccgggca tggagtgcgt gaagagccgc     300
aagaggcgga ggggtaaagc cggggcagca gccggcggtc ccgcgaccct cgccgtgtgc     360
gtgtgcaaga gccgctaccc ggtgtgcggc agcaacggca tcacctaccc cagcggctgc     420
cagctgcgcg ctgccagcct gcgcgccgag agccgcgggg agaaggccat cacccaggtc     480
agcaagggca cctgcgagca aggtccttcc atagtgacgc cccccaagga catctggaac     540
gtcactggtg ccaaggtgtt cttgagctgt gaggtcatcg gtatcccaac ccctgtcctc     600
atctggaaca aggtaaaaag ggatcactct ggagttcagc ggacagaact cttgcctggt     660
gaccgggaaa atctggccat tcagacccgg ggtggtccag aaaagcatga agtaacgggc     720
tgggtgctgg tatctcctct aagtaaggag gacgctggag agtatgagtg ccacgcatcc     780
aactcccaag ggcaggcttc cgcggcagcc aaaattacag tggttgatgc cctccatgaa     840
ataccactga aaaaggtga aggtgctcag ttataacctg cgaatccatg agcctctgta     900
gctaaaggtg ctctcagaca gccgacagct ataaccctgc tcttgcctga cacacttctc     960
ttaacctaac ccactaacac tttattacag ccagctggtt ttacacagag aaatcaaaga    1020
taacacatca agactatcta caaaaattta ttatttacag aaaaaagcac atgtagcttt    1080
aaacaaaaca aataaaattc ttatcacaac aaaaaaaaaa aaaaaaaaaa aaaaaaaaaa    1140
aaaaaaaaaa aaaaaaaaaa aaaaaaaaaa aaaaaaaaaa aaaaaaaaaa aaaaaaaaaa    1200
```

```
aaaaaaaaaa aaaaaaaaaa aaaaaaaaaa aaaaaaaaaa aaaaaaaaaa aaaaaaaaaa    1260
aaaaaaaaaa aaaaaaaaa                                                  1279
```

```
<210> SEQ ID NO 11
<211> LENGTH: 281
<212> TYPE: PRT
<213> ORGANISM: Mus musculus

<400> SEQUENCE: 11
```

| | | | | | | | | | | | | | | |
|---|---|---|---|---|---|---|---|---|---|---|---|---|---|---|
|Met|Glu|Arg|Pro|Pro|Arg|Ala|Leu|Leu|Leu|Gly|Ala|Ala|Gly|Leu|
|1| | | |5| | | | |10| | | | |15|
|Leu|Leu|Leu|Leu|Pro|Leu|Ser|Ser|Ser|Ser|Ser|Asp|Ala|Cys|Gly|
| | | |20| | | | |25| | | | |30| |
|Pro|Cys|Val|Pro|Ala|Ser|Cys|Pro|Ala|Leu|Pro|Arg|Leu|Gly|Cys|Pro|
| | | | |35| | | | |40| | | | |45| |
|Leu|Gly|Glu|Thr|Arg|Asp|Ala|Cys|Gly|Cys|Cys|Pro|Val|Cys|Ala|Arg|
| | |50| | | | |55| | | | |60| | | |
|Gly|Glu|Gly|Glu|Pro|Cys|Gly|Gly|Ala|Ala|Gly|Gly|Gly|His|Cys|
|65| | | | |70| | | | |75| | | | |80|
|Ala|Pro|Gly|Met|Glu|Cys|Val|Lys|Ser|Arg|Lys|Arg|Arg|Gly|Lys|
| | | | |85| | | | |90| | | | |95| |
|Ala|Gly|Ala|Ala|Ala|Gly|Gly|Pro|Ala|Thr|Leu|Ala|Val|Cys|Val|Cys|
| | | |100| | | | |105| | | | |110| | |
|Lys|Ser|Arg|Tyr|Pro|Val|Cys|Gly|Ser|Asn|Gly|Ile|Thr|Tyr|Pro|Ser|
| | | |115| | | | |120| | | | |125| | |
|Gly|Cys|Gln|Leu|Arg|Ala|Ala|Ser|Leu|Arg|Ala|Glu|Ser|Arg|Gly|Glu|
| | |130| | | | |135| | | | |140| | | |
|Lys|Ala|Ile|Thr|Gln|Val|Ser|Lys|Gly|Thr|Cys|Glu|Gln|Gly|Pro|Ser|
|145| | | | |150| | | | |155| | | | |160|
|Ile|Val|Thr|Pro|Pro|Lys|Asp|Ile|Trp|Asn|Val|Thr|Gly|Ala|Lys|Val|
| | | | |165| | | | |170| | | | |175| |
|Phe|Leu|Ser|Cys|Glu|Val|Ile|Gly|Ile|Pro|Thr|Pro|Val|Leu|Ile|Trp|
| | | |180| | | | |185| | | | |190| | |
|Asn|Lys|Val|Lys|Arg|Asp|His|Ser|Gly|Val|Gln|Arg|Thr|Glu|Leu|Leu|
| | | |195| | | | |200| | | | |205| | |
|Pro|Gly|Asp|Arg|Glu|Asn|Leu|Ala|Ile|Gln|Thr|Arg|Gly|Gly|Pro|Glu|
| | |210| | | | |215| | | | |220| | | |
|Lys|His|Glu|Val|Thr|Gly|Trp|Val|Leu|Val|Ser|Pro|Leu|Ser|Lys|Glu|
|225| | | | |230| | | | |235| | | | |240|
|Asp|Ala|Gly|Glu|Tyr|Glu|Cys|His|Ala|Ser|Asn|Ser|Gln|Gly|Gln|Ala|
| | | | |245| | | | |250| | | | |255| |
|Ser|Ala|Ala|Ala|Lys|Ile|Thr|Val|Val|Asp|Ala|Leu|His|Glu|Ile|Pro|
| | | |260| | | | |265| | | | |270| | |
|Leu|Lys|Lys|Gly|Glu|Gly|Ala|Gln|Leu|
| | |275| | | | |280| |

```
<210> SEQ ID NO 12
<211> LENGTH: 282
<212> TYPE: PRT
<213> ORGANISM: Homo sapiens

<400> SEQUENCE: 12
```

| | | | | | | | | | | | | | | |
|---|---|---|---|---|---|---|---|---|---|---|---|---|---|---|
|Met|Glu|Arg|Pro|Ser|Leu|Arg|Ala|Leu|Leu|Leu|Gly|Ala|Ala|Gly|Leu|
|1| | | |5| | | | |10| | | | |15| |
|Leu|Leu|Leu|Leu|Leu|Pro|Leu|Ser|Ser|Ser|Ser|Ser|Ser|Asp|Thr|Cys|

```
            20                  25                  30
Gly Pro Cys Glu Pro Ala Ser Cys Pro Pro Leu Pro Pro Leu Gly Cys
            35                  40                  45

Leu Leu Gly Glu Thr Arg Asp Ala Cys Gly Cys Cys Pro Met Cys Ala
        50                  55                  60

Arg Gly Glu Gly Glu Pro Cys Gly Gly Gly Ala Gly Arg Gly Tyr
65                  70                  75                  80

Cys Ala Pro Gly Met Glu Cys Val Lys Ser Arg Lys Arg Arg Lys Gly
                85                  90                  95

Lys Ala Gly Ala Ala Ala Gly Gly Pro Gly Val Ser Gly Val Cys Val
            100                 105                 110

Cys Lys Ser Arg Tyr Pro Val Cys Gly Ser Asp Gly Thr Thr Tyr Pro
            115                 120                 125

Ser Gly Cys Gln Leu Arg Ala Ala Ser Gln Arg Ala Glu Ser Arg Gly
        130                 135                 140

Glu Lys Ala Ile Thr Gln Val Ser Lys Gly Thr Cys Glu Gln Gly Pro
145                 150                 155                 160

Ser Ile Val Thr Pro Pro Lys Asp Ile Trp Asn Val Thr Gly Ala Gln
                165                 170                 175

Val Tyr Leu Ser Cys Glu Val Ile Gly Ile Pro Thr Pro Val Leu Ile
            180                 185                 190

Trp Asn Lys Val Lys Arg Gly His Tyr Gly Val Gln Arg Thr Glu Leu
        195                 200                 205

Leu Pro Gly Asp Arg Asp Asn Leu Ala Ile Gln Thr Arg Gly Gly Pro
        210                 215                 220

Glu Lys His Glu Val Thr Gly Trp Val Leu Val Ser Pro Leu Ser Lys
225                 230                 235                 240

Glu Asp Ala Gly Glu Tyr Glu Cys His Ala Ser Asn Ser Gln Gly Gln
                245                 250                 255

Ala Ser Ala Ser Ala Lys Ile Thr Val Val Asp Ala Leu His Glu Ile
            260                 265                 270

Pro Val Lys Lys Gly Glu Gly Ala Glu Leu
        275                 280

<210> SEQ ID NO 13
<211> LENGTH: 282
<212> TYPE: PRT
<213> ORGANISM: Homo sapiens

<400> SEQUENCE: 13

Met Glu Arg Pro Ser Leu Arg Ala Leu Leu Leu Gly Ala Ala Gly Leu
1               5                   10                  15

Leu Leu Leu Leu Leu Pro Leu Ser Ser Ser Ser Ser Asp Thr Cys
            20                  25                  30

Gly Pro Cys Glu Pro Ala Ser Cys Pro Pro Leu Pro Pro Leu Gly Cys
            35                  40                  45

Leu Leu Gly Glu Thr Arg Asp Ala Cys Gly Cys Cys Pro Met Cys Ala
        50                  55                  60

Arg Gly Glu Gly Glu Pro Cys Gly Gly Gly Ala Gly Arg Gly Tyr
65                  70                  75                  80

Cys Ala Pro Gly Met Glu Cys Val Lys Ser Arg Lys Arg Arg Lys Gly
                85                  90                  95

Lys Ala Gly Ala Ala Ala Gly Gly Pro Gly Val Ser Gly Val Cys Val
            100                 105                 110
```

```
Cys Lys Ser Arg Tyr Pro Val Cys Gly Ser Asp Gly Thr Thr Tyr Pro
            115                 120                 125

Ser Gly Cys Gln Leu Arg Ala Ala Ser Gln Arg Ala Glu Ser Arg Gly
        130                 135                 140

Glu Lys Ala Ile Thr Gln Val Ser Lys Gly Thr Cys Glu Gln Gly Pro
145                 150                 155                 160

Ser Ile Val Thr Pro Pro Lys Asp Ile Trp Asn Val Thr Gly Ala Gln
                165                 170                 175

Val Tyr Leu Ser Cys Glu Val Ile Gly Ile Pro Thr Pro Val Leu Ile
            180                 185                 190

Trp Asn Lys Val Lys Arg Gly His Tyr Gly Val Gln Arg Thr Glu Leu
        195                 200                 205

Leu Pro Gly Asp Arg Asp Asn Leu Ala Ile Gln Thr Arg Gly Gly Pro
    210                 215                 220

Glu Lys His Glu Val Thr Gly Trp Val Leu Val Ser Pro Leu Ser Lys
225                 230                 235                 240

Glu Asp Ala Gly Glu Tyr Glu Cys His Ala Ser Asn Ser Gln Gly Gln
                245                 250                 255

Ala Ser Ala Ser Ala Lys Ile Thr Val Val Asp Ala Leu His Glu Ile
            260                 265                 270

Pro Val Lys Lys Gly Glu Gly Ala Glu Leu
        275                 280

<210> SEQ ID NO 14
<211> LENGTH: 282
<212> TYPE: PRT
<213> ORGANISM: Homo sapiens

<400> SEQUENCE: 14

Met Glu Arg Pro Ser Leu Arg Ala Leu Leu Gly Ala Ala Gly Leu
1               5                   10                  15

Leu Leu Leu Leu Leu Pro Leu Ser Ser Ser Ser Ser Asp Thr Cys
        20                  25                  30

Gly Pro Cys Glu Pro Ala Ser Cys Pro Pro Leu Pro Pro Leu Gly Cys
        35                  40                  45

Leu Leu Gly Glu Thr Arg Asp Ala Cys Gly Cys Cys Pro Met Cys Ala
    50                  55                  60

Arg Gly Glu Gly Glu Pro Cys Gly Gly Gly Ala Gly Arg Gly Tyr
65                  70                  75                  80

Cys Ala Pro Gly Met Glu Cys Val Lys Ser Arg Lys Arg Arg Lys Gly
                85                  90                  95

Lys Ala Gly Ala Ala Ala Gly Gly Pro Gly Val Ser Gly Val Cys Val
            100                 105                 110

Cys Lys Ser Arg Tyr Pro Val Cys Gly Ser Asp Gly Thr Thr Tyr Pro
            115                 120                 125

Ser Gly Cys Gln Leu Arg Ala Ala Ser Gln Arg Ala Glu Ser Arg Gly
        130                 135                 140

Glu Lys Ala Ile Thr Gln Val Ser Lys Gly Thr Cys Glu Gln Gly Pro
145                 150                 155                 160

Ser Ile Val Thr Pro Pro Lys Asp Ile Trp Asn Val Thr Gly Ala Gln
                165                 170                 175

Val Tyr Leu Ser Cys Glu Val Ile Gly Ile Pro Thr Pro Val Leu Ile
            180                 185                 190

Trp Asn Lys Val Lys Arg Gly His Tyr Gly Val Gln Arg Thr Glu Leu
        195                 200                 205
```

```
Leu Pro Gly Asp Arg Asp Asn Leu Ala Ile Gln Thr Arg Gly Gly Pro
        210                 215                 220

Glu Lys His Glu Val Thr Gly Trp Val Leu Val Ser Pro Leu Ser Lys
225                 230                 235                 240

Glu Asp Ala Gly Glu Tyr Glu Cys His Ala Ser Asn Ser Gln Gly Gln
                245                 250                 255

Ala Ser Ala Ser Ala Lys Ile Thr Val Val Asp Ala Leu His Glu Ile
            260                 265                 270

Pro Val Lys Lys Gly Glu Gly Ala Glu Leu
            275                 280

<210> SEQ ID NO 15
<211> LENGTH: 194
<212> TYPE: PRT
<213> ORGANISM: Homo sapiens

<400> SEQUENCE: 15

Arg Ala Ala Ser Arg Lys Gly Lys Ala Gly Ala Ala Gly Gly
1               5                   10                  15

Pro Gly Val Ser Gly Val Cys Val Cys Lys Ser Arg Tyr Pro Val Cys
                20                  25                  30

Gly Ser Asp Gly Thr Thr Tyr Pro Ser Gly Cys Gln Leu Arg Ala Ala
            35                  40                  45

Ser Gln Arg Ala Glu Ser Arg Gly Glu Lys Ala Ile Thr Gln Val Ser
    50                  55                  60

Lys Gly Thr Cys Glu Gln Gly Pro Ser Ile Val Thr Pro Pro Lys Asp
65                  70                  75                  80

Ile Trp Asn Val Thr Gly Ala Gln Val Tyr Leu Ser Cys Glu Val Ile
                85                  90                  95

Gly Ile Pro Thr Pro Val Leu Ile Trp Asn Lys Val Lys Arg Gly His
                100                 105                 110

Tyr Gly Val Gln Arg Thr Glu Leu Leu Pro Gly Asp Arg Asp Asn Leu
            115                 120                 125

Ala Ile Gln Thr Arg Gly Gly Pro Glu Lys His Glu Val Thr Gly Trp
130                 135                 140

Val Leu Val Ser Pro Leu Ser Lys Glu Asp Ala Gly Glu Tyr Glu Cys
145                 150                 155                 160

His Ala Ser Asn Ser Gln Gly Gln Ala Ser Ala Ser Ala Lys Ile Thr
                165                 170                 175

Val Val Asp Ala Leu His Glu Ile Pro Val Lys Lys Gly Glu Gly Ala
            180                 185                 190

Glu Leu

<210> SEQ ID NO 16
<211> LENGTH: 194
<212> TYPE: PRT
<213> ORGANISM: Homo sapiens

<400> SEQUENCE: 16

Arg Ala Ala Ser Arg Lys Gly Lys Ala Gly Ala Ala Gly Gly
1               5                   10                  15

Pro Gly Val Ser Gly Val Cys Val Cys Lys Ser Arg Tyr Pro Val Cys
                20                  25                  30

Gly Ser Asp Gly Thr Thr Tyr Pro Ser Gly Cys Gln Leu Arg Ala Ala
            35                  40                  45
```

```
Ser Gln Arg Ala Glu Ser Arg Gly Glu Lys Ala Ile Thr Gln Val Ser
    50                  55                  60

Lys Gly Thr Cys Glu Gln Gly Pro Ser Ile Val Thr Pro Pro Lys Asp
65                  70                  75                  80

Ile Trp Asn Val Thr Gly Ala Gln Val Tyr Leu Ser Cys Glu Val Ile
                    85                  90                  95

Gly Ile Pro Thr Pro Val Leu Ile Trp Asn Lys Val Lys Arg Gly His
                100                 105                 110

Tyr Gly Val Gln Arg Thr Glu Leu Leu Pro Gly Asp Arg Asp Asn Leu
            115                 120                 125

Ala Ile Gln Thr Arg Gly Gly Pro Glu Lys His Glu Val Thr Gly Trp
    130                 135                 140

Val Leu Val Ser Pro Leu Ser Lys Glu Asp Ala Gly Glu Tyr Glu Cys
145                 150                 155                 160

His Ala Ser Asn Ser Gln Gly Gln Ala Ser Ala Ser Ala Lys Ile Thr
                165                 170                 175

Val Val Asp Ala Leu His Glu Ile Pro Val Lys Lys Gly Glu Gly Ala
            180                 185                 190

Glu Leu

<210> SEQ ID NO 17
<211> LENGTH: 283
<212> TYPE: PRT
<213> ORGANISM: Artificial sequence
<220> FEATURE:
<223> OTHER INFORMATION: Synthetic construct

<400> SEQUENCE: 17

Met Glu Arg Pro Ser Leu Arg Ala Leu Leu Leu Gly Ala Ala Gly Leu
1               5                   10                  15

Leu Leu Leu Leu Leu Pro Leu Ser Ser Ser Ser Ser Asp Thr Cys
                20                  25                  30

Gly Pro Cys Glu Pro Ala Ser Cys Pro Pro Leu Pro Pro Leu Gly Cys
                35                  40                  45

Leu Leu Gly Glu Thr Arg Asp Ala Cys Gly Cys Cys Pro Met Cys Ala
50                  55                  60

Arg Gly Glu Gly Glu Pro Cys Gly Gly Gly Ala Gly Arg Gly Tyr
65                  70                  75                  80

Cys Ala Pro Gly Met Glu Cys Val Lys Ser Arg Lys Arg Arg Lys Gly
                85                  90                  95

Lys Ala Gly Ala Ala Ala Gly Gly Pro Gly Val Ser Gly Val Cys Val
                100                 105                 110

Cys Lys Ser Arg Tyr Pro Val Cys Gly Ser Asp Gly Thr Thr Tyr Pro
            115                 120                 125

Ser Gly Cys Gln Leu Arg Ala Ala Ser Gln Arg Ala Glu Ser Arg Gly
    130                 135                 140

Glu Lys Ala Ile Thr Gln Val Ser Lys Gly Thr Cys Glu Gln Gly Pro
145                 150                 155                 160

Ser Ile Val Thr Pro Pro Lys Asp Ile Trp Asn Val Thr Gly Ala Gln
                165                 170                 175

Val Tyr Leu Ser Cys Glu Val Ile Gly Ile Pro Thr Pro Val Leu Ile
            180                 185                 190

Trp Asn Lys Val Lys Arg Gly His Tyr Gly Val Gln Arg Thr Glu Leu
        195                 200                 205

Leu Pro Gly Asp Arg Asp Asn Leu Ala Ile Gln Thr Arg Gly Gly Pro
```

```
                    210                 215                 220
Glu Lys His Glu Val Thr Gly Trp Val Leu Val Ser Pro Leu Ser Lys
225                 230                 235                 240

Glu Asp Ala Gly Glu Tyr Glu Cys His Ala Ser Asn Ser Gln Gly Gln
                245                 250                 255

Ala Ser Ala Ser Ala Lys Ile Thr Val Val Asp Ala Leu His Glu Ile
                260                 265                 270

Pro Val Lys Lys Gly Glu Gly Ala Glu Leu Leu
                275                 280

<210> SEQ ID NO 18
<211> LENGTH: 283
<212> TYPE: PRT
<213> ORGANISM: Artificial sequence
<220> FEATURE:
<223> OTHER INFORMATION: Synthetic construct

<400> SEQUENCE: 18

Met Glu Arg Pro Ser Leu Arg Ala Leu Leu Gly Ala Ala Gly Leu
1               5                   10                  15

Leu Leu Leu Leu Leu Pro Leu Ser Ser Ser Ser Ser Asp Thr Cys
                20                  25                  30

Gly Pro Cys Glu Pro Ala Ser Cys Pro Pro Leu Pro Pro Leu Gly Cys
                35                  40                  45

Leu Leu Gly Glu Thr Arg Asp Ala Cys Gly Cys Cys Pro Met Cys Ala
50                  55                  60

Arg Gly Glu Gly Glu Pro Cys Gly Gly Gly Ala Gly Arg Gly Tyr
65                  70                  75                  80

Cys Ala Pro Gly Met Glu Cys Val Lys Ser Arg Lys Arg Arg Arg Gly
                85                  90                  95

Lys Ala Gly Ala Ala Ala Gly Gly Pro Gly Val Ser Gly Val Cys Val
                100                 105                 110

Cys Lys Ser Arg Tyr Pro Val Cys Gly Ser Asp Gly Thr Thr Tyr Pro
                115                 120                 125

Ser Gly Cys Gln Leu Arg Ala Ala Ser Gln Arg Ala Glu Ser Arg Gly
                130                 135                 140

Glu Lys Ala Ile Thr Gln Val Ser Lys Gly Thr Cys Glu Gln Gly Pro
145                 150                 155                 160

Ser Ile Val Thr Pro Pro Lys Asp Ile Trp Asn Val Thr Gly Ala Gln
                165                 170                 175

Val Tyr Leu Ser Cys Glu Val Ile Gly Ile Pro Thr Pro Val Leu Ile
                180                 185                 190

Trp Asn Lys Val Lys Arg Gly His Tyr Gly Val Gln Arg Thr Glu Leu
                195                 200                 205

Leu Pro Gly Asp Arg Asp Asn Leu Ala Ile Gln Thr Arg Gly Gly Pro
                210                 215                 220

Glu Lys His Glu Val Thr Gly Trp Val Leu Val Ser Pro Leu Ser Lys
225                 230                 235                 240

Glu Asp Ala Gly Glu Tyr Glu Cys His Ala Ser Asn Ser Gln Gly Gln
                245                 250                 255

Ala Ser Ala Ser Ala Lys Ile Thr Val Val Asp Ala Leu His Glu Ile
                260                 265                 270

Pro Val Lys Lys Gly Glu Gly Ala Glu Leu Leu
                275                 280
```

```
<210> SEQ ID NO 19
<211> LENGTH: 283
<212> TYPE: PRT
<213> ORGANISM: Artificial sequence
<220> FEATURE:
<223> OTHER INFORMATION: Synthetic construct

<400> SEQUENCE: 19

Met Glu Arg Pro Ser Leu Arg Ala Leu Leu Leu Gly Ala Ala Gly Leu
1               5                   10                  15

Leu Leu Leu Leu Leu Pro Leu Ser Ser Ser Ser Ser Asp Thr Cys
            20                  25                  30

Gly Pro Cys Glu Pro Ala Ser Cys Pro Pro Leu Pro Pro Leu Gly Cys
        35                  40                  45

Leu Leu Gly Glu Thr Arg Asp Ala Cys Gly Cys Cys Pro Met Cys Ala
    50                  55                  60

Arg Gly Glu Gly Glu Pro Cys Gly Gly Gly Ala Gly Arg Gly Tyr
65                  70                  75                  80

Cys Ala Pro Gly Met Glu Cys Val Lys Ser Arg Lys Arg Lys Gly
                85                  90                  95

Lys Ala Gly Ala Ala Ala Gly Gly Pro Gly Val Ser Gly Val Cys Val
            100                 105                 110

Cys Lys Ser Arg Tyr Pro Val Cys Gly Ser Asp Gly Thr Thr Tyr Pro
        115                 120                 125

Ser Gly Cys Gln Leu Arg Ala Ala Ser Gln Arg Ala Glu Ser Arg Gly
    130                 135                 140

Glu Lys Ala Ile Thr Gln Val Ser Lys Gly Thr Cys Glu Gln Gly Pro
145                 150                 155                 160

Ser Ile Val Thr Pro Pro Lys Asp Ile Trp Asn Val Thr Gly Ala Gln
                165                 170                 175

Val Tyr Leu Ser Cys Glu Val Ile Gly Ile Pro Thr Pro Val Leu Ile
            180                 185                 190

Trp Asn Lys Val Lys Arg Gly His Tyr Gly Val Gln Arg Thr Glu Leu
        195                 200                 205

Leu Pro Gly Asp Arg Asp Asn Leu Ala Ile Gln Thr Arg Gly Gly Pro
    210                 215                 220

Glu Lys His Glu Val Thr Gly Trp Val Leu Val Ser Pro Leu Ser Lys
225                 230                 235                 240

Glu Asp Ala Gly Glu Tyr Glu Cys His Ala Ser Asn Ser Gln Gly Gln
                245                 250                 255

Ala Ser Ala Ser Ala Lys Ile Thr Val Val Asp Ala Leu His Glu Ile
            260                 265                 270

Pro Val Lys Lys Gly Glu Gly Ala Glu Leu Leu
        275                 280

<210> SEQ ID NO 20
<211> LENGTH: 277
<212> TYPE: PRT
<213> ORGANISM: Artificial sequence
<220> FEATURE:
<223> OTHER INFORMATION: Synthetic construct

<400> SEQUENCE: 20

Met Glu Arg Ala Ser Leu Arg Ala Leu Leu Phe Gly Ala Ala Gly Leu
1               5                   10                  15

Leu Leu Leu Leu Leu Pro Leu Ser Ser Ser Ser Ser Asp Thr Cys
            20                  25                  30
```

```
Gly Pro Cys Glu Pro Ala Ser Cys Pro Pro Leu Pro Pro Leu Gly Cys
         35                  40                  45
Leu Leu Gly Glu Thr Arg Asp Ala Cys Gly Cys Pro Met Cys Ala
 50                  55                  60
Arg Gly Glu Gly Glu Pro Cys Gly Gly Gly Ala Gly Arg Gly Tyr
 65                  70                  75                  80
Cys Ala Pro Gly Met Glu Cys Val Lys Ser Lys Arg Arg Gly
                 85                  90                  95
Lys Ala Gly Ala Ala Gly Gly Pro Gly Val Ser Gly Val Cys Val
                100                 105                 110
Cys Lys Ser Arg Tyr Pro Val Cys Gly Ser Asp Gly Thr Thr Tyr Pro
             115                 120                 125
Ser Gly Cys Gln Leu Arg Ala Ala Ser Gln Arg Ala Glu Ser Arg Gly
         130                 135                 140
Glu Lys Ala Ile Thr Gln Val Ser Lys Gly Thr Cys Glu Gln Gly Pro
145                 150                 155                 160
Ser Ile Val Thr Pro Pro Lys Asp Ile Trp Asn Val Thr Gly Ala Gln
                 165                 170                 175
Val Tyr Leu Ser Cys Glu Val Ile Gly Ile Pro Thr Pro Val Leu Ile
             180                 185                 190
Trp Asn Lys Val Lys Arg Gly His Tyr Gly Val Gln Arg Thr Glu Leu
         195                 200                 205
Leu Pro Gly Asp Arg Asp Asn Leu Ala Ile Gln Thr Arg Gly Gly Pro
         210                 215                 220
Glu Lys His Glu Val Thr Gly Trp Val Leu Val Ser Pro Leu Ser Lys
225                 230                 235                 240
Glu Asp Ala Gly Glu Tyr Glu Cys His Ala Ser Asn Ser Gln Gly Gln
                 245                 250                 255
Ala Ser Ala Ser Ala Lys Ile Thr Val Val Asp Ala Leu His Glu Ile
             260                 265                 270
Ala Ser Glu Lys Arg
         275

<210> SEQ ID NO 21
<211> LENGTH: 2350
<212> TYPE: DNA
<213> ORGANISM: Homo sapiens

<400> SEQUENCE: 21
aagcttatat tccatgctag ggttctggtg ttggtgcgtg gggttggggt gggactgcag      60
aagtgccttt taagattatg tgattgactg atctgtcatt ggttccctgc catctttatc     120
ttttggattc ccctcggagg agggaggaa ggagtttctt ttgggttttta ttgaatcaaa     180 tgaaagggaa agtagaggtg ttcctatgga ggggaggaag gagtttcttt tgggttttat     240
tgaatcaaat gaaagggaaa gtagaggtgt tcctatgtcc cgggctccgg agcttctatt     300
cctgggccct gcataagaag gagacatggt ggtggtggtg gtgggtgggg gtggtggggc     360
acagaggaag ccgatgctgg gctctgcacc ccattcccgc tcccagatcc ctctggatat     420 agcacccccct ccagtgagca cagcctcccc ttgccccaca gccaacagca acatgcctcc     480
caacaaagca tctgtccctc agccaaaacc cctgttgcct ctctctgggg aaattgtagg     540
gctgggccag ggtgggggga ccattctctg cagggagatt aggagtgtct gtcaggggcg     600
ggtggagcgg ggtggggccc tggcttactc acatccttga gagtcctttg ctggcagatt     660
tgggagcccc acagctcaga tgtctgtctc agcattgtct tccaagctcc taggccacag     720
```

```
tagtggggcg ctcccttctc tggcttcttc tttggtgaca gtcaaggtgg ggttggggt      780 gacgaagggt cctgcttctc ttctaggagc agttgatccc aggaagagca ttggagcctc      840
cagcaggggc tgttggggcc tgtctgagga gataggatgc gtcaggcagc cccagacacg      900
atcacattcc tctcaacatg cctgccgggg tctgtggagc cgaggggctg atgggagggt      960
ggggtggggg ccggaagggt ttgctttggg aggttgtctg ggagattgct gaagttttga     1020
tatacacacc tccaaagcag gaccaagtgg actcctagaa atgtcccctg acccttgggg     1080
cttcaggagt cagggaccct cgtgtccacc tcagccttgc ccttgcacag cccagctcca     1140
ctccagcctc tactcctccc cagaacatct cctgggccag ttccacaagg ggctcaaacg     1200
agggcacctg agctgcccac actagggatg ttctgggggt ctgagaagat atctggggct     1260
ggaagaataa aaggcccccc taggcctgtt cctggatgca gctccagcca ctttggggct     1320
aagcctgggc aataacaatg ccaacgaggc ttcttgccat actcggttta caaaacccttt     1380 tacatacatt gtcgcattgg attctcagag ctgactgcac taagcagaat agatggtatg     1440
actcccactt tgcagatgag aacactgagg ctcagagaag tgcgaagccc tgggtcacag     1500
aggcgtaaat gcagagccag gacccacctg aagacccacc tgactccagg atgtttcctg     1560
cctccatgag gccacctgcc ctatggtgtg gtggatgtga tcctcacc atagggagga      1620 gattagggtc tgtgctcagg gctggggaga ggtgcctgga tttctctttg atggggatgt     1680
tggggtggga atcacgatac acctgatcag ctgggtgtat tcagggatg gggcagactt      1740 ctcagcacag cacggcaggt caggcctggg agggcccccc agacctcctt gtctctaata     1800
gagggtcatg gtgagggagg cctgtctgtg cccaaggtga ccttgccatg ccggtgcttt     1860
ccagccgggt atccatcccc tgcagcagca ggcttcctct acgtggatgt taaaggccca     1920
ttcagttcat ggagagctag caggaaacta ggtttaaggt gcagaggccc tgctctctgt     1980
caccctggct aagcccagtg cgtgggttcc tgagggctgg gactcccagg gtccgatggg     2040
aaagtgtagc ctgcaggccc acacctcccc ctgtgaatca cgcctggcgg gacaagaaag     2100
cccaaaacac tccaaacaat gagttttccag taaaatatga cagacatgat gaggcggatg     2160
agaggaggga cctgcctggg agttggcgct agcctgtggg tgatgaaagc caaggggaat     2220
ggaaagtgcc agacccgccc cctacccatg agtataaagc actcgcatcc ctttgcaatt     2280
tacccgagca ccttctcttc actcagcctt ctgctcgctc gctcacctcc ctcctctgca     2340
ccatgactac                                                             2350
```

<210> SEQ ID NO 22
<211> LENGTH: 2240
<212> TYPE: DNA
<213> ORGANISM: Homo sapiens

<400> SEQUENCE: 22

```
gctagggttc tggtgttggt gcgtgggtt ggggtgggac tgcagaagtg ccttttaaga      60
ttatgtgatt gactgatctg tcattggttc cctgccatct ttatcttttg gattccctc     120 ggaggagggg gaggaaggag tttcttttgg gttttattga atcaaatgaa agggaaagta     180
gaggtgttcc tatgtcccgg gctccggagc ttctattcct gatccctgca taagaaggag     240
acatggtggt ggtggtggtg gtgggggtg gtggggcaca gaggaagccg atactgggct     300 ctgcaccccca ttcccgctcc cagatccctc tggacacagc attttctcc agtgagcaca     360 gcctccccttt gccccacagc caacagcaac atgcctccca acaaaagcat ctgtccctca     420
```

```
gccaaaaccc ctgttgcctc tctctgggga aattgtaggg ctgggccagg gtgggggggac    480 cattctctgc agggagatta ggagtktctg tcagggcgg gtggagcggg gtggggcct      540 ggcttactca catccttgag agtcctttgc tggcagattt ggggagccca cagctcagat    600
gtctgtctca gcattgtctt ccaagctcct aggccacagt agtgggggc tcccttctct     660 ggcttcttct ttggtgacag tcaaggtggg gttggggtg acagagggtc ctgcttctct     720
tctaggagca gttgatccca ggaagagcat tggagcctcc agcagggct gttgggcct      780 gtctgaggag ataggatgcg tcaggcagcc ccagacacga tcacattcct ctcaacatgc    840 ctgccgggt ctgtggagcc gaggggctga tgggagggtg gggtggggc cggaagggtt      900 tgctttggga ggttgtctgg gagattgctg aagttttgat atacacacct ccaaagcagg    960
accaagtgga ctcctacccc tgaccccttgg ggcttcagga gtcagggacc ctcgtgtcca   1020
cctcagcctt gcccttggca cagcccagct ccactccagc ctctactcct ccccagaaca    1080
tctcctgggc cagttccaca aggggctcaa acgagggcac ctgagctgcc cacactaggg    1140
atgttctggg ggtctgagaa gatatctggg gctggaagaa taaaaggccc ccctaggcct    1200
gttcctggat gcagctccag ccactttggg gctaagcctg gctataaca atgccaacga     1260 ggcctcttgc catactcggt ttacaaaacc ctttcacata cattgtcgca ttggattctc    1320
agagctgact gcactaagca gaatagatgg tatgactccc actttgcaga tgagaacact    1380
gaggctcaga gaagtgccaa gccctgggtc acagaggcgt aaatggcaga gccaggaccc    1440
acctgactcc aggctgtttc ctggcctcca tgaggccacc tgccctatgg tgtggtggat    1500
gtgagatcct caccataggg aggagattag ggtctgtgct cagggctggg gagagctgcc    1560
tggatttctc tttgatgggg atgttggggt gggaatcacg atacacctga ctagctgggt    1620
gtatttcagg gatgggacag acttctcagc acagcacggc aggtcaggcc tgggagggcc    1680
ccccagacct ccttgtctct aatagagggt catggtgagg gaggcctgtc tgtgcccaag    1740
gtgaccttgc catgccggtg ctttccagcc gggtatccat cccctgcagc agcaggcttc    1800
ctctacgtgg atgttaaagg cccattcagt tcatggagag ctagcaggta actaggtta     1860 aggtgcagag gccctgctct ctgtcaccct ggctaagccc agtgcgtggg ttcctgaggg    1920
ctgggactcc cagggtccga tgggaaagtg tagcctgcag gcccacacct ccccctgtga    1980
atcacgcctg gcgggacaag aaagcccaaa acactccaaa caatgagttt ccagtaaaat    2040
atgacagaca tgatgaggcg gatgagagga gggacctggc tgggagttgg cgctagcctg    2100
tgggtgatga aagccaaggg gaatggaaag tgccagaccc gcccctacc catgagtata     2160 aagcactcgc atccctttcc aatttacccg agcaccttct cttcactcag ccaactgctg    2220
cgtcgctcac ctccctcctc                                                2240
```

<210> SEQ ID NO 23
<211> LENGTH: 2370
<212> TYPE: DNA
<213> ORGANISM: Homo sapiens

<400> SEQUENCE: 23

```
gtctgctccc tgcttggctg ggttgtttgc agctccttgg tcactgagtc cttgactgca     60
ggggaagaga ggttggcctc aggctccagg ttaggccacg gttctgagaa ccggtgtggg    120
ggatcaggct tatattccat gctagagctc cggagtcggt gcgtgggggtt gggatggggc   180 tgcagaagtg cctttaaga ttatgtgcat ggactgatct gtcactggtt ccctgccatc     240
tttatctttt ggattcccct tggagcaggg ggaggaagga gtttcttttg ggttccattg    300
```

```
aatcaaatga aagggaaagt aaagctgttc ctatgtcctg ggctctggag cttctattcc    360
tgatccctgc agaagaagga gacggtggtg gtggtgggtg ggggtagcgg ggcacagagg    420
aagccagtac cgggccctgc acccattcc cactcccaga tccctctgga cacagcattt    480
ttctccagtg agcacagcct tcccttgccc cacagccaac agcaacatgc ctcccaacaa    540
agcatctgc ccctcagcca aaaccctgt tgcctctctc tggggaaatt gtaggactgg     600
gtcagggtgg gggaaccatt ctctgcaggg agattaggag tgtctgtcag gggtgggtgg    660
agcggggtgg ggccctggct tactcacatc ctcgagagtc ctttgctggc agatttgggg    720
agcccacagc acaggtgtct gtctcagtat tgtcttccaa gctcctaggc cacagtagtg    780
ggggctccc ctctctggct tcttctttgg tgacagtcaa ggttgggggt ggggtgagag    840
agggtcctgc ttctcttcta ggaacagttg atcccaggaa gagcagtgga gcctccagca    900
ggggctgttg ggcctgtct gaggagatag gacgcgtcag gcagcccag acacgaccac      960
attcctccca acatgcctgc tgggtctgt ggagcccagg ggctgacggg agggtggggt    1020
ggggccgga agggtttgct ttgggaggtt gtctgggaga ttgctgaagt tttgatatac    1080
acacctccaa agcaggacca agtggactcc tagaaatgtc ccctgaccct tggggcttca    1140
ggagtcaggg accctcgtgt ccacttcagc cttgcccttg gcacagcctg gcaccactcc    1200
agcttctact cctccccaga acatctcctg ggccagttcc acaaggggct caaacgaggg    1260
cacctgagcc agacttctgc ctacactagg gatgttctgg gggtctgaga ggatatctgg    1320
ggctggaaga aaaaaaggcc ccctaggcc tgttcctgga tgcagctcca tccactttgg     1380
ggctaagcct gggctacaac aatgccaacc aggcttcttg ccatactcgg tttacaaaag    1440
cctttcacat acgctgtcgc attggcttct cacagctgac tgcagtaggc agagtagatg    1500
gtatgactcc cactttgcag atgagaacac tgaggctcag agaagcgcca agccctgggt    1560
cacggggccg taaatggcag agccaggacc cacctgactc caggctgttt cctggcctcc    1620
atgaggccac ccgccctatg gtgtggtgga tgtcagatcc tcaccgtagg gaggaaatta    1680
gggtctgtgc ccggggctgg ggagagctgc ctggatttct cttttgatggg ggtgttgggg   1740
tgggaatcac catacacctg actggctgag tgtatttcag ggatgggaca ggcttctcag    1800
cacagcatgg caggtcaggc ctgggagggc ccctcagacc tccttgtctc taacagcggg    1860
tcatggtgag ggacgcctct ctgtgcccaa ggtgaccttg ccatgccggt gctctccagc    1920
tgggtatctg tccctgcag tggtgggctt cctctaagtg gatggtaaag gcccatccag     1980
ttcatggaga gctagcaggt caccaggttt aaggtgcaga ggccctgctc tctgtcaccc    2040
tggctgagcc cagtgtgcgg gttcctgagg gctgggactc ccggggcccc atgggaaagt    2100
gtagcctgca ggcccatacc tcccctgtg aatcatgcct ggcgggacaa gaaagcccaa     2160
aacaccccaa acaatgagtt tccagtaaaa aatgacagac atgatgaggc ggaggagagg    2220
agggacctgg ctgggagttg tcactagcct gtgggtgatg aaagccaagg ggaatggaaa    2280
gtgccaggcc tgcccctac ccatgagtat aaagcactcg catcccttc caatttacct     2340
gagcaccttc tcttcactca gccaactgct                                    2370
```

<210> SEQ ID NO 24
<211> LENGTH: 262
<212> TYPE: DNA
<213> ORGANISM: Homo sapiens

<400> SEQUENCE: 24

```
aacatctggc tgcttctggg caccaattaa gtacattaag tggggagcga cagcagctaa    60
acaacccaag cccataaagc cttctaattg ctccgaccca cgtggtcaca gtctccccac   120
ttatataaaa ggcctacaga ggtgcaagta gtgaacgcct gatgccccga ccactgtgct   180
ctccattcgg acgtctccat cctcagaacc tcctctcttc cccaaaaagc accatgactt   240
gtggatctta ctgtggtggc cg                                            262

<210> SEQ ID NO 25
<211> LENGTH: 1103
<212> TYPE: DNA
<213> ORGANISM: Homo sapiens

<400> SEQUENCE: 25
aaaaacatta gctctgagaa gggatccata ggtttcatca ttctgccaaa gggatcccca    60
gcagcaaaaa agttatgaac tcctggtacc tgaattctgc accattacag aaaaccagga   120
cacacctagc aaacaactgg acagcaaatg gagcagcaga gtgcacacca ccagaccccg   180
ctggagaacg cccatctaga attgtgcaag cacagattga agggaggcct gcggggcagc   240
atgggtaccc agggctgaga agacagtca cggttttctt tgtttaggtg ttttgtcttc   300
ccccatctcc ttagtaccta gctccatgcc tggcagtttc tcagtagcta ttggccaagt   360
tgaagtgaat ctggatctag gtgggaagcc taaggctgga atacagaata tttccccttt   420
ttataggtac atggagccaa gaacatgtgg aggaataaga atgctaagaa tgacaaatat   480
acatgtggct tttgacagtt tacagagcac tccattaatc actagctcac tctatcctga   540
gaagtggcaa ggcaaatatt tgtattactt ccaatttaca gggaaagcaa ctggcctcag   600
agggtgactt gctccgtccg gtttgcagag ctaggaggtg acaggctgtg cgctcaaact   660
caggctgtct aactccacat tctgtggggt gagaggatgg gtgatggggt gtcttttctg   720
gaggagggag gtgctgtgag cctagcgaga tggaggtaca gtgggtgtgg gcctggagcg   780
ctgggcccag cagggggctt ctgattagga agccctgggg caccagttca ggttctccca   840
gagagtagtg tgatgggatc cagtaacctg tgccctccag atgacttctg taggtgtgtt   900
tagtgacatg ctcaacgggt gcgggaagga tggcttgtgc caaggccaag cccagagatg   960
tttcagattt ttcccttttat gcccctgcaa ccaagccctg ctgctccagg acatataaga  1020
gacgaaggct gagggctcca gcactcaccg gcctgggccc tgtcacttct ctgatagctc  1080
ccagctcgct ctctgcagcc atg                                          1103

<210> SEQ ID NO 26
<211> LENGTH: 1010
<212> TYPE: DNA
<213> ORGANISM: Homo sapiens

<400> SEQUENCE: 26
gaattctgca ccattacaga aaaccagaac acacctagca aacaactgga cagcaaatgg    60
agcagcagag tgcacaccac cagaccccgc tggagaacgc ccatctagaa ttgtgcaagc   120
acagattgaa gggaggcctg cggggcagca tgggtaccca gggctgagaa agacagtcac   180
ggttttcttt ggggaggtgt tttgtcttcc cccatctcct tagtacctag ttccatgcct   240
ggcagtttct cagtagctgt tggccaagtt gaagtgaatc tggatctagg ttggaaggct   300
aaggctggaa tacagaatat ttcccctttt tataggtaca tggagccaag aacatgtgga   360
ggaataagaa tgctaagaat gacaaatata catgtggctt ttgacagttt acagagcact   420
ccattaatca ctagctcact ctatcctgag aagtggcaag gcaaatattt gtattacttc   480
```

```
caatttacag ggaaagcaac tgggcctcag agggtgactt gctccggttt gcagagctag    540
gaggtggcag gctgtgcgct caaactcagg ctgtctaact ccacattctg tggggtgaga    600
ggatgggtga tggggtgtct tttctggagg agggaggtgc tgtgagccta gcgagatgga    660
ggtacagtgg gtgtgggcct ggagcgctgg gcccaggcag gggcttctga ttaggaagcc    720
ctggggcacc agttcaggtt ctcccagaga gtagtgtgat gggatccagt aacctgtgcc    780
ctccagatga cttctgtagg tgtgtttagt gacatgctca acgggtgcgg gaaggatggg    840
cttgtgccaa ggccaagccc agagatgttt cagatttttc cctttatgcc cctgcaacca    900
agccctgctg ctccaggaca tataagagac gaaggctgag ggctccagca ctcaccggcc    960
tgggccctgt cacttctctg atagctccca gctcgctctc tgcagccatg               1010
```

<210> SEQ ID NO 27
<211> LENGTH: 453
<212> TYPE: DNA
<213> ORGANISM: Homo sapiens

<400> SEQUENCE: 27

```
caacccattt ccccaccaga cagggttgag gcgggccagg ctggggtggt ggctgcctgg     60
gagggcctgg ggacgggtga cgtcctgcct tctcctcttc tccgtattag gtcatgggaa    120
agcatagctg gagggcccgc ctgaatcaca ggtgacgggc tgagaccag aggcacgcac    180 acgcacggca ctcagcacga ggatttggag aaatgaggca aattcctgat gatgggcggg    240
gagggagccc ccagccacct gggagctggc aggtggccag tggtgatgaa agcccagggg    300
aatggaaaca gaggagcaag cctgttgtaa tcgctacgcc cacttggtgg cctataaagg    360
aagcgggcga accccggcag ccctacacaa cttggggccc ctctcctccc cagcccttct    420
cctgtgtgcc tgcctcctgc cgccgccacc atg                                 453
```

<210> SEQ ID NO 28
<211> LENGTH: 908
<212> TYPE: DNA
<213> ORGANISM: Homo sapiens

<400> SEQUENCE: 28

```
ggatccccgg gtttcctaaa ccccccacag agtcctgccc aggccaaaga gcaaggaaaa     60
ggtcaaaggg cagaaaaaat gctgagttag gaggagctat ggaaggataa acctggcctt    120
aaagaggtca agtggtttta tagggggcgc tgagggcttc ccacattctc tggcctaaac    180
cttgcaggca gatctgccca gtgggctctg ggatagctgt gccttcccta acaaaaaaat    240
tgtgcacaaa aggatgaaac tctatttttcc ctctagcaca taaccaagaa tataaggcta    300
cagattgcct ttcccagagg gaaaaccctg cagcaacctg ctgcctggaa aagtgtaaga    360
gcagatcact ggggaatcgt ttgccccccg ctgatggaca gcttccccaa gctccaaggg    420
caggtgctca gcatgtaccg tactgggatg gttgtcaata ctcctggtcc tgtaagagtc    480
ccaggacact gccatgccaa tgccccctca gttcctggca tccttttgg gctgctcaca    540 gccccagcct ctatggtgaa gacatacttg ctagcagcgt caccaacttg ttgccaagag    600
atcagtgctc gaaggcaagg ttatttctaa ctgagcagag cctgccagga agaaagcgtt    660
tgcaccccac accactgtgc aggtgtgacc ggtgagctca cagctgcccc ccaggcatgc    720
ccagcccact taatcatcac agctcgacag ctctctcgcc cagcccagtt ctggaaggga    780 taaaagggg catcaccgtt cctgggtaac agagccacct tctgcgtcct gctgagctct    840
```

```
gttctctcca gcacctccca acccactagt gcctggttct cttgctccac caggaacaag    900
ccaccatg                                                              908
```

<210> SEQ ID NO 29
<211> LENGTH: 1261
<212> TYPE: DNA
<213> ORGANISM: Homo sapiens

<400> SEQUENCE: 29

```
agggggggtt gtgagtagga aggccagcat gtgagtgcat tgtgtgtgag tttgtgtgtg     60
tatgtgtgtg tgcaccagag agtgggagag agagagagaa aaaaacatgt tgataggtat    120
agataaggga tttgggagta ggtgtggagg aactgggtcc ctgagaaggt gactaagtta    180
gagattctgt aaacgtgggt cttttggggt gcagaaacag gtcatctagt tcggagaaac    240
caccaagcgc cccccaagtt ccacatcaag ggattccccc tcccaacatt cctggctagt    300
cctatgagca ccgcggacag cggcattgac catgtcaaac cccgcaggac agaaagagca    360
gcagccccgc ccctccctt ccattccaac ctgagtcact gcccactcct tcgtccaacg    420
tcagtttcct caactgtgta ttgggaggtt gaggtgggtg tgcgggacgt gagttggtcc    480
tttgaagaag aaaactgcag tttagggcaa gagatcataa catctggctg cttctgggca    540
ccaattaagt acattaagtg gggagcgaca gcagctaaac aacccaagcc cataaagcct    600
tctaattgct ccgaccacg tggtcacagt ctccccactt atataaaagg cctacagagg    660
tgcaagtagt gaacgcctga cgccccgacc actgtgctct ccattcggac gtctccatcc    720
tcagaacctc ctctcttccc caaaaagcac catgacttgt ggatcttact gtggtggccg    780
cgccttcagc tgcatctcgg cctgcgggcc ccggccggc cgctgctgca tcaccgccgc    840
cccctaccgt ggcatctcct gctaccgcgg cctcaccggg ggcttcggca ccacagcgt    900 gtgcggaggc tttcgggccg gctcctgcgg acgcagcttc ggctaccgct ccggggcgt    960 gtgcgggccc agtcccccat gcatcaccac cgtgtcggtc aacgagagcc tcctcacgcc   1020
cctcaacctg gagatcgacc ccaacgcgca gtgcgtgaag caggaggaga aggagcagat   1080
caagtccctc aacagcaggt tcgcggcctt catcgacaag gtgggtgtcc tggatcacac   1140
ccttcctgaa cccccaccac ctacacagcc agggccgggc actaaggatg gagtcagagg   1200
cacaaagacc tctgcctgcc tgagatccca gtctgatggg cgaggcacac agacacacag   1260
a                                                                    1261
```

<210> SEQ ID NO 30
<211> LENGTH: 1241
<212> TYPE: DNA
<213> ORGANISM: Homo sapiens

<400> SEQUENCE: 30

```
aaagtgagat ggttttcagc tgccaactga aaaatctgga gatggggaaa tccagatttg     60
tgtttcagga gcactttagc cacagctgtg atggaaatga gagatggtat ttattaatgc    120
ctcagccttt cctgaaaccc ctctccccac atcacactta acacacaggt ctcctcctcc    180
cagtttctcc cagcacctgg cctcccttct cttcccctcg ccaggctcta ctcctccttc    240
tcgtcctctc ctctgccttc cccttccctc cccaatgcct gcagatgaag gaatgccctg    300
ctggcaagac actttgaaga tgaaacatgc tgactccccc agagcccaag actgacatct    360
tttacaaaga agagggtgca ggccactccc ccattaaagc acattctgga gaggcgttag    420
acccggctaa ccacccaagc ccataaagcg caaattgccc caacatcatc ttcacagcca    480
```

```
agcccttca gaatctgcgc ataaataggg ctgcggtgcc ctgaggagca cattggagtt      540
tccatcagga ctccaggtcc cctatcctgt cctctgcaac ccaaacgtcc aggaggatca    600
tgacctgcgg atcaggattt ggtgggcgcg ccttcagctg catctcggcc tgcgggccgc    660
ggcccggccg ctgctgcatc accgccgccc cctaccgtgg catctcctgc taccgcggcc    720
tcaccggggg cttcggcagc cacagcgtgt gccgaggctt cgggccggc tcctgcggac     780 gcagcttcgg ctaccgctcc gggggcgtgt gcgggcccag tccccatgc atcaccaccg     840 tgtcggtcaa cgagagcctc ctcacgcccc tcaacctgga gatcgacccc aacgcgcagt    900
gcgtgaagca ggaggagaag gagcagatca agtccctcaa cagcaggttc gcggccttca    960
tcgacaaggt gggtgtcctg gatcacaccc ttcctgaacc cccaccacct acacagccag   1020
ggccgggcac taaggatgga gtcagaggca caaagacctc tgcctgcctg agatcccagt   1080
ctgatgggcg aggcacacag acacacagac agacagacac atgcacagac acacacacac   1140
aggcactcaa gatgcagact cagctgacag ttcagataga gggagcttgt gaaggaaaag   1200
tgtggccagg ctgctctggg gcacaagcta gacatcaggg a                       1241
```

<210> SEQ ID NO 31
<211> LENGTH: 1192
<212> TYPE: DNA
<213> ORGANISM: Homo sapiens

<400> SEQUENCE: 31

```
gacctgcatc actccttcca ttaagatact ttcccagagc tgtgagtggg ctccactgtc     60
tccactactc agagaagcag aacctcccca cacctcctcc actctatcct ctccagagct    120
gggcaccgct ctgagggccc agtgcagcta ataggcagag ggatggctgc tgagcacctg    180
atgcaggtga gcgtgcctcc tgggtcctgt cagacagagc taggaggagg ccatgcccaa    240
acatggggca acaccaggca ccaccccctc accaggtaag cctgccacct tagcactttt    300
accatttcag cttattttca aggtgtgttt ggtagcctgg aacaaactta ttgccttgga    360
ggcaaaccca gcccatgaat atctgggatt aattatctct ccttcgtttg agcccaacaa    420
cctcctcaaa tgtatataaa gggattttta ttgcacaggt cttcatttcc catccctctt    480
cctctgactc gtcagtgtcc ctgcttaact tacactcttc tcttcgccaa gctccttacc    540
atgagcagac aagccagcaa gacatctggt ggcgggagcc agggtttctc cgggcgctct    600
gctgtggtct ccggcagcag caggatgagc tgtgtggccc actctggggg agctggcgga    660
ggggcctatg gcttccggag cggagcaggt ggctttggca gtcgcagcct ctacaacctg    720
ggcggcaaca agagcatctc catcagcgtg gcagctggcg gctcccgggc tggaggcttt    780
gggggagggc ggagcagctg tgcctttgca ggtggctatg gaggtggctt ggggagcggc    840
tatggaggtg gctttggtgg tggctttggt ggtggcagag gaatgggagg tggctttggt    900
ggagctggtg gctttggagg ggctggtggc tttgagggg ctggtggctt tggtggtcct    960
ggtggctttg gtgggtctgg tggctttggt gggcctggca gcttgggcag tcctggtggc   1020
tttgcgcctg ggggctttcc tggggaatt caggaagtga ctactaacca gagtctcctg   1080
cagcccctca aagtggagac tgaccccag attgggcaag taaggcccca ggagcgggaa   1140
cagatcaaga ccctcaacaa caagtttgcc tccttcattg acaaggtaat aa           1192
```

<210> SEQ ID NO 32
<211> LENGTH: 21
<212> TYPE: DNA

```
<213> ORGANISM: Artificial sequence
<220> FEATURE:
<223> OTHER INFORMATION: SiRNA targeting IGFBP7

<400> SEQUENCE: 32
gcugguaucu ccucuaagut t                                              21

<210> SEQ ID NO 33
<211> LENGTH: 21
<212> TYPE: DNA
<213> ORGANISM: Artificial sequence
<220> FEATURE:
<223> OTHER INFORMATION: SiRNA targeting IGFBP7

<400> SEQUENCE: 33
acuuagagga gauaccagct t                                              21

<210> SEQ ID NO 34
<211> LENGTH: 58
<212> TYPE: DNA
<213> ORGANISM: Artificial sequence
<220> FEATURE:
<223> OTHER INFORMATION: ShRNA targeting IGFBP7

<400> SEQUENCE: 34
ccggcaatcc actaacactt tagttctcga gaactaaagt gttagtggat tgtttttg       58

<210> SEQ ID NO 35
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 35
cgagcaaggt ccttccatag tg                                             22

<210> SEQ ID NO 36
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 36
ccgatgacct cacagctcaa g                                              21

<210> SEQ ID NO 37
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 37
ggaagaatca aactatgagc tg                                             22

<210> SEQ ID NO 38
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 38
attgtcgatc tgaagcagg                                                 19
```

<210> SEQ ID NO 39
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 39
ctgaatggcg aaggcgtt                                              18

<210> SEQ ID NO 40
<211> LENGTH: 17
<212> TYPE: DNA
<213> ORGANISM: Artificial sequence
<220> FEATURE:
<223> OTHER INFORMATION: Single strand DNA oligonucleotide

<400> SEQUENCE: 40
ccactgccga caccact                                               17

<210> SEQ ID NO 41
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 41
tgttcctcct ccagtcaata                                            20

<210> SEQ ID NO 42
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 42
gctttgatgg gacctccact                                            20

<210> SEQ ID NO 43
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 43
cgatcacatt agtgccattc                                            20

<210> SEQ ID NO 44
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 44
aggtggacag cgaggccagg a                                          21

<210> SEQ ID NO 45
<211> LENGTH: 20
<212> TYPE: DNA
<213> ORGANISM: Artificial sequence
<220> FEATURE:

```
<223> OTHER INFORMATION: Single strand DNA oligonucleotide

<400> SEQUENCE: 45
gagtcaacgg atttggtcgt                                                    20

<210> SEQ ID NO 46
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 46
gacaagcttc ccgttctcag cc                                                 22
```